United States Patent
Brugel et al.

(10) Patent No.: US 7,402,589 B2
(45) Date of Patent: Jul. 22, 2008

(54) TRI-SUBSTITUTED UREAS AS CYTOKINE INHIBITORS

(75) Inventors: Todd Andrew Brugel, West Chester, OH (US); Jennifer Anne Townes, Loveland, OH (US); Michael Philip Clark, Maineville, OH (US); Mark Sabat, Loveland, OH (US); Adam Golebiowski, Loveland, OH (US); Biswanath De, Cincinnati, OH (US)

(73) Assignee: The Procter & Gamble Company, Cinncinati, OH (US)

( * ) Notice: Subject to any disclaimer, the term of this patent is extended or adjusted under 35 U.S.C. 154(b) by 566 days.

(21) Appl. No.: 11/111,612

(22) Filed: Apr. 21, 2005

(65) Prior Publication Data

US 2005/0245555 A1 Nov. 3, 2005

Related U.S. Application Data

(60) Provisional application No. 60/564,745, filed on Apr. 22, 2004.

(51) Int. Cl.
   *C07D 239/16* (2006.01)
   *A61K 31/505* (2006.01)
(52) U.S. Cl. ........................ 514/275; 544/323
(58) Field of Classification Search ................ 544/323; 514/275

See application file for complete search history.

(56) References Cited

OTHER PUBLICATIONS

Robinson, Medical Therapy of Inflammatory Bowel Disease for the 21st Century, Eur J Surg 1998; Suppl 582, pp. 90-98.*
Aleman et al. PubMed Abstract (Antivir Ther. 4(2):109-15), 1999.*
Rasmussen, PubMed Abstract (Dan Med Bull. 47(2):94-114), 2000.*
Green et al., PubMed Abstract (Immunol Rev 169:11-22), 1999.*
Van Deventer, PubMed Abstract (Intensive Care Med. 26 Suppl 1:S98-102), 2000.*
Holzheimer, PubMed Abstract (J Chemother. 13 Spec No 1(1): 159-72), 2001.*
Lesher et al., Novel orally active inhibitors of passive cutaneous anaphylaxis in rats, J. Med. Chem. 25(7), pp. 837-842, 1982.*

* cited by examiner

*Primary Examiner*—Deepak Rao
(74) *Attorney, Agent, or Firm*—Kelly L. McDow

(57) ABSTRACT

The present invention relates to 1,1,3-tri-substituted ureas which inhibit the extracellular release of inflammatory cytokines, said cytokines responsible for one or more human or higher mammalian disease states. The present invention further relates to compositions comprising said 1,1,3-tri-substituted ureas which inhibit the extracellular release of inflammatory cytokines, and methods for preventing, abating, or otherwise controlling enzymes which are understood to be the active components responsible for the herein described disease states.

63 Claims, No Drawings

TRI-SUBSTITUTED UREAS AS CYTOKINE INHIBITORS

CROSS REFERENCE TO RELATED APPLICATIONS

This application claims priority under Title 35, United States Code 119(e) from Provisional Application Ser. No. 60/564,745, filed Apr. 22, 2004.

FIELD OF THE INVENTION

The present invention relates to 1,1,3-tri-substituted ureas which inhibit the extracellular release of inflammatory cytokines, said cytokines responsible for one or more human or higher mammalian disease states. The present invention further relates to compositions comprising said N-1,1,3-tri-substituted ureas and methods for preventing, abating, or otherwise controlling enzymes which are understood to be the active components responsible for the herein described disease states.

DETAILED DESCRIPTION OF THE INVENTION

The present invention addresses several unmet medical needs, inter alia;
1) Providing pharmaceutical compositions capable of effectively blocking inflammatory cytokine production from cells, which thereby allows for the mitigation, alleviation, control, abatement, retardation, or prevention of one or more disease states or syndromes which are related to the extracellular release of one or more cytokines;
   a) Affecting the release of Interleukin-1 (IL-1): implicated as the molecule responsible for a large number of disease states, inter alia, rheumatoid arthritis, osteoarthritis, as well as other disease states which relate to connective tissue degradation;
   b) Affecting inducible Cycloxygenase-2 (COX-2) expression: inhibitors of cytokine release are proposed as inhibitors of inducible COX-2 expression, which has been shown to be increased by cytokines.
2) Providing pharmaceutical compositions which are efficacious in affecting the release of Tumor Necrosis Factor-α (TNF-α): This pro-inflammatory cytokine is suggested as an important mediator in many disease states or syndromes, inter alia, rheumatoid arthritis, osteoarthritis, inflammatory bowel disease (IBD), septic shock, cardiopulmonary dysfunction, acute respiratory disease, and cachexia.
3) Providing a pharmaceutical composition which is efficacious in providing analgesia, or otherwise relieving pain in humans and higher mammals.

These and other unmet medical needs are surprisingly resolved by the compounds of the present invention, which are capable of selectively affecting one or more disease states, conditions, or syndromes caused or affected by the extracellular release of cytokines.

Although each compound will not be effective against each and every disease state affected by the extracellular release of cytokines, nevertheless, the formulator is left to selecting the compound and make-up of a pharmaceutical composition used to treat the selected condition or illness non-limiting examples of which are described herein below.

The present invention relates to 1,1,3-tri-substituted ureas, for example, 1-(4-substituted and unsubstituted aryl)-1-(2-substituted-pyrimidin-4-yl)-3-aryl ureas, 1-(3-substituted aryl)-1-(2-substituted-pyrimidin-4-yl)-3-aryl ureas, 1-(2-substituted aryl)-1-(2-substituted-pyrimidin-4-yl)-3-aryl ureas, 1-(2,6-disubstituted substituted aryl)-1-(2-substituted-pyrimidin-4-yl)-3-aryl ureas, and the like which are suitable for mediating, controlling or otherwise inhibiting the extracellular release of certain cytokines, especially inflammatory cytokines, said cytokines playing a role in the stimulation, cause, or manifestation of a wide variety of diseases, disease states, or syndromes.

The following chemical hierarchy is used throughout the specification to particularly point out and distinctly claim the units which comprise the compounds of the present invention. The term "hydrocarbyl" stands for any carbon atom-based unit, said units optionally containing one or more organic functional groups, including inorganic atom comprising salts, inter alia, carboxylate salts, and quaternary ammonium salts. Encompassed within the term "hydrocarbyl" are the terms "acyclic" and "cyclic" units which divide hydrocarbyl units into cyclic and non-cyclic classes. Cyclic hydrocarbyl units include monocyclic, bicyclic, fused ring, and spirocyclic ring systems. Heterocyclic and heteroaryl units comprise one or more heteroatoms chosen from nitrogen, oxygen, sulfur, and combinations of these heteroatoms.

1. Substituted and unsubstituted $C_1$-$C_{10}$ acyclic hydrocarbyl: For the purposes of the present invention the term "substituted and unsubstituted $C_1$-$C_{10}$ acyclic hydrocarbyl" encompasses 3 categories of units:
   i) $C_1$-$C_{10}$ linear or branched alkyl, non-limiting examples of which includes, methyl ($C_1$), ethyl ($C_2$), n-propyl ($C_3$), iso-propyl ($C_3$), n-butyl ($C_4$), sec-butyl ($C_4$), iso-butyl ($C_4$), and tert-butyl ($C_4$); substituted $C_1$-$C_{10}$ linear or branched alkyl, non-limiting examples of which includes, hydroxymethyl ($C_1$), chloromethyl ($C_1$), trifluoromethyl ($C_1$), aminomethyl ($C_1$), 1-chloroethyl ($C_2$), 2-hydroxyethyl ($C_2$), 1,2-difluoroethyl ($C_2$), and 3-carboxypropyl ($C_3$).
   ii) $C_2$-$C_{10}$ linear or branched alkenyl, non-limiting examples of which includes, ethenyl ($C_2$), 3-propenyl ($C_3$), 1-propenyl (also 2-methylethenyl) ($C_3$), isopropenyl (also 2-methylethen-2-yl) ($C_3$), and buten-4-yl ($C_4$); substituted $C_2$-$C_{10}$ linear or branched alkenyl, non-limiting examples of which includes, 2-chloroethenyl (also 2-chlorovinyl) ($C_2$), 4-hydroxybuten-1-yl ($C_4$), 7-hydroxy-7-methyloct-4-en-2-yl ($C_9$), and 7-hydroxy-7-methylocta-3,5-dien-2-yl ($C_9$).
   iii) $C_2$-$C_{10}$ linear or branched alkynyl, non-limiting examples of which includes, ethynyl ($C_2$), prop-2-ynyl (also propargyl) ($C_3$), propyn-1-yl ($C_3$), and 2-methyl-hex-4-yn-1-yl ($C_7$); substituted $C_2$-$C_{10}$ linear or branched alkynyl, non-limiting examples of which includes, 5-hydroxy-5-methylhex-3-ynyl ($C_7$), 6-hydroxy-6-methylhept-3-yn-2-yl ($C_8$), and 5-hydroxy-5-ethylhept-3-ynyl ($C_9$).

2. Substituted and unsubstituted $C_1$-$C_{10}$ cyclic hydrocarbyl: For the purposes of the present invention the term "substituted and unsubstituted $C_1$-$C_{10}$ cyclic hydrocarbyl" encompasses 5 categories of units:
   i) $C_3$-$C_{10}$ carbocyclic units, non-limiting examples of which include, cyclopropyl ($C_3$), cyclobutyl ($C_4$), cyclopentyl ($C_5$), cyclohexyl ($C_6$), cycloheptyl ($C_7$), decalinyl ($C_{10}$), and decahydro-azulenyl ($C_{10}$); substituted $C_3$-$C_{10}$ carbocyclic units, non-limiting examples of which includes, 2-methylcyclopropyl ($C_3$), 2,5-dimethylcyclopentyl ($C_5$), 4-tert-butylcyclopentyl ($C_5$), 3,5-dichlorocyclohexyl ($C_6$), and 4-hydroxy-cyclohexyl ($C_6$).
   ii) $C_6$-$C_{10}$ aryl units which include, phenyl, naphthen-1-yl, and naphthen-2-yl; substituted $C_6$-$C_{10}$ aryl units, non-limiting examples of which includes, 4-fluorophenyl ($C_6$), 2,6-di-tert-butylphenyl ($C_6$), 3-hydroxyphenyl ($C_6$), 8-hydroxynaphthylen-2-yl ($C_{10}$), and 6-cyano-naphthylen-1-yl ($C_{10}$).

iii) $C_1$-$C_{10}$ heterocyclic units, which are heterocyclic units containing from 1 to 10 carbon atoms and one or more heteroatoms chosen from nitrogen, oxygen, sulfur, and mixtures thereof, non-limiting examples of which include, 1,2,3,4-tetrazolyl ($C_1$), aziridinyl ($C_2$), oxazolyl ($C_3$), tetrahydrofuranyl ($C_4$), dihydropyranyl ($C_5$), piperidin-2-one (valerolactam) ($C_5$), 2,3,4,5-tetrahydro-1H-azepinyl ($C_6$), 2,3-dihydro-1H-indole ($C_8$), and 1,2,3,4-tetrahydro-quinoline ($C_9$); substituted $C_1$-$C_{10}$ heterocyclic units, non-limiting examples of which include, 2-amino-4,5-dihydro-3H-pyrrolyl ($C_4$), N-methylmorpholinyl ($C_4$), 2,6-dimethylpiperazinyl ($C_4$), and, 1-aza-bicyclo[2.2.2]octane.

iv) $C_1$-$C_{10}$ heteroaryl units, which are heteroaryl units containing from 1 to 10 carbon atoms and one or more heteroatoms chosen from nitrogen, oxygen, sulfur, and mixtures thereof, non-limiting examples of which include, triazinyl ($C_3$), furanyl ($C_4$), thiophenyl ($C_4$), pyrimidinyl ($C_4$), pyridinyl ($C_5$), and 6,7-dihydro-5H-cyclopenta[b]pyridine ($C_8$); substituted $C_1$-$C_{10}$ heteroaryl units, non-limiting examples of which include, 4-dimethylaminopyridinyl ($C_5$) and 2-methylindolyl ($C_8$).

The substituted and unsubstituted $C_1$-$C_{10}$ cyclic hydrocarbyl units of the present invention can be bonded directly to the core pyrimidinyl-urea scaffold:

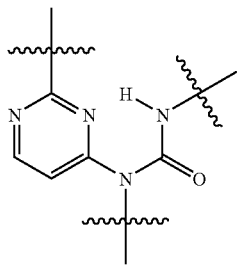

or they can be bonded to the core scaffold by way of a linking unit (tethered units) described herein below. Linked or tethered units include alkylenearyl units which are aryl units bonded to the core scaffold by way of an alkylene unit, for example, benzyl units having the formula:

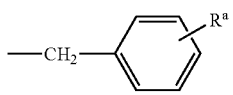

or alkyleneheteroaryl units for example a 2-picolyl unit having the formula:

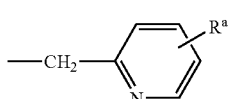

wherein $R^a$ represents one or more optional substitutions for the aryl ring hydrogen atoms. Non-limiting examples of substituted and unsubstituted $C_6$-$C_{10}$ alkylenearyl units include 2-methylbenzyl ($C_6$), 3-N,N-dimethylaminobenzyl ($C_6$), 4-fluorobenzyl ($C_6$), (8-hydroxy)naphthalen-2-ylmethyl ($C_{10}$), and 2-(3-hydroxy-phenyl)ethyl ($C_6$). Non-limiting examples of substituted and unsubstituted $C_1$-$C_{10}$ alkyleneheteroaryl units include piperidin-1-ylmethyl, piperidin-4-ylmethyl, tetrahydro-pyran-4-ylmethyl, morpholin-4-ylmethyl, isoquinolin-1-ylmethyl, and imidazolin-2-ylethyl. Non-limiting examples of $C_3$-$C_{10}$ alkylenecarbocyclic units include, cyclopropylmethyl ($C_3$), cyclopentylethyl ($C_5$), and cyclohexylmethyl ($C_6$).

The term "aryloyl" as it relates to the present invention are derivatives of aryl units bonded to a carbonyl unit, aryl units include benzene and naphthalene. A non-limiting example of an aryloyl unit is a substituted or unsubstituted benzoyl unit having the general formula:

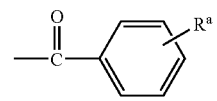

wherein $R^a$ represents one or more possible substitutions for a hydrogen atom. Heteroaryloyl units are units which are derived from heteroaryl units bonded to a carbonyl unit.

For the purposed of the present invention fused ring units, as well as spirocyclic rings, bicyclic rings and the like, which comprise a single heteroatom will be considered to belong to the cyclic family of the heteroatom containing ring. For example, 1,2,3,4-tetrahydroquinoline having the formula:

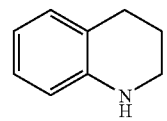

is, for the purposes of the present invention, considered a heterocyclic unit. 6,7-Dihydro-5H-[1]pyrindine having the formula:

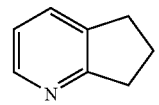

is, for the purposes of the present invention, considered a heteroaryl unit. When a fused ring unit contains heteroatoms in both a saturated and an aryl ring, the aryl ring will predominate and determine the type of category to which the ring is assigned. For example, 1,2,3,4-tetrahydro-[1,8]naphthyridine having the formula:

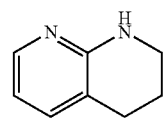

is, for the purposes of the present invention, considered a heteroaryl unit.

The term "substituted" is used throughout the specification. The term "substituted" is defined herein as "a hydrocarbyl moiety, whether acyclic or cyclic, which has one or more hydrogen atoms replaced by a substituent or several substituents as defined herein below. The units, which substituted for hydrogen atoms are capable of replacing one hydrogen atom, two hydrogen atoms, or three hydrogen atoms of a hydrocarbyl moiety at a time. In addition, these substituents can replace two hydrogen atoms on two adjacent carbons to form said substituent, new moiety or unit." For example, a substituted unit that requires a single hydrogen atom replacement includes halogen, hydroxyl, and the like. A two hydrogen atom replacement includes carbonyl, oximino, and the like. A two hydrogen atom replacement from adjacent carbon atoms includes epoxy, and the like. Three hydrogen replacement includes cyano, and the like. The term substituted is used throughout the present specification to indicate that a hydrocarbyl moiety, inter alia, aromatic ring, alkyl chain, can have one or more of the hydrogen atoms replaced by a substituent. When a moiety is described as "substituted" any number of the hydrogen atoms may be replaced. For example, 4-hydroxyphenyl is a "substituted aromatic carbocyclic ring", (N,N-dimethyl-5-amino)octanyl is a "substituted $C_8$ alkyl unit, 3-guanidinopropyl is a "substituted $C_3$ alkyl unit," and 2-carboxypyridinyl is a "substituted heteroaryl unit."

The following are non-limiting examples of units which can substitute for hydrogen atoms on a hydrocarbyl or other unit:

i) —$OR^8$;
ii) —$C(O)R^8$;
iii) —$C(O)OR^8$
iv) —$C(O)N(R^8)_2$;
v) —CN;
vi) —$N(R^8)_2$;
vii) —halogen;
viii) —$CF_3$, —$CCl_3$, —$CBr_3$; and
ix) —$SO_2R^8$ wherein each $R^8$ is independently hydrogen, substituted or unsubstituted $C_1$-$C_4$ linear, branched, or cyclic alkyl; or two $R^8$ units can be taken together to form a ring comprising from 3-7 atoms.

The compounds of the present invention are 1,1,3-tri-substituted ureas having the core scaffold:

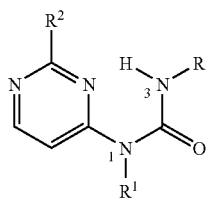

which comprises a first position nitrogen atom ($N^1$) and a third position nitrogen atom ($N^3$) on either side of a central carbonyl unit. To this core scaffold is attached at the first position nitrogen atom ($N^1$), a 2-substituted pyrimidin-4-yl unit bearing the $R^2$ units as the number 2 ring position substituent. Also attached to the first position nitrogen atom ($N^1$) is an $R^1$ unit as defined herein below. Attached to the third position nitrogen atom ($N^3$) is an R unit which is a unit as described herein below.

R units have the formula:

wherein $R^3$ is chosen from:
  i) substituted or unsubstituted $C_6$-$C_{10}$ aryl;
  ii) substituted or unsubstituted $C_1$-$C_{10}$ heteroaryl;
  iii) substituted or unsubstituted $C_3$-$C_{10}$ carbocyclic; or
  iv) substituted or unsubstituted $C_1$-$C_{10}$ heterocyclic.

The first category of R relates to the following aspects of $R^3$ when the linking unit L, as described herein below is absent (the index x is equal to 0).

The first category of $R^3$ units relates to substituted or unsubstituted $C_6$ aryl units, that is aryl units comprising from 6 carbon atoms, wherein said substitution is chosen from: halogen, $C_1$-$C_4$ linear or branched alkyl, —$OR^8$, —CN, —$N(R^8)_2$, —$CO_2R^8$, —$C(O)N(R^8)_2$, —$NR^8C(O)R^8$, —$NO_2$, and —$SR^8$; each $R^8$ is independently hydrogen, substituted or unsubstituted $C_1$-$C_4$ linear, branched, or cyclic alkyl; or two $R^8$ units can be taken together to form a ring comprising from 3-7 atoms.

The first aspect of $R^3$ as it applies to the first category of R, relates to substituted or unsubstituted $C_6$ aryl units, the first iteration of which includes units chosen from phenyl, 2-fluorophenyl, 3-fluorophenyl, 4-fluorophenyl, 2,3-difluorophenyl, 2,4-difluorophenyl, 2,5-difluorophenyl, 2,6-difluorophenyl, 3,4-difluorophenyl, 2,3,4-trifluorophenyl, 2,3,5-trifluorophenyl, 2,3,6-trifluorophenyl, 2,4,5-trifluorophenyl, 2,4,6-trifluorophenyl, 2-chlorophenyl, 3-chlorophenyl, 4-chlorophenyl, 2,3-dichlorophenyl, 2,4-dichlorophenyl, 2,5-dichlorophenyl, 2,6-dichlorophenyl, 3,4-dichlorophenyl, 2,3,4-trichlorophenyl, 2,3,5-trichlorophenyl, 2,3,6-trichlorophenyl, 2,4,5-trichlorophenyl, and 2,4,6-trichlorophenyl.

The second iteration of the first aspect of $R^3$ as it applies to the first category of R, relates to substituted $C_6$ aryl units which includes units chosen from 2-methylphenyl, 3-methylphenyl, 4-methylphenyl, 2,3-dimethylphenyl, 2,4-dimethylphenyl, 2,5-dimethylphenyl, 2,6-dimethylphenyl, 3,4-dimethylphenyl, 2,3,4-trimethylphenyl, 2,3,5-trimethylphenyl, 2,3,6-trimethylphenyl, 2,4,5-trimethylphenyl, 2,4,6-trimethylphenyl, 2-ethylphenyl, 3-ethylphenyl, 4-ethylphenyl, 2,3-diethylphenyl, 2,4-diethylphenyl, 2,5-diethylphenyl, 2,6-diethylphenyl, 3,4-diethylphenyl, 2,3,4-triethylphenyl, 2,3,5-triethylphenyl, 2,3,6-triethylphenyl, 2,4,5-triethylphenyl, and 2,4,6-triethylphenyl.

The third iteration of the first aspect of $R^3$ as it applies to the first category of R, relates to substituted $C_6$ aryl units, which includes units chosen from 2-hydroxyphenyl, 3-hydroxyphenyl, 4-hydroxyphenyl, 2,3-dihydroxy-phenyl, 2,4-dihydroxyphenyl, 2,5-dihydroxyphenyl, 2,6-dihydroxyphenyl, 3,4-dihydroxy-phenyl, 2,3,4-trihydroxyphenyl, 2,3,5-trihydroxyphenyl, 2,3,6-trihydroxyphenyl, 2,4,5-trihydroxyphenyl, and 2,4,6-trihydroxyphenyl.

The fourth iteration of the first aspect of $R^3$ as it applies to the first category of R, relates to substituted $C_6$ aryl units, which includes units chosen from 2-methoxyphenyl, 3-methoxyphenyl, 4-methoxyphenyl, 2,3-dimethoxyphenyl, 2,4-dimethoxyphenyl, 2,5-dimethoxyphenyl, 2,6-dimethoxyphenyl, 3,4-dimethoxyphenyl, 2,3,4-trimethoxyphenyl, 2,3,5-trimethoxyphenyl, 2,3,6-trimethoxyphenyl, 2,4,5-trimethoxyphenyl, and 2,4,6-trimethoxyphenyl.

The fifth iteration of the first aspect of $R^3$ as it applies to the first category of R, relates to substituted $C_6$ aryl units, which includes units chosen from 2-cyanophenyl, 3-cyanophenyl, 4-cyanophenyl, 2,3-dicyanophenyl, 2,4-dicyanophenyl, 2,5-dicyanophenyl, 2,6-dicyanophenyl, 3,4-dicyanophenyl, 2,3,4-tricyanophenyl, 2,3,5-tricyanophenyl, 2,3,6-tricyanophenyl, 2,4,5-tricyanophenyl, and 2,4,6-tricyanophenyl.

The sixth iteration of the first aspect of $R^3$ as it applies to the first category of R, relates to substituted $C_6$ aryl units, which includes units chosen from 2-nitrophenyl, 3-nitrophenyl, 4-nitrophenyl, 2,3-dinitrophenyl, 2,4-dinitrophenyl, 2,5-dinitrophenyl, 2,6-dinitrophenyl, 3,4-dinitrophenyl, 2,3,4-trinitrophenyl, 2,3,5-trinitrophenyl, 2,3,6-trinitrophenyl, 2,4,5-trinitrophenyl, and 2,4,6-trinitrophenyl.

The seventh iteration of the first aspect of $R^3$ as it applies to the first category of R, relates to substituted $C_6$ aryl units, which includes units chosen from 2,6-dimethyl-4-fluorophenyl, 2,6-dimethyl-3-fluorophenyl, 2,6-dimethyl-4-chlorophenyl, 2,6-di-tert-butyl-4-hydroxyphenyl, 2,6-difluoro-4-chlorophenyl, 2,6-difluoro-3-chlorophenyl, 2-hydroxy-4-methylphenyl, 2-hydroxy-5-methylphenyl, 2,6-dihydroxy-4-tert-butylphenyl, and 2,6-difluoro-4-cyanophenyl.

The eighth iteration of the first aspect of $R^3$ as it applies to the first category of R, relates to substituted $C_6$ aryl units, which includes units chosen from 3-dimethylaminophenyl, 4-dimethylaminophenyl, 3-diethylaminophenyl, 4-diethylaminophenyl, 3-methyl-sulfanylphenyl, 4-methylsulfanylphenyl, 3-ethylsulfanylphenyl, 4-ethylsulfanylphenyl, 3-propylsulfanylphenyl, and 4-propylsulfanylphenyl.

A ninth iteration of this aspect relates to $C_6$ aryl units substituted with a unit chosen from:
 i) —$CO_2R^8$,
 ii) —$N(R^8)_2$;
 iii) —$CON(R^8)_2$; and
 iv) —$NR^8COR^8$;

wherein $R^8$ is hydrogen, methyl, or ethyl. The units encompassing this iteration can also be substituted with a unit chosen from halogen, methyl, ethyl, —OH, —$OCH_3$, —$OC_2H_5$, and —CN.

The first group of the ninth iteration of the first aspect of $R^3$ as it applies to the first category of R, includes 2-carboxyphenyl, 3-carboxyphenyl, 4-carboxyphenyl, 2,4-dicarboxyphenyl, 2-carboxy-3-hydroxyphenyl, 2-carboxy-4-hydroxyphenyl, 3-carboxy-4-hydroxyphenyl, 2-hydroxy-4-carboxyphenyl, 2-carboxy-3-methoxyphenyl, 2-carboxy-4-methoxyphenyl, 3-carboxy-4-methoxyphenyl, and 2-methoxy-4-carboxyphenyl.

The second group of the ninth iteration of the first aspect of $R^3$ as it applies to the first category of R, includes 2-methylaminophenyl, 3-methylaminophenyl, 4-methylaminophenyl, 2,4-dimethylaminophenyl, 2-methylamino-3-hydroxyphenyl, 2-methylamino-4-hydroxyphenyl, 3-methylamino-4-hydroxyphenyl, 2-hydroxy-4-methylaminophenyl, 2-methylamino-3-methoxyphenyl, 2-methylamino-4-methoxyphenyl, 3-methylamino-4-methoxyphenyl, and 2-methoxy-4-methylaminophenyl.

The third group of the ninth iteration of the first aspect of $R^3$ as it applies to the first category of R, includes 2-N,N-dimethylaminophenyl, 3-N,N-dimethylaminophenyl, 2-N,N-diethylaminophenyl, 4-N,N-dimethylaminophenyl, 2-N,N-methylethylaminophenyl, 4-N,N-diethylaminophenyl, 2-hydroxy-4-N,N-dimethylaminophenyl, 2-methoxy-4-N,N-dimethylaminophenyl, and 2-methyl-4-N,N-dimethylaminophenyl.

The second aspect of $R^3$ as it applies to the first category of R, relates to substituted or unsubstituted $C_1$-$C_{10}$ heteroaryl units, the first iteration of which includes $C_5$ heteroaryl units chosen from pyridin-2-yl, pyridine-3-yl, pyridin-4-yl, and $C_4$ heteroaryl units chosen from furan-2-yl, furan-3-yl, thien-2-yl, and thien-3-yl.

The second iteration of the second aspect of $R^3$ as it applies to the first category of R, relates to $C_4$ heteroaryl units comprising more than one heteroatom, for example, units chosen from pyrimidin-2-yl, pyrimidin-4-yl, pyrimidin-5-yl, and morpholin-4-yl, and $C_3$ heteroaryl units comprising more than one heteroatom, for example, triazinyl.

The third aspect of $R^3$ relates to substituted or unsubstituted $C_3$-$C_7$ cycloalkyl units, the first iteration of which includes cyclopropyl, cyclobutyl, cyclopentyl, cyclohexyl, and cycloheptyl. A particular iteration includes cyclopropyl, methylcyclopropyl, and 2-methylcyclopentyl.

The second category of R units relates to R units which comprise an L unit which is a methylene unit (—$CH_2$—) wherein R has the formula —$CH_2$—$R^3$ and to the following aspects of $R^3$. This category of compounds therefore, when L is taken together with $R^3$ units, results in R units comprising benzyl and substituted benzyl units.

The first category of $R^3$ units which comprise the second category of R units relates to substituted or unsubstituted $C_6$ aryl units, that is aryl units comprising from 6 carbon atoms, wherein said substitution is chosen from: halogen, $C_1$-$C_4$ linear or branched alkyl, —$OR^8$, —CN, —$N(R)_2$, —$CO_2R^8$, —$C(O)N(R^8)_2$, —$NR^8C(O)R^8$, —$NO_2$, and —$SR^8$; each $R^8$ is independently hydrogen, substituted or unsubstituted $C_1$-$C_4$ linear, branched, or cyclic alkyl; or two $R^8$ units can be taken together to form a ring comprising from 3-7 atoms.

The first aspect of $R^3$ as it applies to the second category of R, relates to substituted or unsubstituted $C_6$ aryl units, the first iteration of which includes units chosen from phenyl, 2-fluorophenyl, 3-fluorophenyl, 4-fluorophenyl, 2,3-difluorophenyl, 2,4-difluorophenyl, 2,5-difluorophenyl, 2,6-difluorophenyl, 3,5-difluorophenyl, 2,3,4-trifluorophenyl, 2,3,5-trifluorophenyl, 2,3,6-trifluorophenyl, 2,4,5-trifluorophenyl, 2,4,6-trifluorophenyl, 2-chlorophenyl, 3-chlorophenyl, 4-chlorophenyl, 2,3-dichlorophenyl, 2,4-dichlorophenyl, 2,5-dichlorophenyl, 2,6-dichlorophenyl, 3,5-dichlorophenyl, 2,3,4-trichlorophenyl, 2,3,5-trichlorophenyl, 2,3,6-trichlorophenyl, 2,4,5-trichlorophenyl, and 2,4,6-trichlorophenyl.

The second iteration of the first aspect of $R^3$ as it applies to the second category of R, relates to substituted $C_6$ aryl units which includes units chosen from 2-methylphenyl, 3-methylphenyl, 4-methylphenyl, 2,3-dimethylphenyl, 2,4-dimethyl-phenyl, 2,5-dimethyl-phenyl, 2,6-dimethylphenyl, 3,5-dimethylphenyl, 2,3,4-trimethylphenyl, 2,3,5-trimethylphenyl, 2,3,6-trimethylphenyl, 2,4,5-trimethylphenyl, 2,4,6-trimethylphenyl, 2-ethylphenyl, 3-ethyl-phenyl, 4-ethylphenyl, 2,3-diethylphenyl, 2,4-diethylphenyl, 2,5-diethylphenyl, 2,6-diethylphenyl, 3,5-diethylphenyl, 2,3,4-triethylphenyl, 2,3,5-triethylphenyl, 2,3,6-triethylphenyl, 2,4,5-triethylphenyl, and 2,4,6-triethylphenyl.

The third iteration of the first aspect of $R^3$ as it applies to the second category of R, relates to substituted $C_6$ aryl units, which includes units chosen from 2-hydroxyphenyl, 3-hydroxyphenyl, 4-hydroxyphenyl, 2,3-dihydroxyphenyl, 2,4-dihydroxyphenyl, 2,5-dihydroxyphenyl, 2,6-dihydroxyphenyl, 3,5-dihydroxyphenyl, 2,3,4-trihydroxyphenyl, 2,3,5-trihydroxyphenyl, 2,3,6-trihydroxyphenyl, 2,4,5-trihydroxyphenyl, and 2,4,6-trihydroxyphenyl.

The fourth iteration of the first aspect of $R^3$ as it applies to the second category of R, relates to substituted $C_6$ aryl units, which includes units chosen from 2-methoxyphenyl, 3-methoxyphenyl, 4-methoxyphenyl, 2,3-dimethoxyphenyl, 2,4-dimethoxyphenyl, 2,5-dimethoxyphenyl, 3,5-dimethoxyphenyl, 2,6-dimethoxyphenyl, 2,3,4-trimethoxyphenyl, 2,3,5-trimethoxyphenyl, 2,3,6-trimethoxyphenyl, 2,4,5-trimethoxyphenyl, and 2,4,6-trimethoxyphenyl.

The fifth iteration of the first aspect of $R^3$ as it applies to the second category of R, relates to substituted $C_6$ aryl units, which includes units chosen from 2-cyanophenyl, 3-cyanophenyl, 4-cyanophenyl, 2,3-dicyanophenyl, 2,4-dicyanophenyl, 2,5-dicyanophenyl, 2,6-dicyanophenyl, 2,3,4-tricyanophenyl, 2,3,5-tricyanophenyl, 2,3,6-tricyanophenyl, 2,4,5-tricyanophenyl, and 2,4,6-tricyanophenyl.

The sixth iteration of the first aspect of $R^3$ as it applies to the second category of R, relates to substituted $C_6$ aryl units, which includes units chosen from 2-nitrophenyl, 3-nitrophenyl, 4-nitrophenyl, 2,3-dinitrophenyl, 2,4-dinitrophenyl, 2,5-dinitrophenyl, 2,6-dinitrophenyl, 2,3,4-trinitrophenyl, 2,3,5-trinitrophenyl, 2,3,6-trinitrophenyl, 2,4,5-trinitrophenyl, and 2,4,6-trinitrophenyl.

The seventh iteration of the first aspect of $R^3$ as it applies to the second category of R, relates to substituted $C_6$ aryl units, which includes units chosen from 2,6-dimethyl-4-fluorophenyl, 2,6-dimethyl-3-fluorophenyl, 2,6-dimethyl-4-chlorophenyl, 2,6-di-tert-butyl-4-hydroxyphenyl, 2,6-difluoro-4-chlorophenyl, 2,6-difluoro-3-chlorophenyl, 2-hydroxy-4-methylphenyl, 2-hydroxy-5-methylphenyl, 2,6-dihydroxy-4-tert-butylphenyl, and 2,6-difluoro-4-cyanophenyl.

The eighth iteration of the first aspect of $R^3$ as it applies to the second category of R, relates to substituted $C_6$ aryl units, which includes units chosen from 3-dimethylaminophenyl, 4-dimethylaminophenyl, 3-diethylaminophenyl, 4-diethylaminophenyl, 3-methylsulfanylphenyl, 4-methylsulfanylphenyl, 3-ethylsulfanylphenyl, 4-ethylsulfanylphenyl, 3-propylsulfanylphenyl, and 4-propylsulfanylphenyl.

A ninth iteration of this first aspect of $R^3$ as it relates to the second category of R relates to $C_6$ aryl units substituted with a unit chosen from:
i) —$CO_2R^8$;
ii) —$N(R^8)_2$;
iii) —$CON(R^8)_2$; and
iv) —$NR^8COR^8$;

wherein $R^8$ is hydrogen, methyl, or ethyl. The units encompassing this iteration can also be substituted with a unit chosen from halogen, methyl, ethyl, —OH, —$OCH_3$, —$OC_2H_5$, and —CN.

The first group of the ninth iteration of the first aspect of $R^3$ as it applies to the second category of R, includes 2-carboxyphenyl, 3-carboxyphenyl, 4-carboxyphenyl, 2,4-dicarboxyphenyl, 2-carboxy-3-hydroxyphenyl, 2-carboxy-4-hydroxyphenyl, 3-carboxy-4-hydroxyphenyl, 2-hydroxy-4-carboxyphenyl, 2-carboxy-3-methoxyphenyl, 2-carboxy-4-methoxyphenyl, 3-carboxy-4-methoxyphenyl, and 2-methoxy-4-carboxyphenyl.

The second group of the ninth iteration of the first aspect of $R^3$ as it applies to the second category of R, includes 2-methylaminophenyl, 3-methylaminophenyl, 4-methylaminophenyl, 2,4-dimethylaminophenyl, 2-methylamino-3-hydroxyphenyl, 2-methylamino-4-hydroxyphenyl, 3-methylamino-4-hydroxyphenyl, 2-hydroxy-4-methylaminophenyl, 2-methylamino-3-methoxyphenyl, 2-methylamino-4-methoxyphenyl, 3-methylamino-4-methoxyphenyl, and 2-methoxy-4-methylaminophenyl.

The third group of the ninth iteration of the first aspect of $R^3$ as it applies to the second category of R, includes 2-N,N-dimethylaminophenyl, 3-N,N-dimethylaminophenyl, 2-N,N-dimethylaminophenyl, 4-N,N-dimethylaminophenyl, 2-N,N-methylethylaminophenyl, 4-N,N-diethylaminophenyl, 2-hydroxy-4-N,N-dimethylaminophenyl, 2-methoxy-4-N,N-dimethylaminophenyl, and 2-methyl-4-N,N-dimethylaminophenyl.

The second aspect of $R^3$ as it applies to the second category of R, relates to substituted or unsubstituted $C_1$-$C_{10}$ heteroaryl units, the first iteration of which includes $C_5$ heteroaryl units chosen from 2-pyridinyl, 3-pyridinyl, 4-pyridinyl, and $C_4$ heteroaryl units chosen from 2-furanyl, and 2-thienyl.

The second iteration of the second aspect of $R^3$ as it applies to the second category of R, relates to $C_4$ heteroaryl units comprising more than one heteroatom, for example, units chosen from pyrimidin-2-yl, pyrimidin-4-yl, pyrimidin-5-yl, and morpholin-4-yl, and $C_3$ heteroaryl units comprising more than one heteroatom, for example, triazinyl.

$R^1$ has the formula:

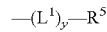

the index y is equal to 0 or 1, $R^5$ is a unit selected from the group consisting of:
i) substituted or unsubstituted $C_3$-$C_{10}$ carbocyclic;
ii) substituted or unsubstituted $C_6$-$C_{10}$ aryl;
iii) substituted or unsubstituted $C_1$-$C_{10}$ heterocyclic; and
iv) substituted or unsubstituted $C_1$-$C_{10}$ heteroaryl;

The first aspect of $R^5$ relates to substituted or unsubstituted $C_6$ aryl units, the first iteration of which relates to units chosen from phenyl, 2-fluorophenyl, 3-fluorophenyl, 4-fluorophenyl, 4-hydroxyphenyl, 4-methoxyphenyl, 4-ethoxyphenyl, 4-methylphenyl, 4-chlorophenyl, 4-methylsulfanylphenyl, and 4-dimethylaminophenyl.

The second aspect of $R^5$ relates to substituted or unsubstituted $C_3$, $C_4$ or $C_5$ heterocyclic units, the first iteration of which relates to substituted and unsubstituted 6-member rings chosen from piperazine, piperidine, morpholine, and tetrahydropyran. The second iteration of this aspect of $R^5$ relates to 5-member rings chosen from tetrahydrofuran, pyrrolidine, and imidazolidine. The $C_3$, $C_4$ or $C_5$ heterocyclic units can be bonded to the core structure by any ring atom, for example, tetrahydrofuran-2-yl, tetrahydrofuran-3-yl, pyrrolidin-2-yl, pyrrolidin-3-yl, imidazolidine-2-yl, imidazolidine-4-yl, imidazolidine-5-yl, piperazine-1-yl, piperazine-2-yl, piperidine-1-yl, piperidine-2-yl, piperidine-3-yl, piperidine-4-yl, morpholin-4-yl, and tetrahydropyran-4-yl.

$R^2$ has the formula:

the index z is equal to 0 or 1, $R^6$ is a unit selected from the group consisting of:
i) hydrogen;
ii) substituted or unsubstituted $C_1$-$C_{10}$ linear or branched hydrocarbyl;
iii) substituted or unsubstituted $C_3$-$C_{10}$ carbocyclic;
iv) substituted or unsubstituted $C_6$-$C_{10}$ aryl;
v) substituted or unsubstituted $C_1$-$C_{10}$ heterocyclic; and
vi) substituted or unsubstituted $C_1$-$C_{10}$ heteroaryl.

The first Category of $R^2$ relates to units which are units having an amino linking unit —NH—, said $R^2$ units having the formula:

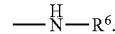

The first aspect of $R^6$ as it relates to the first category of $R^2$, includes substituted or unsubstituted $C_1$-$C_{10}$ linear or branched hydrocarbyl, the first iteration of which includes alkyl units chosen from 1(S)-2-hydroxy-1,2-dimethylpropyl, 1(S)-2-methoxy-1-methylethyl, 1(S)-sec-butyl, and iso-propyl.

The second aspect of $R^6$ relates to substituted or unsubstituted tethered $C_6$ aryl, the first iteration of which is substituted and unsubstituted phenyl and benzyl (when $R^6$ comprises a tethered cyclic hydrocarbyl). Non-limiting examples of $R^2$ units include benzyl and (1S)-phenylethyl when $L^2$ is —NH—.

The third aspect of $R^6$ as it relates to the first category of $R^2$, includes $C_1$-$C_{10}$ substituted or unsubstituted heterocycles, the first iteration of which is a substituted or unsubstituted $C_4$ or C₅ heterocyclic unit chosen from piperidin-1-yl, piperidin-4-yl, tetrahydropyran-4-yl, and morpholin-4-yl. The second iteration of this aspect relates to substituted or unsubstituted C₄ or C₅ heterocyclic unit tethered to the amino linking unit, —NH—, by way of a methylene unit, —CH₂—; non-limiting examples of this iteration are chosen from piperidin-1-ylmethyl, piperidin-4-ylmethyl, tetrahydropyran-4-ylmethyl, and morpholin-4-ylmethyl.

L, L¹, and L² are linking groups each of which are independently selected from the group consisting of:
 i) —C(R⁷)₂—;
 ii) —NR⁷—; and
 iii) —O—;

R⁷ is hydrogen, C₁-C₄ alkyl; or two R⁷ units can be taken together to form a carbonyl unit, and the indices x, y, or z are 0 or 1. When x, y, or z is equal to 0 the linking group is absent, when x, y, or z is equal to 1 the linking group is present.

When L is a carbonyl unit and R³ comprises a substituted or unsubstituted C₆ aryl unit, then R is an aryloyl unit as defined herein above.

The first aspect of L relates to compounds wherein L is chosen from —C(O)—, —CH₂— and —NH—. A first iteration of this aspect of L relates to Category I—first aspect; first, second, and third iterations wherein methylene, —CH₂—, is used to link R³ units which are substituted and unsubstituted C₆ aryl units with the core urea scaffold thereby providing R units which are benzyl or substituted benzyl units.

The first aspect of L² relates to compounds wherein L² is chosen from —C(O)—, —CH₂— or —NH—. A first iteration of this aspect of L² relates to Category I—first aspect; first, second, and third iterations wherein —NH— is used to link R⁶ units which are substituted or unsubstituted C₁-C₁₀ linear or branched hydrocarbyl units with the core 1,1,3-trisubstituted urea scaffold. One non-limiting example of these R⁶ units includes a unit chosen from 1(S)-2-hydroxy-1,2-dimethylpropyl, 1(S)-2-methoxy-1-methylethyl, 1(S)-sec-butyl, and isopropyl thereby providing an R² chosen from a unit chosen from 1(S)-2-hydroxy-1,2-dimethylpropylamino, 1(S)-2-methoxy-1-methylethylamino, 1(S)-sec-butylamino, and isopropylamino.

A second aspect of L² relates to —NH— units used to link heterocyclic and heterocyclic units tethered with a methylene unit, non-limiting examples of which include piperidin-1-yl, piperidin-1-ylmethyl, piperidin-4-yl, tetrahydropyran-4-yl, tetrahydro-pyran-4-ylmethyl, morpholin-4-yl, and morpholin-4-ylmethyl.

The analogs (compounds) of the present invention are arranged into several categories to assist the formulator in applying a rational synthetic strategy for the preparation of analogs which are not expressly exampled herein. The arrangement into categories does not imply increased or decreased efficacy for any of the compositions of matter described herein.

The compounds which comprise Category I of the present invention are N-[(2-substituted-pyrimidin-4-yl)-(substituted or unsubstituted-phenyl)]-N'-aryl-ureas having the formula:

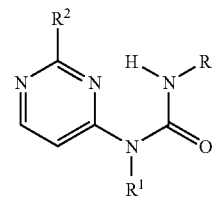

the first aspect of which relates to R² units which are substituted amines.

The first aspect of Category I relates to 1-(4-substituted and unsubstituted aryl)-1-(2-substituted-pyrimidin-4-yl)-3-aryl ureas having the formula:

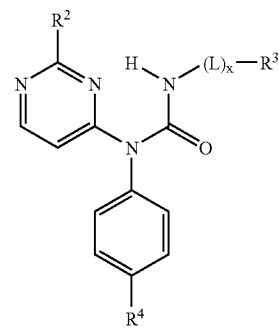

the first iteration of which has the formula:

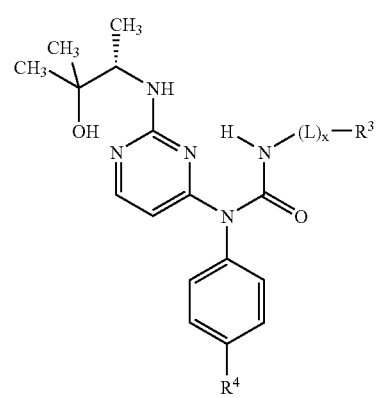

wherein non-limiting examples of L, R³, and R⁴ are defined herein below in Table I. In Table I, compounds 1-100 have x equal to 0; for compounds 101-200 x is equal to 1 and the L unit is defined therein.

TABLE I

| No. | R⁴ | R³ | No. | R⁴ | L | R³ |
|-----|-----|-----|-----|-----|-----|-----|
| 1 | —H | 2-fluorophenyl | 101 | —H | —CH₂— | 2-fluorophenyl |
| 2 | —H | 3-fluorophenyl | 102 | —H | —CH₂— | 3-fluorophenyl |
| 3 | —H | 4-fluorophenyl | 103 | —H | —CH₂— | 4-fluorophenyl |
| 4 | —H | 2,6-difluorophenyl | 104 | —H | —CH₂— | 2,6-difluorophenyl |
| 5 | —H | 2-chlorophenyl | 105 | —H | —CH₂— | 2-chlorophenyl |
| 6 | —H | 3-chlorophenyl | 106 | —H | —CH₂— | 3-chlorophenyl |

TABLE I-continued

| No. | R⁴ | R³ | No. | R⁴ | L | R³ |
|---|---|---|---|---|---|---|
| 7 | —H | 4-chlorophenyl | 107 | —H | —CH₂— | 4-chlorophenyl |
| 8 | —H | 3,4-dichlorophenyl | 108 | —H | —CH₂— | 3,4-dichlorophenyl |
| 9 | —H | 2,4-dichlorophenyl | 109 | —H | —CH₂— | 2,4-dichlorophenyl |
| 10 | —H | 2,6-dichlorophenyl | 110 | —H | —CH₂— | 2,6-dichlorophenyl |
| 11 | —H | 2-methylphenyl | 111 | —H | —CH₂— | 2-methylphenyl |
| 12 | —H | 3-methylphenyl | 112 | —H | —CH₂— | 3-methylphenyl |
| 13 | —H | 4-methylphenyl | 113 | —H | —CH₂— | 4-methylphenyl |
| 14 | —H | 2,4-dimethylphenyl | 114 | —H | —CH₂— | 2,4-dimethylphenyl |
| 15 | —H | 2,6-dimethylphenyl | 115 | —H | —CH₂— | 2,6-dimethylphenyl |
| 16 | —H | 2-methoxyphenyl | 116 | —H | —CH₂— | 2-methoxyphenyl |
| 17 | —H | 3-methoxyphenyl | 117 | —H | —CH₂— | 3-methoxyphenyl |
| 18 | —H | 4-methoxyphenyl | 118 | —H | —CH₂— | 4-methoxyphenyl |
| 19 | —H | 3-(CF₃)-phenyl | 119 | —H | —CH₂— | 3-(CF₃)-phenyl |
| 20 | —H | 4-(CF₃)-phenyl | 120 | —H | —CH₂— | 4-(CF₃)-phenyl |
| 21 | —F | 2-fluorophenyl | 121 | —F | —CH₂— | 2-fluorophenyl |
| 22 | —F | 3-fluorophenyl | 122 | —F | —CH₂— | 3-fluorophenyl |
| 23 | —F | 4-fluorophenyl | 123 | —F | —CH₂— | 4-fluorophenyl |
| 24 | —F | 2,6-difluorophenyl | 124 | —F | —CH₂— | 2,6-difluorophenyl |
| 25 | —F | 2-chlorophenyl | 125 | —F | —CH₂— | 2-chlorophenyl |
| 26 | —F | 3-chlorophenyl | 126 | —F | —CH₂— | 3-chlorophenyl |
| 27 | —F | 4-chlorophenyl | 127 | —F | —CH₂— | 4-chlorophenyl |
| 28 | —F | 3,4-dichlorophenyl | 128 | —F | —CH₂— | 3,4-dichlorophenyl |
| 29 | —F | 2,4-dichlorophenyl | 129 | —F | —CH₂— | 2,4-dichlorophenyl |
| 30 | —F | 2,6-dichlorophenyl | 130 | —F | —CH₂— | 2,6-dichlorophenyl |
| 31 | —F | 2-methylphenyl | 131 | —F | —CH₂— | 2-methylphenyl |
| 32 | —F | 3-methylphenyl | 132 | —F | —CH₂— | 3-methylphenyl |
| 33 | —F | 4-methylphenyl | 133 | —F | —CH₂— | 4-methylphenyl |
| 34 | —F | 2,4-dimethylphenyl | 134 | —F | —CH₂— | 2,4-dimethylphenyl |
| 35 | —F | 2,6-dimethylphenyl | 135 | —F | —CH₂— | 2,6-dimethylphenyl |
| 36 | —F | 2-methoxyphenyl | 136 | —F | —CH₂— | 2-methoxyphenyl |
| 37 | —F | 3-methoxyphenyl | 137 | —F | —CH₂— | 3-methoxyphenyl |
| 38 | —F | 4-methoxyphenyl | 138 | —F | —CH₂— | 4-methoxyphenyl |
| 39 | —F | 3-(CF₃)-phenyl | 139 | —F | —CH₂— | 3-(CF₃)-phenyl |
| 40 | —F | 4-(CF₃)-phenyl | 140 | —F | —CH₂— | 4-(CF₃)-phenyl |
| 41 | —CH₃ | 2-fluorophenyl | 141 | —CH₃ | —CH₂— | 2-fluorophenyl |
| 42 | —CH₃ | 3-fluorophenyl | 142 | —CH₃ | —CH₂— | 3-fluorophenyl |
| 43 | —CH₃ | 4-fluorophenyl | 143 | —CH₃ | —CH₂— | 4-fluorophenyl |
| 44 | —CH₃ | 2,6-difluorophenyl | 144 | —CH₃ | —CH₂— | 2,6-difluorophenyl |
| 45 | —CH₃ | 2-chlorophenyl | 145 | —CH₃ | —CH₂— | 2-chlorophenyl |
| 46 | —CH₃ | 3-chlorophenyl | 146 | —CH₃ | —CH₂— | 3-chlorophenyl |
| 47 | —CH₃ | 4-chlorophenyl | 147 | —CH₃ | —CH₂— | 4-chlorophenyl |
| 48 | —CH₃ | 3,4-dichlorophenyl | 148 | —CH₃ | —CH₂— | 3,4-dichlorophenyl |
| 49 | —CH₃ | 2,4-dichlorophenyl | 149 | —CH₃ | —CH₂— | 2,4-dichlorophenyl |
| 50 | —CH₃ | 2,6-dichlorophenyl | 150 | —CH₃ | —CH₂— | 2,6-dichlorophenyl |
| 51 | —CH₃ | 2-methylphenyl | 151 | —CH₃ | —CH₂— | 2-methylphenyl |
| 52 | —CH₃ | 3-methylphenyl | 152 | —CH₃ | —CH₂— | 3-methylphenyl |
| 53 | —CH₃ | 4-methylphenyl | 153 | —CH₃ | —CH₂— | 4-methylphenyl |
| 54 | —CH₃ | 2,4-dimethylphenyl | 154 | —CH₃ | —CH₂— | 2,4-dimethylphenyl |
| 55 | —CH₃ | 2,6-dimethylphenyl | 155 | —CH₃ | —CH₂— | 2,6-dimethylphenyl |
| 56 | —CH₃ | 2-methoxyphenyl | 156 | —CH₃ | —CH₂— | 2-methoxyphenyl |
| 57 | —CH₃ | 3-methoxyphenyl | 157 | —CH₃ | —CH₂— | 3-methoxyphenyl |
| 58 | —CH₃ | 4-methoxyphenyl | 158 | —CH₃ | —CH₂— | 4-methoxyphenyl |
| 59 | —CH₃ | 3-(CF₃)-phenyl | 159 | —CH₃ | —CH₂— | 3-(CF₃)-phenyl |
| 60 | —CH₃ | 4-(CF₃)-phenyl | 160 | —CH₃ | —CH₂— | 4-(CF₃)-phenyl |
| 61 | —OCH₃ | 2-fluorophenyl | 161 | —OCH₃ | —CH₂— | 2-fluorophenyl |
| 62 | —OCH₃ | 3-fluorophenyl | 162 | —OCH₃ | —CH₂— | 3-fluorophenyl |
| 63 | —OCH₃ | 4-fluorophenyl | 163 | —OCH₃ | —CH₂— | 4-fluorophenyl |
| 64 | —OCH₃ | 2,6-difluorophenyl | 164 | —OCH₃ | —CH₂— | 2,6-difluorophenyl |
| 65 | —OCH₃ | 2-chlorophenyl | 165 | —OCH₃ | —CH₂— | 2-chlorophenyl |
| 66 | —OCH₃ | 3-chlorophenyl | 166 | —OCH₃ | —CH₂— | 3-chlorophenyl |
| 67 | —OCH₃ | 4-chlorophenyl | 167 | —OCH₃ | —CH₂— | 4-chlorophenyl |
| 68 | —OCH₃ | 3,4-dichlorophenyl | 168 | —OCH₃ | —CH₂— | 3,4-dichlorophenyl |
| 69 | —OCH₃ | 2,4-dichlorophenyl | 169 | —OCH₃ | —CH₂— | 2,4-dichlorophenyl |
| 70 | —OCH₃ | 2,6-dichlorophenyl | 170 | —OCH₃ | —CH₂— | 2,6-dichlorophenyl |
| 71 | —OCH₃ | 2-methylphenyl | 171 | —OCH₃ | —CH₂— | 2-methylphenyl |
| 72 | —OCH₃ | 3-methylphenyl | 172 | —OCH₃ | —CH₂— | 3-methylphenyl |
| 73 | —OCH₃ | 4-methylphenyl | 173 | —OCH₃ | —CH₂— | 4-methylphenyl |
| 74 | —OCH₃ | 2,4-dimethylphenyl | 174 | —OCH₃ | —CH₂— | 2,4-dimethylphenyl |
| 75 | —OCH₃ | 2,6-dimethylphenyl | 175 | —OCH₃ | —CH₂— | 2,6-dimethylphenyl |
| 76 | —OCH₃ | 2-methoxyphenyl | 176 | —OCH₃ | —CH₂— | 2-methoxyphenyl |
| 77 | —OCH₃ | 3-methoxyphenyl | 177 | —OCH₃ | —CH₂— | 3-methoxyphenyl |
| 78 | —OCH₃ | 4-methoxyphenyl | 178 | —OCH₃ | —CH₂— | 4-methoxyphenyl |
| 79 | —OCH₃ | 3-(CF₃)-phenyl | 179 | —OCH₃ | —CH₂— | 3-(CF₃)-phenyl |
| 80 | —OCH₃ | 4-(CF₃)-phenyl | 180 | —OCH₃ | —CH₂— | 4-(CF₃)-phenyl |
| 81 | —SCH₃ | 2-fluorophenyl | 181 | —SCH₃ | —CH₂— | 2-fluorophenyl |
| 82 | —SCH₃ | 3-fluorophenyl | 182 | —SCH₃ | —CH₂— | 3-fluorophenyl |
| 83 | —SCH₃ | 4-fluorophenyl | 183 | —SCH₃ | —CH₂— | 4-fluorophenyl |

TABLE I-continued

| No. | R⁴ | R³ | No. | R⁴ | L | R³ |
|---|---|---|---|---|---|---|
| 84 | —SCH₃ | 2,6-difluorophenyl | 184 | —SCH₃ | —CH₂— | 2,6-difluorophenyl |
| 85 | —SCH₃ | 2-chlorophenyl | 185 | —SCH₃ | —CH₂— | 2-chlorophenyl |
| 86 | —SCH₃ | 3-chlorophenyl | 186 | —SCH₃ | —CH₂— | 3-chlorophenyl |
| 87 | —SCH₃ | 4-chlorophenyl | 187 | —SCH₃ | —CH₂— | 4-chlorophenyl |
| 88 | —SCH₃ | 3,4-dichlorophenyl | 188 | —SCH₃ | —CH₂— | 3,4-dichlorophenyl |
| 89 | —SCH₃ | 2,4-dichlorophenyl | 189 | —SCH₃ | —CH₂— | 2,4-dichlorophenyl |
| 90 | —SCH₃ | 2,6-dichlorophenyl | 190 | —SCH₃ | —CH₂— | 2,6-dichlorophenyl |
| 91 | —SCH₃ | 2-methylphenyl | 191 | —SCH₃ | —CH₂— | 2-methylphenyl |
| 92 | —SCH₃ | 3-methylphenyl | 192 | —SCH₃ | —CH₂— | 3-methylphenyl |
| 93 | —SCH₃ | 4-methylphenyl | 193 | —SCH₃ | —CH₂— | 4-methylphenyl |
| 94 | —SCH₃ | 2,4-dimethylphenyl | 194 | —SCH₃ | —CH₂— | 2,4-dimethylphenyl |
| 95 | —SCH₃ | 2,6-dimethylphenyl | 195 | —SCH₃ | —CH₂— | 2,6-dimethylphenyl |
| 96 | —SCH₃ | 2-methoxyphenyl | 196 | —SCH₃ | —CH₂— | 2-methoxyphenyl |
| 97 | —SCH₃ | 3-methoxyphenyl | 197 | —SCH₃ | —CH₂— | 3-methoxyphenyl |
| 98 | —SCH₃ | 4-methoxyphenyl | 198 | —SCH₃ | —CH₂— | 4-methoxyphenyl |
| 99 | —SCH₃ | 3-(CF₃)-phenyl | 199 | —SCH₃ | —CH₂— | 3-(CF₃)-phenyl |
| 100 | —SCH₃ | 4-(CF₃)-phenyl | 200 | —SCH₃ | —CH₂— | 4-(CF₃)-phenyl |

The following are further non-limiting examples of compounds which comprise the first iteration of the first aspect of Category I according to the present invention.

1-(4-Fluorophenyl)-1-{2-[(1S)-2-hydroxy-1,2-dimethylpropylamino]-pyrimidin-4-yl}-3-o-tolyl-urea: $^1$H NMR (300 MHz, CDCl$_3$) δ 7.96 (br s, 1H), 7.92 (d, J=5.8 Hz, 1H), 7.29-7.18 (m, 8H), 5.66 (br s, 1H), 4.00 (m, 1H), 2.42 (s, 3H), 1.28 (s, 3H), 1.24 (d, J=6.9 Hz, 3H), 1.23 (s, 3H); MS (ESI) m/z 424 (M+1).

1-(4-Fluorophenyl)-1-{2-[(1S)-2-hydroxy-1,2-dimethylpropylamino]-pyrimidin-4-yl}-3-(2,6-dichlorophenyl)-urea: $^1$H NMR (300 MHz, CDCl$_3$) δ 7.95 (d, J=5.8 Hz, 1H), 7.40-7.13 (m, 7H), 5.57 (d, J=5.8 Hz, 1H), 5.28 (br s, 1H), 4.02 (m, 1H), 1.24 (s, 3H), 1.22 (d, J=6.9 Hz, 3H), 1.20 (s, 3H); MS (ESI) m/z 478 (M+1).

1-(4-Methoxyphenyl)-1-{2-[(1S)-2-hydroxy-1,2-dimethylpropylamino]-pyrimidin-4-yl}-3-o-tolyl-urea: $^1$H NMR (300 MHz, CDCl$_3$) δ 8.05 (br s, 1H), 7.91 (d, J=5.8 Hz, 1H), 7.21-7.00 (m, 3H), 7.18 (d, J=8.9 Hz, 2H), 7.02 (d, J=8.9 Hz, 2H), 5.68 (m, 1H), 5.30 (br s, 1H), 4.01 (m, 1H), 3.85 (s, 3H), 2.43 (s, 3H), 1.28 (s, 3H), 1.24 (d, J=6.9 Hz, 3H), 1.23 (s, 3H); MS (ESI) m/z 436 (M+1).

1-(4-Methoxyphenyl)-1-{2-[(1S)-2-hydroxy-1,2-dimethyl-propylamino]-pyrimidin-4-yl}-3-(2-chlorophenyl)-urea: $^1$H NMR (300 MHz, CDCl$_3$) δ 13.04 (br s, 1H), 8.41 (d, J=8.0 Hz, 1H), 7.92 (d, J=6.0 Hz, 1H), 7.37-7.16 (m, 4H), 7.17 (d, J=8.9 Hz, 2H), 7.02 (d, J=8.9 Hz, 2H), 5.56 (m, 2H), 4.05 (m, 1H), 3.85 (s, 3H), 1.30 (s, 3H), 1.25 (d, J=6.9 Hz, 3H), 1.23 (s, 3H); MS (ESI) m/z 456 (M+1).

1-Phenyl-1-{2-[(1S)-2-hydroxy-1,2-dimethylpropylamino]-pyrimidin-4-yl}-3-(2-chlorophenyl)-urea: $^1$H NMR (300 MHz, CD$_3$OD) δ 8.19 (m, 1H), 7.98 (d, J=6.0 Hz, 1H), 7.59-7.49 (m, 4H), 7.37-7.32 (m, 3H), 7.22-7.03 (m, 1H), 5.42-5.39 (m, 1H), 4.30-3.98 (m, 1H), 1.31-1.22 (m, 9H); MS (ESI) m/z 426 (M+1).

1-(4-Fluorophenyl)-1-{2-[(1S)-2-hydroxy-1,2-dimethylpropylamino]-pyrimidin-4-yl}-3-(2-chlorophenyl)-urea: $^1$H NMR (300 MHz, CDCl$_3$) δ 13.05 (s, 1H), 8.38 (d, J=8.2 Hz, 1H), 7.95 (d, J=5.8 Hz, 1H), 7.40 (d, J=8.0 Hz, 1H), 7.29-7.17 (m, 5H), 7.01 (dd, J=7.9, 7.5 Hz, 1H), 5.53 (d, J=8.4 Hz, 1H), 5.47 (d, J=5.8 Hz, 1H), 4.15-4.01 (m, 1H), 1.31 (s, 3H), 1.26 (d, J=6.8 Hz, 3H), 1.25 (s, 3H); $^{13}$C (75 MHz, CDCl$_3$) δ 161.5, 160.7, 160.0, 158.2, 152.6, 136.0, 134.6, 131.3, 129.1, 127.8, 124.0, 121.8, 117.1, 116.8, 99.2, 73.3, 55.5, 28.0, 25.1, 16.4; MS (ESI) m/z 444 (M+1).

1-(4-Methoxyphenyl)-1-{2-[(1S)-2-hydroxy-1,2-dimethylpropylamino]-pyrimidin-4-yl}-3-(2-methoxybenzyl)-urea: $^1$H NMR (300 MHz, CDCl$_3$) δ 7.86 (d, J=5.9 Hz, 1H), 7.41 (d, J=7.3 Hz, 1H), 7.14 (d, J=8.9 Hz, 2H), 7.02-6.88 (m, 5H), 5.63 (br s, 1H), 5.10 (br s, 1H), 4.59 (d, J=5.4 Hz, 2H), 3.92 (s, 3H), 3.87 (s, 4H), 1.29-1.19 (m, 9H); MS (ESI) m/z 466 (M+1).

1-(4-Methoxyphenyl)-1-{2-[(1S)-2-hydroxy-1,2-dimethyl-propylamino]-pyrimidin-4-yl}-3-(2-chlorobenzyl)-urea: $^1$H NMR (300 MHz, CDCl$_3$) δ 7.87 (d, J=5.9 Hz, 1H), 7.54 (m, 1H), 7.42 (m, 1H), 7.29-7.23 (m, 2H), 7.14 (d, J=8.8 Hz, 2H), 7.00 (d, J=8.8 Hz, 2H), 5.54 (d, J=5.9 Hz, 1H), 5.18 (br d, J=7.1 Hz, 1H), 4.68 (d, J=5.9 Hz, 2H), 4.03-3.85 (m, 1H), 3.86 (s, 3H), 1.27 (s, 3H), 1.22 (s, 3H), 1.21 (br d, 3H); MS (ESI) m/z 470 (M+1).

1-(4-Methoxyphenyl)-1-{2-[(1S)-2-hydroxy-1,2-dimethylpropylamino]-pyrimidin-4-yl}-3-(2-fluorobenzyl)-urea: $^1$H NMR (300 MHz, CDCl$_3$) δ 7.88 (d, J=6.0 Hz, 1H), 7.50 (t, J=7.5 Hz, 1H), 7.33-7.29 (m, 2H), 7.19-7.08 (m, 3H), 7.02 (d, J=9.1 Hz, 2H), 5.57 (d, J=5.9 Hz, 1H), 5.34 (br s, 1H), 4.66 (d, J=5.7 Hz, 2H), 3.88 (s, 4H), 3.44 (s, 5H), 1.29-1.23 (m, 9H); MS (ESI) m/z 454 (M+1).

1-(4-Fluorophenyl)-1-{2-[(1S)-2-hydroxy-1,2-dimethylpropylamino]-pyrimidin-4-yl}-3-(2-chlorobenzyl)-urea: $^1$H NMR (300 MHz, CDCl$_3$) δ 7.88 (d, J=6.0 Hz, 1H), 7.54-7.50 (m, 1H), 7.45-7.41 (m, 1H), 7.30-7.27 (m, 2H), 7.21-7.10 (m, 4H), 5.50 (d, J=4.8 Hz, 1H), 4.68 (d, J=5.7 Hz, 2H), 3.91 (br s, 1H), 1.27-1.20 (m, 9H); MS (ESI) m/z 458 (M+1).

Further non-limiting examples of the first iteration of the first aspect of Category I wherein the index x equals 0 includes:

1-Phenyl-1-{2-[(1S)-2-hydroxy-1,2-dimethyl-propylamino]-pyrimidin-4-yl}-3-o-tolyl-urea;

1-Phenyl-1-{2-[(1S)-2-hydroxy-1,2-dimethyl-propylamino]-pyrimidin-4-yl}-3-m-tolyl-urea;

1-Phenyl-1-{2-[(1S)-2-hydroxy-1,2-dimethyl-propylamino]-pyrimidin-4-yl}-3-p-tolyl-urea;

1-Phenyl-1-{2-[(1S)-2-hydroxy-1,2-dimethyl-propylamino]-pyrimidin-4-yl}-3-(2-fluorophenyl)-urea;

1-Phenyl-1-{2-[(1S)-2-hydroxy-1,2-dimethyl-propylamino]-pyrimidin-4-yl}-3-(3-fluorophenyl)-urea;

1-Phenyl-1-{2-[(1S)-2-hydroxy-1,2-dimethyl-propylamino]-pyrimidin-4-yl}-3-(4-phenyl)-urea;

1-Phenyl-1-{2-[(1S)-2-hydroxy-1,2-dimethyl-propylamino]-pyrimidin-4-yl}-3-(2,3-difluorophenyl)-urea;

1-Phenyl-1-{2-[(1S)-2-hydroxy-1,2-dimethyl-propylamino]-pyrimidin-4-yl}-3-(2,4-difluorophenyl)-urea;
1-Phenyl-1-{2-[(1S)-2-hydroxy-1,2-dimethyl-propylamino]-pyrimidin-4-yl}-3-(2,5-difluorophenyl)-urea;
1-Phenyl-1-{2-[(1S)-2-hydroxy-1,2-dimethyl-propylamino]-pyrimidin-4-yl}-3-(2,6-difluorophenyl)-urea;
1-Phenyl-1-{2-[(1S)-2-hydroxy-1,2-dimethyl-propylamino]-pyrimidin-4-yl}-3-(2,3,4-trifluorophenyl)-urea;
1-Phenyl-1-{2-[(1S)-2-hydroxy-1,2-dimethyl-propylamino]-pyrimidin-4-yl}-3-(2,3,5-trifluorophenyl)-urea;
1-Phenyl-1-{2-[(1S)-2-hydroxy-1,2-dimethyl-propylamino]-pyrimidin-4-yl}-3-(2,3,6-trifluorophenyl)-urea;
1-Phenyl-1-{2-[(1S)-2-hydroxy-1,2-dimethyl-propylamino]-pyrimidin-4-yl}-3-(2,4,5-trifluorophenyl)-urea;
1-Phenyl-1-{2-[(1S)-2-hydroxy-1,2-dimethyl-propylamino]-pyrimidin-4-yl}-3-(2,4,6-trifluorophenyl)-urea;
1-Phenyl-1-{2-[(1S)-2-hydroxy-1,2-dimethyl-propylamino]-pyrimidin-4-yl}-3-(3-chlorophenyl)-urea;
1-Phenyl-1-{2-[(1S)-2-hydroxy-1,2-dimethyl-propylamino]-pyrimidin-4-yl}-3-(4-chlorophenyl)-urea;
1-Phenyl-1-{2-[(1S)-2-hydroxy-1,2-dimethyl-propylamino]-pyrimidin-4-yl}-3-(2,3-dichlorophenyl)-urea;
1-Phenyl-1-{2-[(1S)-2-hydroxy-1,2-dimethyl-propylamino]-pyrimidin-4-yl}-3-(2,4-dichlorophenyl)-urea;
1-Phenyl-1-{2-[(1S)-2-hydroxy-1,2-dimethyl-propylamino]-pyrimidin-4-yl}-3-(2,5-dichlorophenyl)-urea;
1-Phenyl-1-{2-[(1S)-2-hydroxy-1,2-dimethyl-propylamino]-pyrimidin-4-yl}-3-(2,6-dichlorophenyl)-urea;
1-Phenyl-1-{2-[(1S)-2-hydroxy-1,2-dimethyl-propylamino]-pyrimidin-4-yl}-3-(2,3,4-trichlorophenyl)-urea;
1-Phenyl-1-{2-[(1S)-2-hydroxy-1,2-dimethyl-propylamino]-pyrimidin-4-yl}-3-(2,3,5-trichlorophenyl)-urea;
1-Phenyl-1-{2-[(1S)-2-hydroxy-1,2-dimethyl-propylamino]-pyrimidin-4-yl}-3-(2,3,6-trichlorophenyl)-urea;
1-Phenyl-1-{2-[(1S)-2-hydroxy-1,2-dimethyl-propylamino]-pyrimidin-4-yl}-3-(2,4,5-trichlorophenyl)-urea;
1-Phenyl-1-{2-[(1S)-2-hydroxy-1,2-dimethyl-propylamino]-pyrimidin-4-yl}-3-(2,4,6-trichlorophenyl)-urea;
1-(4-Fluorophenyl)-1-{2-[(1S)-2-hydroxy-1,2-dimethyl-propylamino]-pyrimidin-4-yl}-3-o-tolyl-urea;
1-(4-Fluorophenyl)-1-{2-[(1S)-2-hydroxy-1,2-dimethyl-propylamino]-pyrimidin-4-yl}-3-m-tolyl-urea;
1-(4-Fluorophenyl)-1-{2-[(1S)-2-hydroxy-1,2-dimethyl-propylamino]-pyrimidin-4-yl}-3-p-tolyl-urea;
1-(4-Fluorophenyl)-1-{2-[(1S)-2-hydroxy-1,2-dimethyl-propylamino]-pyrimidin-4-yl}-3-(2-fluorophenyl)-urea;
1-(4-Fluorophenyl)-1-{2-[(1S)-2-hydroxy-1,2-dimethyl-propylamino]-pyrimidin-4-yl}-3-(3-fluorophenyl)-urea;
1-(4-Fluorophenyl)-1-{2-[(1S)-2-hydroxy-1,2-dimethyl-propylamino]-pyrimidin-4-yl}-3-(4-fluorophenyl)-urea;
1-(4-Fluorophenyl)-1-{2-[(1S)-2-hydroxy-1,2-dimethyl-propylamino]-pyrimidin-4-yl}-3-(2,3-difluorophenyl)-urea;
1-(4-Fluorophenyl)-1-{2-[(1S)-2-hydroxy-1,2-dimethyl-propylamino]-pyrimidin-4-yl}-3-(2,4-difluorophenyl)-urea;
1-(4-Fluorophenyl)-1-{2-[(1S)-2-hydroxy-1,2-dimethyl-propylamino]-pyrimidin-4-yl}-3-(2,5-difluorophenyl)-urea;
1-(4-Fluorophenyl)-1-{2-[(1S)-2-hydroxy-1,2-dimethyl-propylamino]-pyrimidin-4-yl}-3-(2,6-difluorophenyl)-urea;
1-(4-Fluorophenyl)-1-{2-[(1S)-2-hydroxy-1,2-dimethyl-propylamino]-pyrimidin-4-yl}-3-(2,3,4-trifluorophenyl)-urea;
1-(4-Fluorophenyl)-1-{2-[(1S)-2-hydroxy-1,2-dimethyl-propylamino]-pyrimidin-4-yl}-3-(2,3,5-trifluorophenyl)-urea;
1-(4-Fluorophenyl)-1-{2-[(1S)-2-hydroxy-1,2-dimethyl-propylamino]-pyrimidin-4-yl}-3-(2,3,6-trifluorophenyl)-urea;
1-(4-Fluorophenyl)-1-{2-[(1S)-2-hydroxy-1,2-dimethyl-propylamino]-pyrimidin-4-yl}-3-(2,4,5-trifluorophenyl)-urea;
1-(4-Fluorophenyl)-1-{2-[(1S)-2-hydroxy-1,2-dimethyl-propylamino]-pyrimidin-4-yl}-3-(2,4,6-trifluorophenyl)-urea;
1-(4-Fluorophenyl)-1-{2-[(1S)-2-hydroxy-1,2-dimethyl-propylamino]-pyrimidin-4-yl}-3-(3-chlorophenyl)-urea;
1-(4-Fluorophenyl)-1-{2-[(1S)-2-hydroxy-1,2-dimethyl-propylamino]-pyrimidin-4-yl}-3-(4-chlorophenyl)-urea;
1-(4-Fluorophenyl)-1-{2-[(1S)-2-hydroxy-1,2-dimethyl-propylamino]-pyrimidin-4-yl}-3-(2,3-dichlorophenyl)-urea;
1-(4-Fluorophenyl)-1-{2-[(1S)-2-hydroxy-1,2-dimethyl-propylamino]-pyrimidin-4-yl}-3-(2,4-dichlorophenyl)-urea;
1-(4-Fluorophenyl)-1-{2-[(1S)-2-hydroxy-1,2-dimethyl-propylamino]-pyrimidin-4-yl}-3-(2,5-dichlorophenyl)-urea;
1-(4-Fluorophenyl)-1-{2-[(1S)-2-hydroxy-1,2-dimethyl-propylamino]-pyrimidin-4-yl}-3-(2,3,4-trichlorophenyl)-urea;
1-(4-Fluorophenyl)-1-{2-[(1S)-2-hydroxy-1,2-dimethyl-propylamino]-pyrimidin-4-yl}-3-(2,3,5-trichlorophenyl)-urea;
1-(4-Fluorophenyl)-1-{2-[(1S)-2-hydroxy-1,2-dimethyl-propylamino]-pyrimidin-4-yl}-3-(2,3,6-trichlorophenyl)-urea;
1-(4-Fluorophenyl)-1-{2-[(1S)-2-hydroxy-1,2-dimethyl-propylamino]-pyrimidin-4-yl}-3-(2,4,5-trichlorophenyl)-urea;
1-(4-Fluorophenyl)-1-{2-[(1S)-2-hydroxy-1,2-dimethyl-propylamino]-pyrimidin-4-yl}-3-(2,4,6-trichlorophenyl)-urea;
1-(4-Methoxyphenyl)-1-{2-[(1S)-2-hydroxy-1,2-dimethyl-propylamino]-pyrimidin-4-yl}-3-m-tolyl-urea;
1-(4-Methoxyphenyl)-1-{2-[(1S)-2-hydroxy-1,2-dimethyl-propylamino]-pyrimidin-4-yl}-3-p-tolyl-urea;
1-(4-Methoxyphenyl)-1-{2-[(1S)-2-hydroxy-1,2-dimethyl-propylamino]-pyrimidin-4-yl}-3-(2-fluorophenyl)-urea;
1-(4-Methoxyphenyl)-1-{2-[(1S)-2-hydroxy-1,2-dimethyl-propylamino]-pyrimidin-4-yl}-3-(3-fluorophenyl)-urea;
1-(4-Methoxyphenyl)-1-{2-[(1S)-2-hydroxy-1,2-dimethyl-propylamino]-pyrimidin-4-yl}-3-(4-fluorophenyl)-urea;

1-(4-Methoxyphenyl)-1-{2-[(1S)-2-hydroxy-1,2-dimethyl-propylamino]-pyrimidin-4-yl}-3-(2,3-difluorophenyl)-urea;
1-(4-Methoxyphenyl)-1-{2-[(1S)-2-hydroxy-1,2-dimethyl-propylamino]-pyrimidin-4-yl}-3-(2,4-difluorophenyl)-urea;
1-(4-Methoxyphenyl)-1-{2-[(1S)-2-hydroxy-1,2-dimethyl-propylamino]-pyrimidin-4-yl}-3-(2,5-difluorophenyl)-urea;
1-(4-Methoxyphenyl)-1-{2-[(1S)-2-hydroxy-1,2-dimethyl-propylamino]-pyrimidin-4-yl}-3-(2,6-difluorophenyl)-urea;
1-(4-Methoxyphenyl)-1-{2-[(1S)-2-hydroxy-1,2-dimethyl-propylamino]-pyrimidin-4-yl}-3-(2,3,4-trifluorophenyl)-urea;
1-(4-Methoxyphenyl)-1-{2-[(1S)-2-hydroxy-1,2-dimethyl-propylamino]-pyrimidin-4-yl}-3-(2,3,5-trifluorophenyl)-urea;
1-(4-Methoxyphenyl)-1-{2-[(1S)-2-hydroxy-1,2-dimethyl-propylamino]-pyrimidin-4-yl}-3-(2,3,6-trifluorophenyl)-urea;
1-(4-Methoxyphenyl)-1-{2-[(1S)-2-hydroxy-1,2-dimethyl-propylamino]-pyrimidin-4-yl}-3-(2,4,5-trifluorophenyl)-urea;
1-(4-Methoxyphenyl)-1-{2-[(1S)-2-hydroxy-1,2-dimethyl-propylamino]-pyrimidin-4-yl}-3-(2,4,6-trifluorophenyl)-urea;
1-(4-Methoxyphenyl)-1-{2-[(1S)-2-hydroxy-1,2-dimethyl-propylamino]-pyrimidin-4-yl}-3-(3-chlorophenyl)-urea;
1-(4-Methoxyphenyl)-1-{2-[(1S)-2-hydroxy-1,2-dimethyl-propylamino]-pyrimidin-4-yl}-3-(4-chlorophenyl)-urea;
1-(4-Methoxyphenyl)-1-{2-[(1S)-2-hydroxy-1,2-dimethyl-propylamino]-pyrimidin-4-yl}-3-(2,3-dichlorophenyl)-urea;
1-(4-Methoxyphenyl)-1-{2-[(1S)-2-hydroxy-1,2-dimethyl-propylamino]-pyrimidin-4-yl}-3-(2,4-dichlorophenyl)-urea;
1-(4-Methoxyphenyl)-1-{2-[(1S)-2-hydroxy-1,2-dimethyl-propylamino]-pyrimidin-4-yl}-3-(2,5-dichlorophenyl)-urea;
1-(4-Methoxyphenyl)-1-{2-[(1S)-2-hydroxy-1,2-dimethyl-propylamino]-pyrimidin-4-yl}-3-(2,6-dichlorophenyl)-urea;
1-(4-Methoxyphenyl)-1-{2-[(1S)-2-hydroxy-1,2-dimethyl-propylamino]-pyrimidin-4-yl}-3-(2,3,4-trichlorophenyl)-urea;
1-(4-Methoxyphenyl)-1-{2-[(1S)-2-hydroxy-1,2-dimethyl-propylamino]-pyrimidin-4-yl}-3-(2,3,5-trichlorophenyl)-urea;
1-(4-Methoxyphenyl)-1-{2-[(1S)-2-hydroxy-1,2-dimethyl-propylamino]-pyrimidin-4-yl}-3-(2,3,6-trichlorophenyl)-urea;
1-(4-Methoxyphenyl)-1-{2-[(1S)-2-hydroxy-1,2-dimethyl-propylamino]-pyrimidin-4-yl}-3-(2,4,5-trichlorophenyl)-urea; and
1-(4-Methoxyphenyl)-1-{2-[(1S)-2-hydroxy-1,2-dimethyl-propylamino]-pyrimidin-4-yl}-3-(2,4,6-trichlorophenyl)-urea.

Further non-limiting examples of the first iteration of the first aspect of Category I wherein the index x equals 1 includes:

1-(4-Fluorophenyl)-1-{2-[(1S)-2-hydroxy-1,2-dimethyl-propylamino]-pyrimidin-4-yl}-3-o-methylbenzyl-urea;
1-(4-Fluorophenyl)-1-{2-[(1S)-2-hydroxy-1,2-dimethyl-propylamino]-pyrimidin-4-yl}-3-m-methylbenzyl-urea;
1-(4-Fluorophenyl)-1-{2-[(1S)-2-hydroxy-1,2-dimethyl-propylamino]-pyrimidin-4-yl}-3-p-methylbenzyl-urea;
1-(4-Fluorophenyl)-1-{2-[(1S)-2-hydroxy-1,2-dimethyl-propylamino]-pyrimidin-4-yl}-3-(2-fluorobenzyl)-urea;
1-(4-Fluorophenyl)-1-{2-[(1S)-2-hydroxy-1,2-dimethyl-propylamino]-pyrimidin-4-yl}-3-(3-fluorobenzyl)-urea;
1-(4-Fluorophenyl)-1-{2-[(1S)-2-hydroxy-1,2-dimethyl-propylamino]-pyrimidin-4-yl}-3-(4-fluorobenzyl)-urea;
1-(4-Fluorophenyl)-1-{2-[(1S)-2-hydroxy-1,2-dimethyl-propylamino]-pyrimidin-4-yl}-3-(2,3-difluorobenzyl)-urea;
1-(4-Fluorophenyl)-1-{2-[(1S)-2-hydroxy-1,2-dimethyl-propylamino]-pyrimidin-4-yl}-3-(2,4-difluorobenzyl)-urea;
1-(4-Fluorophenyl)-1-{2-[(1S)-2-hydroxy-1,2-dimethyl-propylamino]-pyrimidin-4-yl}-3-(2,5-difluorobenzyl)-urea;
1-(4-Fluorophenyl)-1-{2-[(1S)-2-hydroxy-1,2-dimethyl-propylamino]-pyrimidin-4-yl}-3-(2,6-difluorobenzyl)-urea;
1-(4-Fluorophenyl)-1-{2-[(1S)-2-hydroxy-1,2-dimethyl-propylamino]-pyrimidin-4-yl}-3-(2,3,4-trifluorobenzyl)-urea;
1-(4-Fluorophenyl)-1-{2-[(1S)-2-hydroxy-1,2-dimethyl-propylamino]-pyrimidin-4-yl}-3-(2,3,5-trifluorobenzyl)-urea;
1-(4-Fluorophenyl)-1-{2-[(1S)-2-hydroxy-1,2-dimethyl-propylamino]-pyrimidin-4-yl}-3-(2,3,6-trifluorobenzyl)-urea;
1-(4-Fluorophenyl)-1-{2-[(1S)-2-hydroxy-1,2-dimethyl-propylamino]-pyrimidin-4-yl}-3-(2,4,5-trifluorobenzyl)-urea;
1-(4-Fluorophenyl)-1-{2-[(1S)-2-hydroxy-1,2-dimethyl-propylamino]-pyrimidin-4-yl}-3-(2,4,6-trifluorobenzyl)-urea;
1-(4-Fluorophenyl)-1-{2-[(1S)-2-hydroxy-1,2-dimethyl-propylamino]-pyrimidin-4-yl}-3-(3-chlorobenzyl)-urea;
1-(4-Fluorophenyl)-1-{2-[(1S)-2-hydroxy-1,2-dimethyl-propylamino]-pyrimidin-4-yl}-3-(4-chlorobenzyl)-urea;
1-(4-Fluorophenyl)-1-{2-[(1S)-2-hydroxy-1,2-dimethyl-propylamino]-pyrimidin-4-yl}-3-(2,3-dichlorobenzyl)-urea;
1-(4-Fluorophenyl)-1-{2-[(1S)-2-hydroxy-1,2-dimethyl-propylamino]-pyrimidin-4-yl}-3-(2,4-dichlorobenzyl)-urea;
1-(4-Fluorobenzyl)-1-{2-[(1S)-2-hydroxy-1,2-dimethyl-propylamino]-pyrimidin-4-yl}-3-(2,5-difluorophenyl)-urea;
1-(4-Fluorophenyl)-1-{2-[(1S)-2-hydroxy-1,2-dimethyl-propylamino]-pyrimidin-4-yl}-3-(2,6-dichlorobenzyl)-urea;
1-(4-Fluorophenyl)-1-{2-[(1S)-2-hydroxy-1,2-dimethyl-propylamino]-pyrimidin-4-yl}-3-(2,3,4-trichlorobenzyl)-urea;
1-(4-Fluorophenyl)-1-{2-[(1S)-2-hydroxy-1,2-dimethyl-propylamino]-pyrimidin-4-yl}-3-(2,3,5-trichlorobenzyl)-urea;

1-(4-Fluorophenyl)-1-{2-[(1S)-2-hydroxy-1,2-dimethyl-propylamino]-pyrimidin-4-yl}-3-(2,3,6-trichlorobenzyl)-urea;
1-(4-Fluorophenyl)-1-{2-[(1S)-2-hydroxy-1,2-dimethyl-propylamino]-pyrimidin-4-yl}-3-(2,4,5-trichlorobenzyl)-urea;
1-(4-Fluorophenyl)-1-{2-[(1S)-2-hydroxy-1,2-dimethyl-propylamino]-pyrimidin-4-yl}-3-(2,4,6-trichlorobenzyl)-urea;
1-(4-Methoxyphenyl)-1-{2-[(1S)-2-hydroxy-1,2-dimethyl-propylamino]-pyrimidin-4-yl}-3-(3-chlorobenzyl)-urea;
1-(4-Methoxyphenyl)-1-{2-[(1S)-2-hydroxy-1,2-dimethyl-propylamino]-pyrimidin-4-yl}-3-(4-chlorobenzyl)-urea;
1-(4-Methoxyphenyl)-1-{2-[(1S)-2-hydroxy-1,2-dimethyl-propylamino]-pyrimidin-4-yl}-3-(2,3-dichlorobenzyl)-urea;
1-(4-Methoxyphenyl)-1-{2-[(1S)-2-hydroxy-1,2-dimethyl-propylamino]-pyrimidin-4-yl}-3-(2,4-dichlorobenzyl)-urea;
1-(4-Methoxybenzyl)-1-{2-[(1S)-2-hydroxy-1,2-dimethyl-propylamino]-pyrimidin-4-yl}-3-(2,5-difluorophenyl)-urea;
1-(4-Methoxyphenyl)-1-{2-[(1S)-2-hydroxy-1,2-dimethyl-propylamino]-pyrimidin-4-yl}-3-(2,6-dichlorobenzyl)-urea;
1-(4-Methoxyphenyl)-1-{2-[(1S)-2-hydroxy-1,2-dimethyl-propylamino]-pyrimidin-4-yl}-3-(2,3,4-trichlorobenzyl)-urea;
1-(4-Methoxyphenyl)-1-{2-[(1S)-2-hydroxy-1,2-dimethyl-propylamino]-pyrimidin-4-yl}-3-(2,3,5-trichlorobenzyl)-urea;
1-(4-Methoxyphenyl)-1-{2-[(1S)-2-hydroxy-1,2-dimethyl-propylamino]-pyrimidin-4-yl}-3-(2,3,6-trichlorobenzyl)-urea;
1-(4-Methoxyphenyl)-1-{2-[(1S)-2-hydroxy-1,2-dimethyl-propylamino]-pyrimidin-4-yl}-3-(2,4,5-trichlorobenzyl)-urea; and
1-(4-Methoxyphenyl)-1-{2-[(1S)-2-hydroxy-1,2-dimethyl-propylamino]-pyrimidin-4-yl}-3-(2,4,6-trichlorobenzyl)-urea.

The second iteration of the first aspect of Category I includes compounds having the formula:

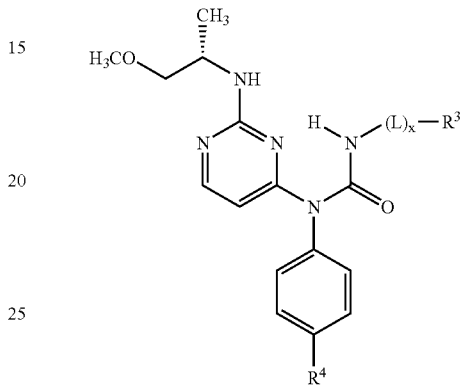

wherein non-limiting examples of L, $R^3$, and $R^4$ are defined herein below in Table II. In Table II, compounds 201-300 have x equal to 0; for compounds 301-400 x is equal to 1 and the L unit is defined therein.

TABLE II

| No. | $R^4$ | $R^3$ | No. | $R^4$ | L | $R^3$ |
|---|---|---|---|---|---|---|
| 201 | —H | 2-fluorophenyl | 301 | —H | —CH$_2$— | 2-fluorophenyl |
| 202 | —H | 3-fluorophenyl | 302 | —H | —CH$_2$— | 3-fluorophenyl |
| 203 | —H | 4-fluorophenyl | 303 | —H | —CH$_2$— | 4-fluorophenyl |
| 204 | —H | 2,6-difluorophenyl | 304 | —H | —CH$_2$— | 2,6-difluorophenyl |
| 205 | —H | 2-chlorophenyl | 305 | —H | —CH$_2$— | 2-chlorophenyl |
| 206 | —H | 3-chlorophenyl | 306 | —H | —CH$_2$— | 3-chlorophenyl |
| 207 | —H | 4-chlorophenyl | 307 | —H | —CH$_2$— | 4-chlorophenyl |
| 208 | —H | 3,4-dichlorophenyl | 308 | —H | —CH$_2$— | 3,4-dichlorophenyl |
| 209 | —H | 2,4-dichlorophenyl | 309 | —H | —CH$_2$— | 2,4-dichlorophenyl |
| 210 | —H | 2,6-dichlorophenyl | 310 | —H | —CH$_2$— | 2,6-dichlorophenyl |
| 211 | —H | 2-methylphenyl | 311 | —H | —CH$_2$— | 2-methylphenyl |
| 212 | —H | 3-methylphenyl | 312 | —H | —CH$_2$— | 3-methylphenyl |
| 213 | —H | 4-methylphenyl | 313 | —H | —CH$_2$— | 4-methylphenyl |
| 214 | —H | 2,4-dimethylphenyl | 314 | —H | —CH$_2$— | 2,4-dimethylphenyl |
| 215 | —H | 2,6-dimethylphenyl | 315 | —H | —CH$_2$— | 2,6-dimethylphenyl |
| 216 | —H | 2-methoxyphenyl | 316 | —H | —CH$_2$— | 2-methoxyphenyl |
| 217 | —H | 3-methoxyphenyl | 317 | —H | —CH$_2$— | 3-methoxyphenyl |
| 218 | —H | 4-methoxyphenyl | 318 | —H | —CH$_2$— | 4-methoxyphenyl |
| 219 | —H | 3-(CF$_3$)-phenyl | 319 | —H | —CH$_2$— | 3-(CF$_3$)-phenyl |
| 220 | —H | 4-(CF$_3$)-phenyl | 320 | —H | —CH$_2$— | 4-(CF$_3$)-phenyl |
| 221 | —F | 2-fluorophenyl | 321 | —F | —CH$_2$— | 2-fluorophenyl |
| 222 | —F | 3-fluorophenyl | 322 | —F | —CH$_2$— | 3-fluorophenyl |
| 223 | —F | 4-fluorophenyl | 323 | —F | —CH$_2$— | 4-fluorophenyl |
| 224 | —F | 2,6-difluorophenyl | 324 | —F | —CH$_2$— | 2,6-difluorophenyl |
| 225 | —F | 2-chlorophenyl | 325 | —F | —CH$_2$— | 2-chlorophenyl |
| 226 | —F | 3-chlorophenyl | 326 | —F | —CH$_2$— | 3-chlorophenyl |
| 227 | —F | 4-chlorophenyl | 327 | —F | —CH$_2$— | 4-chlorophenyl |
| 228 | —F | 3,4-dichlorophenyl | 328 | —F | —CH$_2$— | 3,4-dichlorophenyl |
| 229 | —F | 2,4-dichlorophenyl | 329 | —F | —CH$_2$— | 2,4-dichlorophenyl |
| 230 | —F | 2,6-dichlorophenyl | 330 | —F | —CH$_2$— | 2,6-dichlorophenyl |
| 231 | —F | 2-methylphenyl | 331 | —F | —CH$_2$— | 2-methylphenyl |
| 232 | —F | 3-methylphenyl | 332 | —F | —CH$_2$— | 3-methylphenyl |
| 233 | —F | 4-methylphenyl | 333 | —F | —CH$_2$— | 4-methylphenyl |
| 234 | —F | 2,4-dimethylphenyl | 334 | —F | —CH$_2$— | 2,4-dimethylphenyl |

TABLE II-continued

| No. | R⁴ | R³ | No. | R⁴ | L | R³ |
|---|---|---|---|---|---|---|
| 235 | —F | 2,6-dimethylphenyl | 335 | —F | —CH$_2$— | 2,6-dimethylphenyl |
| 236 | —F | 2-methoxyphenyl | 336 | —F | —CH$_2$— | 2-methoxyphenyl |
| 237 | —F | 3-methoxyphenyl | 337 | —F | —CH$_2$— | 3-methoxyphenyl |
| 238 | —F | 4-methoxyphenyl | 338 | —F | —CH$_2$— | 4-methoxyphenyl |
| 239 | —F | 3-(CF$_3$)-phenyl | 339 | —F | —CH$_2$— | 3-(CF$_3$)-phenyl |
| 240 | —F | 4-(CF$_3$)-phenyl | 340 | —F | —CH$_2$— | 4-(CF$_3$)-phenyl |
| 241 | —CH$_3$ | 2-fluorophenyl | 341 | —CH$_3$ | —CH$_2$— | 2-fluorophenyl |
| 242 | —CH$_3$ | 3-fluorophenyl | 342 | —CH$_3$ | —CH$_2$— | 3-fluorophenyl |
| 243 | —CH$_3$ | 4-fluorophenyl | 343 | —CH$_3$ | —CH$_2$— | 4-fluorophenyl |
| 244 | —CH$_3$ | 2,6-difluorophenyl | 344 | —CH$_3$ | —CH$_2$— | 2,6-difluorophenyl |
| 245 | —CH$_3$ | 2-chlorophenyl | 345 | —CH$_3$ | —CH$_2$— | 2-chlorophenyl |
| 246 | —CH$_3$ | 3-chlorophenyl | 346 | —CH$_3$ | —CH$_2$— | 3-chlorophenyl |
| 247 | —CH$_3$ | 4-chlorophenyl | 347 | —CH$_3$ | —CH$_2$— | 4-chlorophenyl |
| 248 | —CH$_3$ | 3,4-dichlorophenyl | 348 | —CH$_3$ | —CH$_2$— | 3,4-dichlorophenyl |
| 249 | —CH$_3$ | 2,4-dichlorophenyl | 349 | —CH$_3$ | —CH$_2$— | 2,4-dichlorophenyl |
| 250 | —CH$_3$ | 2,6-dichlorophenyl | 350 | —CH$_3$ | —CH$_2$— | 2,6-dichlorophenyl |
| 251 | —CH$_3$ | 2-methylphenyl | 351 | —CH$_3$ | —CH$_2$— | 2-methylphenyl |
| 252 | —CH$_3$ | 3-methylphenyl | 352 | —CH$_3$ | —CH$_2$— | 3-methylphenyl |
| 253 | —CH$_3$ | 4-methylphenyl | 353 | —CH$_3$ | —CH$_2$— | 4-methylphenyl |
| 254 | —CH$_3$ | 2,4-dimethylphenyl | 354 | —CH$_3$ | —CH$_2$— | 2,4-dimethylphenyl |
| 255 | —CH$_3$ | 2,6-dimethylphenyl | 355 | —CH$_3$ | —CH$_2$— | 2,6-dimethylphenyl |
| 256 | —CH$_3$ | 2-methoxyphenyl | 356 | —CH$_3$ | —CH$_2$— | 2-methoxyphenyl |
| 257 | —CH$_3$ | 3-methoxyphenyl | 357 | —CH$_3$ | —CH$_2$— | 3-methoxyphenyl |
| 258 | —CH$_3$ | 4-methoxyphenyl | 358 | —CH$_3$ | —CH$_2$— | 4-methoxyphenyl |
| 259 | —CH$_3$ | 3-(CF$_3$)-phenyl | 359 | —CH$_3$ | —CH$_2$— | 3-(CF$_3$)-phenyl |
| 260 | —CH$_3$ | 4-(CF$_3$)-phenyl | 360 | —CH$_3$ | —CH$_2$— | 4-(CF$_3$)-phenyl |
| 261 | —OCH$_3$ | 2-fluorophenyl | 361 | —OCH$_3$ | —CH$_2$— | 2-fluorophenyl |
| 262 | —OCH$_3$ | 3-fluorophenyl | 362 | —OCH$_3$ | —CH$_2$— | 3-fluorophenyl |
| 263 | —OCH$_3$ | 4-fluorophenyl | 363 | —OCH$_3$ | —CH$_2$— | 4-fluorophenyl |
| 264 | —OCH$_3$ | 2,6-difluorophenyl | 364 | —OCH$_3$ | —CH$_2$— | 2,6-difluorophenyl |
| 265 | —OCH$_3$ | 2-chlorophenyl | 365 | —OCH$_3$ | —CH$_2$— | 2-chlorophenyl |
| 266 | —OCH$_3$ | 3-chlorophenyl | 366 | —OCH$_3$ | —CH$_2$— | 3-chlorophenyl |
| 267 | —OCH$_3$ | 4-chlorophenyl | 367 | —OCH$_3$ | —CH$_2$— | 4-chlorophenyl |
| 268 | —OCH$_3$ | 3,4-dichlorophenyl | 368 | —OCH$_3$ | —CH$_2$— | 3,4-dichlorophenyl |
| 269 | —OCH$_3$ | 2,4-dichlorophenyl | 369 | —OCH$_3$ | —CH$_2$— | 2,4-dichlorophenyl |
| 270 | —OCH$_3$ | 2,6-dichlorophenyl | 370 | —OCH$_3$ | —CH$_2$— | 2,6-dichlorophenyl |
| 271 | —OCH$_3$ | 2-methylphenyl | 371 | —OCH$_3$ | —CH$_2$— | 2-methylphenyl |
| 272 | —OCH$_3$ | 3-methylphenyl | 372 | —OCH$_3$ | —CH$_2$— | 3-methylphenyl |
| 273 | —OCH$_3$ | 4-methylphenyl | 373 | —OCH$_3$ | —CH$_2$— | 4-methylphenyl |
| 274 | —OCH$_3$ | 2,4-dimethylphenyl | 374 | —OCH$_3$ | —CH$_2$— | 2,4-dimethylphenyl |
| 275 | —OCH$_3$ | 2,6-dimethylphenyl | 375 | —OCH$_3$ | —CH$_2$— | 2,6-dimethylphenyl |
| 276 | —OCH$_3$ | 2-methoxyphenyl | 376 | —OCH$_3$ | —CH$_2$— | 2-methoxyphenyl |
| 277 | —OCH$_3$ | 3-methoxyphenyl | 377 | —OCH$_3$ | —CH$_2$— | 3-methoxyphenyl |
| 278 | —OCH$_3$ | 4-methoxyphenyl | 378 | —OCH$_3$ | —CH$_2$— | 4-methoxyphenyl |
| 279 | —OCH$_3$ | 3-(CF$_3$)-phenyl | 379 | —OCH$_3$ | —CH$_2$— | 3-(CF$_3$)-phenyl |
| 280 | —OCH$_3$ | 4-(CF$_3$)-phenyl | 380 | —OCH$_3$ | —CH$_2$— | 4-(CF$_3$)-phenyl |
| 281 | —SCH$_3$ | 2-fluorophenyl | 381 | —SCH$_3$ | —CH$_2$— | 2-fluorophenyl |
| 282 | —SCH$_3$ | 3-fluorophenyl | 382 | —SCH$_3$ | —CH$_2$— | 3-fluorophenyl |
| 283 | —SCH$_3$ | 4-fluorophenyl | 383 | —SCH$_3$ | —CH$_2$— | 4-fluorophenyl |
| 284 | —SCH$_3$ | 2,6-difluorophenyl | 384 | —SCH$_3$ | —CH$_2$— | 2,6-difluorophenyl |
| 285 | —SCH$_3$ | 2-chlorophenyl | 385 | —SCH$_3$ | —CH$_2$— | 2-chlorophenyl |
| 286 | —SCH$_3$ | 3-chlorophenyl | 386 | —SCH$_3$ | —CH$_2$— | 3-chlorophenyl |
| 287 | —SCH$_3$ | 4-chlorophenyl | 387 | —SCH$_3$ | —CH$_2$— | 4-chlorophenyl |
| 288 | —SCH$_3$ | 3,4-dichlorophenyl | 388 | —SCH$_3$ | —CH$_2$— | 3,4-dichlorophenyl |
| 289 | —SCH$_3$ | 2,4-dichlorophenyl | 389 | —SCH$_3$ | —CH$_2$— | 2,4-dichlorophenyl |
| 290 | —SCH$_3$ | 2,6-dichlorophenyl | 390 | —SCH$_3$ | —CH$_2$— | 2,6-dichlorophenyl |
| 291 | —SCH$_3$ | 2-methylphenyl | 391 | —SCH$_3$ | —CH$_2$— | 2-methylphenyl |
| 292 | —SCH$_3$ | 3-methylphenyl | 392 | —SCH$_3$ | —CH$_2$— | 3-methylphenyl |
| 293 | —SCH$_3$ | 4-methylphenyl | 393 | —SCH$_3$ | —CH$_2$— | 4-methylphenyl |
| 294 | —SCH$_3$ | 2,4-dimethylphenyl | 394 | —SCH$_3$ | —CH$_2$— | 2,4-dimethylphenyl |
| 295 | —SCH$_3$ | 2,6-dimethylphenyl | 395 | —SCH$_3$ | —CH$_2$— | 2,6-dimethylphenyl |
| 296 | —SCH$_3$ | 2-methoxyphenyl | 396 | —SCH$_3$ | —CH$_2$— | 2-methoxyphenyl |
| 297 | —SCH$_3$ | 3-methoxyphenyl | 397 | —SCH$_3$ | —CH$_2$— | 3-methoxyphenyl |
| 298 | —SCH$_3$ | 4-methoxyphenyl | 398 | —SCH$_3$ | —CH$_2$— | 4-methoxyphenyl |
| 299 | —SCH$_3$ | 3-(CF$_3$)-phenyl | 399 | —SCH$_3$ | —CH$_2$— | 3-(CF$_3$)-phenyl |
| 300 | —SCH$_3$ | 4-(CF$_3$)-phenyl | 400 | —SCH$_3$ | —CH$_2$— | 4-(CF$_3$)-phenyl |

The following are further non-limiting examples of compounds which comprise the second iteration of the first aspect of Category I according to the present invention.

1-(4-Methoxyphenyl)-1-{2-[(1S)-2-methoxy-1-methyl-ethylamino]-pyrimidin-4-yl}-3-(2-chlorobenzyl)-urea: $^1$H NMR (300 MHz, CDCl$_3$) δ 10.56 (br s, 1H), 7.87 (d, J=5.8 Hz, 1H), 7.54 (m, 1H), 7.42 (m, 1H), 7.29-7.20 (m, 2H), 7.14 (d, J=8.8 Hz, 2H), 7.00 (d, J=8.8 Hz, 2H), 5.49 (d, J=6.2 Hz, 1H), 5.38 (br s, 1H), 4.67 (d, J=5.9 Hz, 2H), 4.09-3.90 (m, 1H), 3.86 (s, 3H), 1.18 (d, J=5.8 Hz, 3H); MS (ESI) m/z 456 (M+1).

1-(4-Methoxyphenyl)-1-{2-[(1S)-2-methoxy-1-methyl-ethylamino]-pyrimidin-4-yl}-3-(2-methylbenzyl)-urea: $^1$H NMR (300 MHz, CDCl$_3$) δ 10.27 (m, 1H), 7.86 (d, J=5.8 Hz, 1H), 7.41-7.36 (m, 1H), 7.26-7.23 (m, 3H), 7.18 (d, J=9.0 Hz, 2H), 7.02 (d, J=9.0 Hz, 2H), 5.48 (d, J=5.8 Hz, 1H), 5.25 (br s, 1H), 4.57 (d, J=4.6 Hz, 1H), 3.87 (s, 3H), 3.72-3.18 (m, 1H), 3.32 (s, 3H), 3.20-2.98 (m, 2H), 2.43 (s, 3H), 0.98 (m, 3H); MS (ESI) m/z 436 (M+1).

1-(4-Methoxyphenyl)-1-{2-[(1S)-2-methoxy-1-methyl-ethylamino]-pyrimidin-4-yl}-3-(2,4-dichlorobenzyl)-urea: $^1$H NMR (300 MHz, CDCl$_3$) δ 10.56 (br s, 1H), 7.89 (d, J=6.0 Hz, 1H), 7.49 (d, J=8.2 Hz, 1H), 7.45 (d, J=2.0 Hz, 1H), 7.25 (dd, J=2.0, 8.2 Hz, 1H), 7.14 (d, J=8.8 Hz, 2H), 7.01 (d, J=8.8 Hz, 2H), 5.53 (d, J=6.0 Hz, 1H), 5.53-5.35 (m, 1H), 4.63 (d, J=5.9 Hz, 2H), 4.19-3.90 (m, 1H), 3.87 (s, 3H), 3.42-3.30 (m, 1H), 3.40 (s, 3H), 1.23 (d, J=6.6 Hz, 3H); MS (ESI) m/z 490 (M+1).

1-(4-Methoxyphenyl)-1-{2-[(1S)-2-methoxy-1-methyl-ethylamino]-pyrimidin-4-yl}-3-(3,4-dichlorobenzyl)-urea: $^1$H NMR (300 MHz, CDCl$_3$) δ 10.15 (br d, J=7.3 Hz, 1H), 9.44 (s, 1H), 7.58 (d, J=7.3 Hz, 1H), 7.48 (d, J=1.8 Hz, 1H), 7.45 (d, J=8.4 Hz, 1H), 7.24 (dd, J=1.8, 8.4 Hz, 1H), 7.16 (d, J=8.8 Hz, 2H), 7.04 (d, J=8.8 Hz, 2H), 5.83 (d, J=7.0 Hz, 1H), 4.67 (dd, J=6.6, 14.6 Hz, 1H), 4.32 (dd, J=4.4, 14.6 Hz, 1H), 3.88 (s, 3H), 3.85-3.76 (m, 1H), 3.35-3.21 (m, 2H), 3.30 (s, 3H), 1.17 (d, J=6.6 Hz, 3H); MS (ESI) m/z 490 (M+1).

1-(4-Ethoxyphenyl)-1-{2-[(1S)-2-methoxy-1-methyl-ethylamino]-pyrimidin-4-yl}-3-(2-chlorobenzyl)-urea: $^1$H NMR (300 MHz, CDCl$_3$) δ 10.59 (br s, 1H), 7.90 (d, J=5.9 Hz, 1H), 7.57-7.54 (m, 1H), 7.46-7.42 (m, 1H), 7.32-7.26 (m, 2H), 7.14 (d, J=8.9 Hz, 2H), 7.00 (d, J=8.8 Hz, 2H), 5.52 (d, J=5.9 Hz, 1H), 5.34 (br s, 1H), 4.69 (d, J=5.7 Hz, 2H), 4.10 (q, J=7.1 Hz, 1H), 4.00 (br s, 1H), 3.39 (s, 5H), 1.47 (t, J=7.1 Hz, 3H), 1.20 (d, J=6.2 Hz, 3H); MS (ESI) m/z 470 (M+1).

1-(4-Fluorophenyl)-1-{2-[(1S)-2-methoxy-1-methyl-ethylamino]-pyrimidin-4-yl}-3-(2-fluorophenyl)-urea: $^1$H NMR (300 MHz, CDCl$_3$) δ 8.28 (m, 1H), 7.98 (d, J=5.8 Hz, 1H), 7.29-6.98 (m, 8H), 5.45 (d, J=5.8 Hz, 1H), 5.39 (br s, 1H), 4.34-4.27 (m, 1H), 3.53-3.45 (m, 2H), 3.41 (s, 3H), 1.31 (d, J=6.6 Hz, 3H); $^{13}$C (75 MHz, CDCl$_3$) δ 164.3, 161.8, 161.1, 159.6, 159.0, 152.9, 137.6, 134.8, 131.7, 125.0, 123.6, 117.3, 117.0, 115.0, 114.8, 99.2, 76.1, 59.4, 46.9, 18.1; MS (ESI) m/z 414 (M+1).

1-(4-Fluorophenyl)-1-{2-[(1S)-2-methoxy-1-methyl-ethylamino]-pyrimidin-4-yl}-3-(2-chlorophenyl)-urea: $^1$H NMR (300 MHz, CDCl$_3$) δ 8.37 (d, J=8.4 Hz, 1H), 7.99 (d, J=5.8 Hz, 1H), 7.42 (d, J=7.7 Hz, 1H), 7.29-7.18 (m, 5H), 7.02 (t, J=7.7 Hz, 1H), 5.60 (br s, 1H), 5.47 (d, J=5.8 Hz, 1H), 4.26 (m, 1H), 3.56-3.38 (m, 2H), 3.42 (s, 3H), 1.29 (d, J=6.6 Hz, 3H); $^{13}$C (75 MHz, CDCl$_3$) δ 164.3, 161.71, 159.8, 158.9, 153.1, 136.4, 135.0, 131.7, 129.4, 128.0, 124.2, 122.2, 117.3, 117.0, 99.3, 76.0, 59.4, 46.9, 18.1.

1-(4-Fluorophenyl)-1-{2-[(1S)-2-methoxy-1-methylethy-lamino]-pyrimidin-4-yl}-3-(2-chlorobenzyl)-urea: $^1$H NMR (300 MHz, CDCl$_3$) δ 10.60 (s, 1H), 7.90 (d, J=5.8 Hz, 1H), 7.54 (dd, J=3.5, 5.7 Hz, 1H), 7.44 (dd, J=3.7, 5.7 Hz, 1H), 7.31-7.15 (m, 6H), 5.42 (d, J=5.8 Hz, 1H), 5.41-5.27 (m, 1H), 4.67 (d, J=5.7 Hz, 2H), 3.41-3.21 (m, 2H), 3.38 (s, 3H), 1.19 (br d, J=4.9 Hz, 3H); MS (ESI) m/z 444 (M+1).

1-(4-Fluorophenyl)-1-{2-[(1S)-2-methoxy-1-methyl-ethylamino]-pyrimidin-4-yl}-3-(4-trifluoromethylphenyl)-urea: $^1$H NMR (300 MHz, CDCl$_3$) δ 12.62 (s, 1H), 7.96 (d, J=5.9 Hz, 1H), 7.68 (d, J=8.4 Hz, 2H), 7.57 (d, J=8.4 Hz, 2H), 7.29-7.18 (m, 4H), 5.49 (br s, 1H), 5.46 (d, J=5.8 Hz, 1H), 4.27 (m, 1H), 3.50 (d, J=4.8 Hz, 1H), 3.40 (s, 3H), 1.45 (d, J=6.6 Hz, 3H); $^{13}$C (75 MHz, CDCl$_3$) δ 164.3, 162.0, 161.0, 160.1, 159.2, 153.0, 141.7, 135.0, 131.6, 126.4, 125.5, 120.2, 117.4, 117.1, 99.4, 76.1, 59.4, 47.3, 18.3; MS (ESI) m/z 464 (M+1).

1-(4-Fluorophenyl)-1-{2-[(1S)-2-methoxy-1-methyl-ethylamino]-pyrimidin-4-yl}-3-o-tolyl-urea: $^1$H NMR (300 MHz, CDCl$_3$) δ 12.03 (s, 1H), 7.98 (d, J=5.8 Hz, 1H), 7.29-7.15 (m, 7H), 7.05 (dd, J=7.1, 7.3 Hz, 1H), 5.50 (d, J=5.8 Hz, 1H), 5.30 (d, J=7.8 Hz, 1H), 4.22 (m, 1H), 3.50-3.39 (m, 2H), 3.38 (s, 3H), 2.44 (s, 3H), 1.28 (d, J=6.6 Hz, 3H); $^{13}$C (75 MHz, CDCl$_3$) δ 163.9, 161.8, 160.6, 159.6, 158.4, 153.0, 136.8, 135.1, 131.5, 130.2, 126.6, 124.2, 116.9, 116.6, 99.4, 75.6, 59.1, 46.7, 18.9, 17.8; MS (ESI) m/z 410 (M+1).

1-(4-Dimethylaminophenyl)-1-{2-[(1S)-2-methoxy-1-methyl-ethylamino]-pyrimidin-4-yl}-3-(2-chlorophenyl)-urea: $^1$H NMR (300 MHz, CDCl$_3$) δ 13.08 (s, 1H), 8.47 (d, J=8.4 Hz, 1H), 7.99 (d, J=5.8 Hz, 1H), 7.43 (d, J=8.0 Hz, 1H), 7.26 (t, J=7.1 Hz, 1H), 7.12 (d, J=8.8 Hz, 2H), 7.02 (t, J=8.7 Hz, 1H), 6.81 (d, J=8.9 Hz, 2H), 5.64 (d, J=5.8 Hz, 1H), 5.56 (br d, J=7.9 Hz, 1H), 4.29 (m, 1H), 3.54-3.47 (m, 2H), 3.45 (s, 3H), 3.03 (s, 6H), 1.32 (d, J=6.6 Hz, 3H); MS (ESI) m/z 455 (M+1).

1-(4-Methylsulfanylphenyl)-1-{2-[(1S)-2-methoxy-1-methylethylamino]-pyrimidin-4-yl}-3-(2-chlorobenzyl)-urea: $^1$H NMR (300 MHz, CDCl$_3$) δ 9.91 (br d, J=8.0 Hz, 1H), 9.20 (br s, 1H), 7.62 (d, J=7.3 Hz, 1H), 7.53-7.49 (m, 1H), 7.46-7.44 (m, 1H), 7.42-7.37 (m, 1H), 7.39 (d, J=8.6 Hz, 2H), 7.32-7.30 (m, 1H), 7.18 (d, J=8.6 Hz, 2H), 5.92 (d, J=6.8 Hz, 1H), 4.75 (dd, J=6.0, 14.6, Hz, 1H), 4.58 (dd, J=4.8, 14.6 Hz, 1H), 3.89-3.79 (m, 1H), 3.30-3.23 (m, 1H), 3.27 (s, 3H), 3.17 (dd, J=3.8, 9.5 Hz, 1H), 2.55 (s, 3H), 1.11 (d, J=6.8 Hz, 3H); MS (ESI) m/z 472 (M+1).

1-(4-Methylsulfanylphenyl)-1-{2-[(1S)-2-methoxy-1-methylethylamino]-pyrimidin-4-yl}-3-(2-methylbenzyl)-urea: $^1$H NMR (300 MHz, CDCl$_3$) δ 10.20 (br s, 1H), 7.37 (d, J=8.8 Hz, 3H), 7.24-7.35 (m, 3H), 7.18 (d, J=8.8 Hz, 2H), 5.48 (d, J=5.8 Hz, 1H), 5.33 (brs, 1H), 4.60 (dd, J=5.1, 14.6 Hz, 1H), 4.54 (dd, J=4.8, 14.3 Hz, 1H), 3.31 (s, 3H), 3.09 (br d, J=25.2 Hz, 2H), 2.54 (s, 3H), 2.43 (s, 3H), 0.98 (br s, 3H); MS (ESI) m/z 452 (M+1).

1-(4-Fluorophenyl)-1-{2-[(1S)-2-methoxy-1-methylethy-lamino]-pyrimidin-4-yl}-3-(2-methylbenzyl)-urea: $^1$H NMR (300 MHz, CDCl$_3$) δ 10.26 (br s, 1H), 7.88 (d, J=5.9 Hz, 1H), 7.39 (d, J=7.3 Hz, 1H), 7.28-7.17 (m, 7H), 5.42 (d, J=5.9 Hz, 1H), 5.33 (br s, 1H), 4.61 (dd, J=4.9, 14.5 Hz, 1H), 4.48 (dd, J=4.8, 14.5 Hz, 1H), 3.33 (s, 3H), 3.16 (br d, J=26.3 Hz, 2H), 2.44 (s, 3H), 0.99 (br s, 3H); MS (ESI) m/z 424 (M+1).

1-Phenyl-1-{2-[(1S)-2-methoxy-1-methyl-ethylamino]-pyrimidin-4-yl}-3-(2-methylphenyl)-urea: $^1$H NMR (300 MHz, CDCl$_3$) δ 8.00 (m, 1H), 7.99 (d, J=5.8 Hz, 1H), 7.57-7.46 (m, 3H), 7.38-7.19 (m, 5H), 7.07 (t, J=7.4 Hz, 1H), 5.55 (d, J=5.8 Hz, 1H), 5.29 (d, J=8.0 Hz, 1H), 4.25 (m, 1H), 3.81-3.43 (m, 2H), 3.41 (s, 3H), 2.48 (s, 3H), 1.31 (d, J=6.6 Hz, 3H); MS (ESI) m/z 392 (M+1).

Further non-limiting examples of the second iteration of the first aspect of Category I wherein the index x equals 0 includes:

1-Phenyl-1-{2-[(1S)-2-methoxy-1-methyl-ethylamino]-pyrimidin-4-yl}-3-m-tolyl-urea;
1-Phenyl-1-{2-[(1S)-2-methoxy-1-methyl-ethylamino]-pyrimidin-4-yl}-3-p-tolyl-urea;
1-Phenyl-1-{2-[(1S)-2-methoxy-1-methyl-ethylamino]-pyrimidin-4-yl}-3-(2-fluorophenyl)-urea;
1-Phenyl-1-{2-[(1S)-2-methoxy-1-methyl-ethylamino]-pyrimidin-4-yl}-3-(3-fluorophenyl)-urea;
1-Phenyl-1-{2-[(1S)-2-methoxy-1-methyl-ethylamino]-pyrimidin-4-yl}-3-(4-fluorophenyl)-urea;
1-Phenyl-1-{2-[(1S)-2-methoxy-1-methyl-ethylamino]-pyrimidin-4-yl}-3-(2,3-difluorophenyl)-urea;
1-Phenyl-1-{2-[(1S)-2-methoxy-1-methyl-ethylamino]-pyrimidin-4-yl}-3-(2,4-difluorophenyl)-urea;

1-Phenyl-1-{2-[(1S)-2-methoxy-1-methyl-ethylamino]-pyrimidin-4-yl}-3-(2,5-difluorophenyl)-urea;
1-Phenyl-1-{2-[(1S)-2-methoxy-1-methyl-ethylamino]-pyrimidin-4-yl}-3-(2,6-difluorophenyl)-urea;
1-Phenyl-1-{2-[(1S)-2-methoxy-1-methyl-ethylamino]-pyrimidin-4-yl}-3-(2,3,4-trifluorophenyl)-urea;
1-Phenyl-1-{2-[(1S)-2-methoxy-1-methyl-ethylamino]-pyrimidin-4-yl}-3-(2,3,5-trifluorophenyl)-urea;
1-Phenyl-1-{2-[(1S)-2-methoxy-1-methyl-ethylamino]-pyrimidin-4-yl}-3-(2,3,6-trifluorophenyl)-urea;
1-Phenyl-1-{2-[(1S)-2-methoxy-1-methyl-ethylamino]-pyrimidin-4-yl}-3-(2,4,5-trifluorophenyl)-urea;
1-Phenyl-1-{2-[(1S)-2-methoxy-1-methyl-ethylamino]-pyrimidin-4-yl}-3-(2,4,6-trifluorophenyl)-urea;
1-Phenyl-1-{2-[(1S)-2-methoxy-1-methyl-ethylamino]-pyrimidin-4-yl}-3-(3-chlorophenyl)-urea;
1-Phenyl-1-{2-[(1S)-2-methoxy-1-methyl-ethylamino]-pyrimidin-4-yl}-3-(4-chlorophenyl)-urea;
1-Phenyl-1-{2-[(1S)-2-methoxy-1-methyl-ethylamino]-pyrimidin-4-yl}-3-(2,3-dichlorophenyl)-urea;
1-Phenyl-1-{2-[(1S)-2-methoxy-1-methyl-ethylamino]-pyrimidin-4-yl}-3-(2,4-dichlorophenyl)-urea;
1-Phenyl-1-{2-[(1S)-2-methoxy-1-methyl-ethylamino]-pyrimidin-4-yl}-3-(2,5-dichlorophenyl)-urea;
1-Phenyl-1-{2-[(1S)-2-methoxy-1-methyl-ethylamino]-pyrimidin-4-yl}-3-(2,6-dichlorophenyl)-urea;
1-Phenyl-1-{2-[(1S)-2-methoxy-1-methyl-ethylamino]-pyrimidin-4-yl}-3-(2,3,4-trichlorophenyl)-urea;
1-Phenyl-1-{2-[(1S)-2-methoxy-1-methyl-ethylamino]-pyrimidin-4-yl}-3-(2,3,5-trichlorophenyl)-urea;
1-Phenyl-1-{2-[(1S)-2-methoxy-1-methyl-ethylamino]-pyrimidin-4-yl}-3-(2,3,6-trichlorophenyl)-urea;
1-Phenyl-1-{2-[(1S)-2-methoxy-1-methyl-ethylamino]-pyrimidin-4-yl}-3-(2,4,5-trichlorophenyl)-urea;
1-Phenyl-1-{2-[(1S)-2-methoxy-1-methyl-ethylamino]-pyrimidin-4-yl}-3-(2,4,6-trichlorophenyl)-urea;
1-(4-Fluorophenyl)-1-{2-[(1S)-2-methoxy-1-methyl-ethylamino]-pyrimidin-4-yl}-3-m-tolyl-urea;
1-(4-Fluorophenyl)-1-{2-[(1S)-2-methoxy-1-methyl-ethylamino]-pyrimidin-4-yl}-3-p-tolyl-urea;
1-(4-Fluorophenyl)-1-{2-[(1S)-2-methoxy-1-methyl-ethylamino]-pyrimidin-4-yl}-3-(3-fluorophenyl)-urea;
1-(4-Fluorophenyl)-1-{2-[(1S)-2-methoxy-1-methyl-ethylamino]-pyrimidin-4-yl}-3-(4-fluorophenyl)-urea;
1-(4-Fluorophenyl)-1-{2-[(1S)-2-methoxy-1-methyl-ethylamino]-pyrimidin-4-yl}-3-(2,3-difluorophenyl)-urea;
1-(4-Fluorophenyl)-1-{2-[(1S)-2-methoxy-1-methyl-ethylamino]-pyrimidin-4-yl}-3-(2,4-difluorophenyl)-urea;
1-(4-Fluorophenyl)-1-{2-[(1S)-2-methoxy-1-methyl-ethylamino]-pyrimidin-4-yl}-3-(2,5-difluorophenyl)-urea;
1-(4-Fluorophenyl)-1-{2-[(1S)-2-methoxy-1-methyl-ethylamino]-pyrimidin-4-yl}-3-(2,6-difluorophenyl)-urea;
1-(4-Fluorophenyl)-1-{2-[(1S)-2-methoxy-1-methyl-ethylamino]-pyrimidin-4-yl}-3-(2,3,4-trifluorophenyl)-urea;
1-(4-Fluorophenyl)-1-{2-[(1S)-2-methoxy-1-methyl-ethylamino]-pyrimidin-4-yl}-3-(2,3,5-trifluorophenyl)-urea;
1-(4-Fluorophenyl)-1-{2-[(1S)-2-methoxy-1-methyl-ethylamino]-pyrimidin-4-yl}-3-(2,3,6-trifluorophenyl)-urea;
1-(4-Fluorophenyl)-1-{2-[(1S)-2-methoxy-1-methyl-ethylamino]-pyrimidin-4-yl}-3-(2,4,5-trifluorophenyl)-urea;
1-(4-Fluorophenyl)-1-{2-[(1S)-2-methoxy-1-methyl-ethylamino]-pyrimidin-4-yl}-3-(2,4,6-trifluorophenyl)-urea;
1-(4-Fluorophenyl)-1-{2-[(1S)-2-methoxy-1-methyl-ethylamino]-pyrimidin-4-yl}-3-(3-chlorophenyl)-urea;
1-(4-Fluorophenyl)-1-{2-[(1S)-2-methoxy-1-methyl-ethylamino]-pyrimidin-4-yl}-3-(4-chlorophenyl)-urea;
1-(4-Fluorophenyl)-1-{2-[(1S)-2-methoxy-1-methyl-ethylamino]-pyrimidin-4-yl}-3-(2,3-dichlorophenyl)-urea;
1-(4-Fluorophenyl)-1-{2-[(1S)-2-methoxy-1-methyl-ethylamino]-pyrimidin-4-yl}-3-(2,4-dichlorophenyl)-urea;
1-(4-Fluorophenyl)-1-{2-[(1S)-2-methoxy-1-methyl-ethylamino]-pyrimidin-4-yl}-3-(2,5-dichlorophenyl)-urea;
1-(4-Fluorophenyl)-1-{2-[(1S)-2-methoxy-1-methyl-ethylamino]-pyrimidin-4-yl}-3-(2,3,4-trichlorophenyl)-urea;
1-(4-Fluorophenyl)-1-{2-[(1S)-2-methoxy-1-methyl-ethylamino]-pyrimidin-4-yl}-3-(2,3,5-trichlorophenyl)-urea;
1-(4-Fluorophenyl)-1-{2-[(1S)-2-methoxy-1-methyl-ethylamino]-pyrimidin-4-yl}-3-(2,3,6-trichlorophenyl)-urea;
1-(4-Fluorophenyl)-1-{2-[(1S)-2-methoxy-1-methyl-ethylamino]-pyrimidin-4-yl}-3-(2,4,5-trichlorophenyl)-urea;
1-(4-Fluorophenyl)-1-{2-[(1S)-2-methoxy-1-methyl-ethylamino]-pyrimidin-4-yl}-3-(2,4,6-trichlorophenyl)-urea;
1-(4-Methoxyphenyl)-1-{2-[(1S)-2-methoxy-1-methyl-ethylamino]-pyrimidin-4-yl}-3-m-tolyl-urea;
1-(4-Methoxyphenyl)-1-{2-[(1S)-2-methoxy-1-methyl-ethylamino]-pyrimidin-4-yl}-3-p-tolyl-urea;
1-(4-Methoxyphenyl)-1-{2-[(1S)-2-methoxy-1-methyl-ethylamino]-pyrimidin-4-yl}-3-(2-fluorophenyl)-urea;
1-(4-Methoxyphenyl)-1-{2-[(1S)-2-methoxy-1-methyl-ethylamino]-pyrimidin-4-yl}-3-(3-fluorophenyl)-urea;
1-(4-Methoxyphenyl)-1-{2-[(1S)-2-methoxy-1-methyl-ethylamino]-pyrimidin-4-yl}-3-(4-fluorophenyl)-urea;
1-(4-Methoxyphenyl)-1-{2-[(1S)-2-methoxy-1-methyl-ethylamino]-pyrimidin-4-yl}-3-(2,3-difluorophenyl)-urea;
1-(4-Methoxyphenyl)-1-{2-[(1S)-2-methoxy-1-methyl-ethylamino]-pyrimidin-4-yl}-3-(2,4-difluorophenyl)-urea;
1-(4-Methoxyphenyl)-1-{2-[(1S)-2-methoxy-1-methyl-ethylamino]-pyrimidin-4-yl}-3-(2,5-difluorophenyl)-urea;
1-(4-Methoxyphenyl)-1-{2-[(1S)-2-methoxy-1-methyl-ethylamino]-pyrimidin-4-yl}-3-(2,6-difluorophenyl)-urea;
1-(4-Methoxyphenyl)-1-{2-[(1S)-2-methoxy-1-methyl-ethylamino]-pyrimidin-4-yl}-3-(2,3,4-trifluorophenyl)-urea;
1-(4-Methoxyphenyl)-1-{2-[(1S)-2-methoxy-1-methyl-ethylamino]-pyrimidin-4-yl}-3-(2,3,5-trifluorophenyl)-urea;
1-(4-Methoxyphenyl)-1-{2-[(1S)-2-methoxy-1-methyl-ethylamino]-pyrimidin-4-yl}-3-(2,3,6-trifluorophenyl)-urea;

1-(4-Methoxyphenyl)-1-{2-[(1S)-2-methoxy-1-methyl-ethylamino]-pyrimidin-4-yl}-3-(2,4,5-trifluorophenyl)-urea;
1-(4-Methoxyphenyl)-1-{2-[(1S)-2-methoxy-1-methyl-ethylamino]-pyrimidin-4-yl}-3-(2,4,6-trifluorophenyl)-urea;
1-(4-Methoxyphenyl)-1-{2-[(1S)-2-methoxy-1-methyl-ethylamino]-pyrimidin-4-yl}-3-(3-chlorophenyl)-urea;
1-(4-Methoxyphenyl)-1-{2-[(1S)-2-methoxy-1-methyl-ethylamino]-pyrimidin-4-yl}-3-(4-chlorophenyl)-urea;
1-(4-Methoxyphenyl)-1-{2-[(1S)-2-methoxy-1-methyl-ethylamino]-pyrimidin-4-yl}-3-(2,3-dichlorophenyl)-urea;
1-(4-Methoxyphenyl)-1-{2-[(1S)-2-methoxy-1-methyl-ethylamino]-pyrimidin-4-yl}-3-(2,4-dichlorophenyl)-urea;
1-(4-Methoxyphenyl)-1-{2-[(1S)-2-methoxy-1-methyl-ethylamino]-pyrimidin-4-yl}-3-(2,5-dichlorophenyl)-urea;
1-(4-Methoxyphenyl)-1-{2-[(1S)-2-methoxy-1-methyl-ethylamino]-pyrimidin-4-yl}-3-(2,6-dichlorophenyl)-urea;
1-(4-Methoxyphenyl)-1-{2-[(1S)-2-methoxy-1-methyl-ethylamino]-pyrimidin-4-yl}-3-(2,3,4-trichlorophenyl)-urea;
1-(4-Methoxyphenyl)-1-{2-[(1S)-2-methoxy-1-methyl-ethylamino]-pyrimidin-4-yl}-3-(2,3,5-trichlorophenyl)-urea;
1-(4-Methoxyphenyl)-1-{2-[(1S)-2-methoxy-1-methyl-ethylamino]-pyrimidin-4-yl}-3-(2,3,6-trichlorophenyl)-urea;
1-(4-Methoxyphenyl)-1-{2-[(1S)-2-methoxy-1-methyl-ethylamino]-pyrimidin-4-yl}-3-(2,4,5-trichlorophenyl)-urea; and
1-(4-Methoxyphenyl)-1-{2-[(1S)-2-methoxy-1-methyl-ethylamino]-pyrimidin-4-yl}-3-(2,4,6-trichlorophenyl)-urea.

Further non-limiting examples of the second iteration of the first aspect of Category I wherein the index x equals 1 includes:

1-(4-Fluorophenyl)-1-{2-[(1S)-2-methoxy-1-methyl-ethylamino]-pyrimidin-4-yl}-3-m-methylbenzyl-urea;
1-(4-Fluorophenyl)-1-{2-[(1S)-2-methoxy-1-methyl-ethylamino]-pyrimidin-4-yl}-3-p-methylbenzyl-urea;
1-(4-Fluorophenyl)-1-{2-[(1S)-2-methoxy-1-methyl-ethylamino]-pyrimidin-4-yl}-3-(2-fluorobenzyl)-urea;
1-(4-Fluorophenyl)-1-{2-[(1S)-2-methoxy-1-methyl-ethylamino]-pyrimidin-4-yl}-3-(3-fluorobenzyl)-urea;
1-(4-Fluorophenyl)-1-{2-[(1S)-2-methoxy-1-methyl-ethylamino]-pyrimidin-4-yl}-3-(4-fluorobenzyl)-urea;
1-(4-Fluorophenyl)-1-{2-[(1S)-2-methoxy-1-methyl-ethylamino]-pyrimidin-4-yl}-3-(2,3-difluorobenzyl)-urea;
1-(4-Fluorophenyl)-1-{2-[(1S)-2-methoxy-1-methyl-ethylamino]-pyrimidin-4-yl}-3-(2,4-difluorobenzyl)-urea;
1-(4-Fluorophenyl)-1-{2-[(1S)-2-methoxy-1-methyl-ethylamino]-pyrimidin-4-yl}-3-(2,5-difluorobenzyl)-urea;
1-(4-Fluorophenyl)-1-{2-[(1S)-2-methoxy-1-methyl-ethylamino]-pyrimidin-4-yl}-3-(2,6-difluorobenzyl)-urea;
1-(4-Fluorophenyl)-1-{2-[(1S)-2-methoxy-1-methyl-ethylamino]-pyrimidin-4-yl}-3-(2,3,4-trifluorobenzyl)-urea;
1-(4-Fluorophenyl)-1-{2-[(1S)-2-methoxy-1-methyl-ethylamino]-pyrimidin-4-yl}-3-(2,3,5-trifluorobenzyl)-urea;
1-(4-Fluorophenyl)-1-{2-[(1S)-2-methoxy-1-methyl-ethylamino]-pyrimidin-4-yl}-3-(2,3,6-trifluorobenzyl)-urea;
1-(4-Fluorophenyl)-1-{2-[(1S)-2-methoxy-1-methyl-ethylamino]-pyrimidin-4-yl}-3-(2,4,5-trifluorobenzyl)-urea;
1-(4-Fluorophenyl)-1-{2-[(1S)-2-methoxy-1-methyl-ethylamino]-pyrimidin-4-yl}-3-(2,4,6-trifluorobenzyl)-urea;
1-(4-Fluorophenyl)-1-{2-[(1S)-2-methoxy-1-methyl-ethylamino]-pyrimidin-4-yl}-3-(3-chlorobenzyl)-urea;
1-(4-Fluorophenyl)-1-{2-[(1S)-2-methoxy-1-methyl-ethylamino]-pyrimidin-4-yl}-3-(4-chlorobenzyl)-urea;
1-(4-Fluorophenyl)-1-{2-[(1S)-2-methoxy-1-methyl-ethylamino]-pyrimidin-4-yl}-3-(2,3-dichlorobenzyl)-urea;
1-(4-Fluorophenyl)-1-{2-[(1S)-2-methoxy-1-methyl-ethylamino]-pyrimidin-4-yl}-3-(2,4-dichlorobenzyl)-urea;
1-(4-Fluorobenzyl)-1-{2-[(1S)-2-methoxy-1-methyl-ethylamino]-pyrimidin-4-yl}-3-(2,5-difluorophenyl)-urea;
1-(4-Fluorophenyl)-1-{2-[(1S)-2-methoxy-1-methyl-ethylamino]-pyrimidin-4-yl}-3-(2,6-dichlorobenzyl)-urea;
1-(4-Fluorophenyl)-1-{2-[(1S)-2-methoxy-1-methyl-ethylamino]-pyrimidin-4-yl}-3-(2,3,4-trichlorobenzyl)-urea;
1-(4-Fluorophenyl)-1-{2-[(1S)-2-methoxy-1-methyl-ethylamino]-pyrimidin-4-yl}-3-(2,3,5-trichlorobenzyl)-urea;
1-(4-Fluorophenyl)-1-{2-[(1S)-2-methoxy-1-methyl-ethylamino]-pyrimidin-4-yl}-3-(2,3,6-trichlorobenzyl)-urea;
1-(4-Fluorophenyl)-1-{2-[(1S)-2-methoxy-1-methyl-ethylamino]-pyrimidin-4-yl}-3-(2,4,5-trichlorobenzyl)-urea;
1-(4-Fluorophenyl)-1-{2-[(1S)-2-methoxy-1-methyl-ethylamino]-pyrimidin-4-yl}-3-(2,4,6-trichlorobenzyl)-urea;
1-(4-Methoxyphenyl)-1-{2-[(1S)-2-methoxy-1-methyl-ethylamino]-pyrimidin-4-yl}-3-(3-chlorobenzyl)-urea;
1-(4-Methoxyphenyl)-1-{2-[(1S)-2-methoxy-1-methyl-ethylamino]-pyrimidin-4-yl}-3-(4-chlorobenzyl)-urea;
1-(4-Methoxyphenyl)-1-{2-[(1S)-2-methoxy-1-methyl-ethylamino]-pyrimidin-4-yl}-3-(2,3-dichlorobenzyl)-urea;
1-(4-Methoxyphenyl)-1-{2-[(1S)-2-methoxy-1-methyl-ethylamino]-pyrimidin-4-yl}-3-(2,4-dichlorobenzyl)-urea;
1-(4-Methoxybenzyl)-1-{2-[(1S)-2-methoxy-1-methyl-ethylamino]-pyrimidin-4-yl}-3-(2,5-difluorophenyl)-urea;
1-(4-Methoxyphenyl)-1-{2-[(1S)-2-methoxy-1-methyl-ethylamino]-pyrimidin-4-yl}-3-(2,6-dichlorobenzyl)-urea;

1-(4-Methoxyphenyl)-1-{2-[(1S)-2-methoxy-1-methyl-ethylamino]-pyrimidin-4-yl}-3-(2,3,4-trichlorobenzyl)-urea;

1-(4-Methoxyphenyl)-1-{2-[(1S)-2-methoxy-1-methyl-ethylamino]-pyrimidin-4-yl}-3-(2,3,5-trichlorobenzyl)-urea;

1-(4-Methoxyphenyl)-1-{2-[(1S)-2-methoxy-1-methyl-ethylamino]-pyrimidin-4-yl}-3-(2,3,6-trichlorobenzyl)-urea;

1-(4-Methoxyphenyl)-1-{2-[(1S)-2-methoxy-1-methyl-ethylamino]-pyrimidin-4-yl}-3-(2,4,5-trichlorobenzyl)-urea; and 1-(4-Methoxyphenyl)-1-{2-[(1S)-2-methoxy-1-methyl-ethylamino]-pyrimidin-4-yl}-3-(2,4,6-trichlorobenzyl)-urea.

The third iteration of the first aspect of Category I includes compounds having the formula:

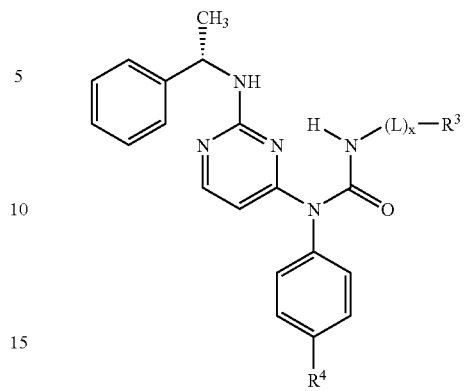

wherein non-limiting examples of L, $R^3$, and $R^4$ are defined herein below in Table III. In Table III, compounds 401-500 have x equal to 0; for compounds 501-600 x is equal to 1 and the L unit is defined therein.

TABLE III

| No. | $R^4$ | $R^3$ | No. | $R^4$ | L | $R^3$ |
|---|---|---|---|---|---|---|
| 401 | —H | 2-fluorophenyl | 501 | —H | —$CH_2$— | 2-fluorophenyl |
| 402 | —H | 3-fluorophenyl | 502 | —H | —$CH_2$— | 3-fluorophenyl |
| 403 | —H | 4-fluorophenyl | 503 | —H | —$CH_2$— | 4-fluorophenyl |
| 404 | —H | 2,6-difluorophenyl | 504 | —H | —$CH_2$— | 2,6-difluorophenyl |
| 405 | —H | 2-chlorophenyl | 505 | —H | —$CH_2$— | 2-chlorophenyl |
| 406 | —H | 3-chlorophenyl | 506 | —H | —$CH_2$— | 3-chlorophenyl |
| 407 | —H | 4-chlorophenyl | 507 | —H | —$CH_2$— | 4-chlorophenyl |
| 408 | —H | 3,4-dichlorophenyl | 508 | —H | —$CH_2$— | 3,4-dichlorophenyl |
| 409 | —H | 2,4-dichlorophenyl | 509 | —H | —$CH_2$— | 2,4-dichlorophenyl |
| 410 | —H | 2,6-dichlorophenyl | 510 | —H | —$CH_2$— | 2,6-dichlorophenyl |
| 411 | —H | 2-methylphenyl | 511 | —H | —$CH_2$— | 2-methylphenyl |
| 412 | —H | 3-methylphenyl | 512 | —H | —$CH_2$— | 3-methylphenyl |
| 413 | —H | 4-methylphenyl | 513 | —H | —$CH_2$— | 4-methylphenyl |
| 414 | —H | 2,4-dimethylphenyl | 514 | —H | —$CH_2$— | 2,4-dimethylphenyl |
| 415 | —H | 2,6-dimethylphenyl | 515 | —H | —$CH_2$— | 2,6-dimethylphenyl |
| 416 | —H | 2-methoxyphenyl | 516 | —H | —$CH_2$— | 2-methoxyphenyl |
| 417 | —H | 3-methoxyphenyl | 517 | —H | —$CH_2$— | 3-methoxyphenyl |
| 418 | —H | 4-methoxyphenyl | 518 | —H | —$CH_2$— | 4-methoxyphenyl |
| 419 | —H | 3-($CF_3$)-phenyl | 519 | —H | —$CH_2$— | 3-($CF_3$)-phenyl |
| 420 | —H | 4-($CF_3$)-phenyl | 520 | —H | —$CH_2$— | 4-($CF_3$)-phenyl |
| 421 | —F | 2-fluorophenyl | 521 | —F | —$CH_2$— | 2-fluorophenyl |
| 422 | —F | 3-fluorophenyl | 522 | —F | —$CH_2$— | 3-fluorophenyl |
| 423 | —F | 4-fluorophenyl | 523 | —F | —$CH_2$— | 4-fluorophenyl |
| 424 | —F | 2,6-difluorophenyl | 524 | —F | —$CH_2$— | 2,6-difluorophenyl |
| 425 | —F | 2-chlorophenyl | 525 | —F | —$CH_2$— | 2-chlorophenyl |
| 426 | —F | 3-chlorophenyl | 526 | —F | —$CH_2$— | 3-chlorophenyl |
| 427 | —F | 4-chlorophenyl | 527 | —F | —$CH_2$— | 4-chlorophenyl |
| 428 | —F | 3,4-dichlorophenyl | 528 | —F | —$CH_2$— | 3,4-dichlorophenyl |
| 429 | —F | 2,4-dichlorophenyl | 529 | —F | —$CH_2$— | 2,4-dichlorophenyl |
| 430 | —F | 2,6-dichlorophenyl | 530 | —F | —$CH_2$— | 2,6-dichlorophenyl |
| 431 | —F | 2-methylphenyl | 531 | —F | —$CH_2$— | 2-methylphenyl |
| 432 | —F | 3-methylphenyl | 532 | —F | —$CH_2$— | 3-methylphenyl |

TABLE III-continued

| No. | R⁴ | R³ | No. | R⁴ | L | R³ |
|---|---|---|---|---|---|---|
| 433 | —F | 4-methylphenyl | 533 | —F | —CH₂— | 4-methylphenyl |
| 434 | —F | 2,4-dimethylphenyl | 534 | —F | —CH₂— | 2,4-dimethylphenyl |
| 435 | —F | 2,6-dimethylphenyl | 535 | —F | —CH₂— | 2,6-dimethylphenyl |
| 436 | —F | 2-methoxyphenyl | 536 | —F | —CH₂— | 2-methoxyphenyl |
| 437 | —F | 3-methoxyphenyl | 537 | —F | —CH₂— | 3-methoxyphenyl |
| 438 | —F | 4-methoxyphenyl | 538 | —F | —CH₂— | 4-methoxyphenyl |
| 439 | —F | 3-(CF₃)-phenyl | 539 | —F | —CH₂— | 3-(CF₃)-phenyl |
| 440 | —F | 4-(CF₃)-phenyl | 540 | —F | —CH₂— | 4-(CF₃)-phenyl |
| 441 | —CH₃ | 2-fluorophenyl | 541 | —CH₃ | —CH₂— | 2-fluorophenyl |
| 442 | —CH₃ | 3-fluorophenyl | 542 | —CH₃ | —CH₂— | 3-fluorophenyl |
| 443 | —CH₃ | 4-fluorophenyl | 543 | —CH₃ | —CH₂— | 4-fluorophenyl |
| 444 | —CH₃ | 2,6-difluorophenyl | 544 | —CH₃ | —CH₂— | 2,6-difluorophenyl |
| 445 | —CH₃ | 2-chlorophenyl | 545 | —CH₃ | —CH₂— | 2-chlorophenyl |
| 446 | —CH₃ | 3-chlorophenyl | 546 | —CH₃ | —CH₂— | 3-chlorophenyl |
| 447 | —CH₃ | 4-chlorophenyl | 547 | —CH₃ | —CH₂— | 4-chlorophenyl |
| 448 | —CH₃ | 3,4-dichlorophenyl | 548 | —CH₃ | —CH₂— | 3,4-dichlorophenyl |
| 449 | —CH₃ | 2,4-dichlorophenyl | 549 | —CH₃ | —CH₂— | 2,4-dichlorophenyl |
| 450 | —CH₃ | 2,6-dichlorophenyl | 550 | —CH₃ | —CH₂— | 2,6-dichlorophenyl |
| 451 | —CH₃ | 2-methylphenyl | 551 | —CH₃ | —CH₂— | 2-methylphenyl |
| 452 | —CH₃ | 3-methylphenyl | 552 | —CH₃ | —CH₂— | 3-methylphenyl |
| 453 | —CH₃ | 4-methylphenyl | 553 | —CH₃ | —CH₂— | 4-methylphenyl |
| 454 | —CH₃ | 2,4-dimethylphenyl | 554 | —CH₃ | —CH₂— | 2,4-dimethylphenyl |
| 455 | —CH₃ | 2,6-dimethylphenyl | 555 | —CH₃ | —CH₂— | 2,6-dimethylphenyl |
| 456 | —CH₃ | 2-methoxyphenyl | 556 | —CH₃ | —CH₂— | 2-methoxyphenyl |
| 457 | —CH₃ | 3-methoxyphenyl | 557 | —CH₃ | —CH₂— | 3-methoxyphenyl |
| 458 | —CH₃ | 4-methoxyphenyl | 558 | —CH₃ | —CH₂— | 4-methoxyphenyl |
| 459 | —CH₃ | 3-(CF₃)-phenyl | 559 | —CH₃ | —CH₂— | 3-(CF₃)-phenyl |
| 460 | —CH₃ | 4-(CF₃)-phenyl | 560 | —CH₃ | —CH₂— | 4-(CF₃)-phenyl |
| 461 | —OCH₃ | 2-fluorophenyl | 561 | —OCH₃ | —CH₂— | 2-fluorophenyl |
| 462 | —OCH₃ | 3-fluorophenyl | 562 | —OCH₃ | —CH₂— | 3-fluorophenyl |
| 463 | —OCH₃ | 4-fluorophenyl | 563 | —OCH₃ | —CH₂— | 4-fluorophenyl |
| 464 | —OCH₃ | 2,6-difluorophenyl | 564 | —OCH₃ | —CH₂— | 2,6-difluorophenyl |
| 465 | —OCH₃ | 2-chlorophenyl | 565 | —OCH₃ | —CH₂— | 2-chlorophenyl |
| 466 | —OCH₃ | 3-chlorophenyl | 566 | —OCH₃ | —CH₂— | 3-chlorophenyl |
| 467 | —OCH₃ | 4-chlorophenyl | 567 | —OCH₃ | —CH₂— | 4-chlorophenyl |
| 468 | —OCH₃ | 3,4-dichlorophenyl | 568 | —OCH₃ | —CH₂— | 3,4-dichlorophenyl |
| 469 | —OCH₃ | 2,4-dichlorophenyl | 569 | —OCH₃ | —CH₂— | 2,4-dichlorophenyl |
| 470 | —OCH₃ | 2,6-dichlorophenyl | 570 | —OCH₃ | —CH₂— | 2,6-dichlorophenyl |
| 471 | —OCH₃ | 2-methylphenyl | 571 | —OCH₃ | —CH₂— | 2-methylphenyl |
| 472 | —OCH₃ | 3-methylphenyl | 572 | —OCH₃ | —CH₂— | 3-methylphenyl |
| 473 | —OCH₃ | 4-methylphenyl | 573 | —OCH₃ | —CH₂— | 4-methylphenyl |
| 474 | —OCH₃ | 2,4-dimethylphenyl | 574 | —OCH₃ | —CH₂— | 2,4-dimethylphenyl |
| 475 | —OCH₃ | 2,6-dimethylphenyl | 575 | —OCH₃ | —CH₂— | 2,6-dimethylphenyl |
| 476 | —OCH₃ | 2-methoxyphenyl | 576 | —OCH₃ | —CH₂— | 2-methoxyphenyl |
| 477 | —OCH₃ | 3-methoxyphenyl | 577 | —OCH₃ | —CH₂— | 3-methoxyphenyl |
| 478 | —OCH₃ | 4-methoxyphenyl | 578 | —OCH₃ | —CH₂— | 4-methoxyphenyl |
| 479 | —OCH₃ | 3-(CF₃)-phenyl | 579 | —OCH₃ | —CH₂— | 3-(CF₃)-phenyl |
| 480 | —OCH₃ | 4-(CF₃)-phenyl | 580 | —OCH₃ | —CH₂— | 4-(CF₃)-phenyl |
| 481 | —SCH₃ | 2-fluorophenyl | 581 | —SCH₃ | —CH₂— | 2-fluorophenyl |
| 482 | —SCH₃ | 3-fluorophenyl | 582 | —SCH₃ | —CH₂— | 3-fluorophenyl |
| 483 | —SCH₃ | 4-fluorophenyl | 583 | —SCH₃ | —CH₂— | 4-fluorophenyl |
| 484 | —SCH₃ | 2,6-difluorophenyl | 584 | —SCH₃ | —CH₂— | 2,6-difluorophenyl |
| 485 | —SCH₃ | 2-chlorophenyl | 585 | —SCH₃ | —CH₂— | 2-chlorophenyl |
| 486 | —SCH₃ | 3-chlorophenyl | 586 | —SCH₃ | —CH₂— | 3-chlorophenyl |
| 487 | —SCH₃ | 4-chlorophenyl | 587 | —SCH₃ | —CH₂— | 4-chlorophenyl |
| 488 | —SCH₃ | 3,4-dichlorophenyl | 588 | —SCH₃ | —CH₂— | 3,4-dichlorophenyl |
| 489 | —SCH₃ | 2,4-dichlorophenyl | 589 | —SCH₃ | —CH₂— | 2,4-dichlorophenyl |
| 490 | —SCH₃ | 2,6-dichlorophenyl | 590 | —SCH₃ | —CH₂— | 2,6-dichlorophenyl |
| 491 | —SCH₃ | 2-methylphenyl | 591 | —SCH₃ | —CH₂— | 2-methylphenyl |
| 492 | —SCH₃ | 3-methylphenyl | 592 | —SCH₃ | —CH₂— | 3-methylphenyl |
| 493 | —SCH₃ | 4-methylphenyl | 593 | —SCH₃ | —CH₂— | 4-methylphenyl |
| 494 | —SCH₃ | 2,4-dimethylphenyl | 594 | —SCH₃ | —CH₂— | 2,4-dimethylphenyl |
| 495 | —SCH₃ | 2,6-dimethylphenyl | 595 | —SCH₃ | —CH₂— | 2,6-dimethylphenyl |
| 496 | —SCH₃ | 2-methoxyphenyl | 596 | —SCH₃ | —CH₂— | 2-methoxyphenyl |
| 497 | —SCH₃ | 3-methoxyphenyl | 597 | —SCH₃ | —CH₂— | 3-methoxyphenyl |
| 498 | —SCH₃ | 4-methoxyphenyl | 598 | —SCH₃ | —CH₂— | 4-methoxyphenyl |
| 499 | —SCH₃ | 3-(CF₃)-phenyl | 599 | —SCH₃ | —CH₂— | 3-(CF₃)-phenyl |
| 500 | —SCH₃ | 4-(CF₃)-phenyl | 600 | —SCH₃ | —CH₂— | 4-(CF₃)-phenyl |

The following are further non-limiting examples of compounds which comprise the third iteration of the first aspect of Category I according to the present invention.

1-(2-Fluorophenyl)-1-{2-[(1S)-1-phenyl-ethylamino]-pyrimidin-4-yl}-3-(2-chlorophenyl)-urea: $^1$H NMR (300 MHz, CDCl$_3$) δ 13.02 (s, 1H), 8.39 (br s, 1H), 8.04 (d, J=6.0 Hz, 1H), 7.53-7.25 (m, 11H), 7.06 (dt, J=1.5, 7.8 Hz, 1H), 5.63 (d, J=7.8 Hz, 1H), 5.57 (d, J=6.0 Hz, 1H), 5.32-5.24 (m, 1H), 1.63 (d, J=6.6 Hz, 3H); MS (ESI) m/z 462 (M+1).

1-(3-Fluorophenyl)-1-{2-[(1S)-1-phenyl-ethylamino]-pyrimidin-4-yl}-3-(2-chlorophenyl)-urea: $^1$H NMR (300 MHz, CDCl$_3$) δ 8.36 (br s, 1H), 8.03 (d, J=6.0 Hz, 1H), 7.56-7.04 (m, 12H), 5.65 (d, J=7.8 Hz, 1H), 5.53 (d, J=5.7 Hz, 1H), 5.32-5.24 (m, 1H), 1.63 (d, J=6.9 Hz, 3H); MS (ESI) m/z 462 (M+1).

1-(4-Fluorophenyl)-1-{2-[(1S)-1-phenyl-ethylamino]-pyrimidin-4-yl}-3-(2-chlorophenyl)-urea: $^1$H NMR (300 MHz, CDCl$_3$) δ 8.35 (br s, 1H), 8.00 (d, J=5.7 Hz, 1H), 7.44 (dd, J=1.5, 8.1 Hz, 1H), 7.41-7.19 (m, 11H), 7.06 (dt, J=1.5, 8.1 Hz, 1H), 5.60(d, J=7.8 Hz, 1H), 5.51 (d, J=6.0 Hz, 1H), 5.30-5.21 (m, 1H), 1.61 (d, J=6.6 Hz, 3H); MS (ESI) m/z 462 (M+1).

1-(4-Fluorophenyl)-1-{2-[(1S)-1-phenyl-ethylamino]-pyrimidin-4-yl}-3-phenyl-urea: $^1$H NMR (300 MHz, CDCl$_3$) δ 12.10 (br s, 1H), 7.93 (d, J=5.9 Hz, 1H), 7.47-7.29 (m, 9H), 7.10 (d, J=8.8 Hz, 2H), 7.12-7.06 (m, 1H), 6.80 (d, J=8.8 Hz, 2H), 5.69 (d, J=5.9 Hz, 1H), 5.52 (m, 1H), 5.28 (m, 1H), 3.02 (s, 6H), 1.67 (d, J=6.8 Hz, 3H); MS (ESI) m/z 453 (M+1).

1-(4-Dimethylaminophenyl)-1-{2-[(1S)-1-phenyl-ethylamino]-pyrimidin-4-yl}-3-(2-chlorophenyl)-urea: $^1$H NMR (300 MHz, CDCl$_3$) δ 13.05 (br s, 1H), 8.43 (br d, J=7.5 Hz, 1H), 7.98 (d, J=5.8 Hz, 1H), 7.44-7.24 (m, 7H), 7.11 (d, J=8.8 Hz, 2H), 7.03 (t, J=7.8 Hz, 1H), 6.82 (d, J=8.8 Hz, 2H), 5.67 (d, J=5.8 Hz, 1H), 5.56 (d, J=7.8 Hz, 1H), 5.26 (m, 1H), 3.03 (s, 6H), 1.61 (d, J=6.9 Hz, 3H); MS (ESI) m/z 487 (M+1).

1-(4-Dimethylaminophenyl)-1-{2-[(1S)-1-phenyl-ethylamino]-pyrimidin-4-yl}-3-o-tolyl-urea: $^1$H NMR (300 MHz, CDCl$_3$) δ 7.97 (d, J=5.8 Hz, 1H), 7.95 (br s, 1H), 7.30-7.19 (m, 8H), 7.09 (d, J=8.8 Hz, 2H), 7.06 (m, 1H), 6.79 (d, J=8.8 Hz, 2H), 5.74 (d, J=5.8 Hz, 1H), 5.26 (m, 1H), 5.15 (m, 1H), 3.02 (s, 6H), 1.58 (d, J=6.9 Hz, 3H); MS (ESI) m/z 467 (M+1).

Further non-limiting examples of the third iteration of the first aspect of Category I wherein the index x equals 0 includes:

1-(2-Fluorophenyl)-1-{2-[(1S)-1-phenyl-ethylamino]-pyrimidin-4-yl}-3-phenyl-urea;
1-(3-Fluorophenyl)-1-{2-[(1S)-1-phenyl-ethylamino]-pyrimidin-4-yl}-3-phenyl-urea;
1-(4-Fluorophenyl)-1-{2-[(1S)-1-phenyl-ethylamino]-pyrimidin-4-yl}-3-phenyl-urea;
1-(2-Fluorophenyl)-1-{2-[(1S)-1-phenyl-ethylamino]-pyrimidin-4-yl}-3-(3-fluorophenyl)-urea;
1-(2-Fluorophenyl)-1-{2-[(1S)-1-phenyl-ethylamino]-pyrimidin-4-yl}-3-(4-fluorophenyl)-urea;
1-(2-Fluorophenyl)-1-{2-[(1S)-1-phenyl-ethylamino]-pyrimidin-4-yl}-3-(2,6-difluorophenyl)-urea;
1-(3-Fluorophenyl)-1-{2-[(1S)-1-phenyl-ethylamino]-pyrimidin-4-yl}-3-(3-fluorophenyl)-urea;
1-(3-Fluorophenyl)-1-{2-[(1S)-1-phenyl-ethylamino]-pyrimidin-4-yl}-3-(4-fluorophenyl)-urea;
1-(3-Fluorophenyl)-1-{2-[(1S)-1-phenyl-ethylamino]-pyrimidin-4-yl}-3-(2,6-difluorophenyl)-urea;
1-(4-Fluorophenyl)-1-{2-[(1S)-1-phenyl-ethylamino]-pyrimidin-4-yl}-3-(2-fluorophenyl)-urea;
1-(4-Fluorophenyl)-1-{2-[(1S)-1-phenyl-ethylamino]-pyrimidin-4-yl}-3-(3-fluorophenyl)-urea;
1-(4-Fluorophenyl)-1-{2-[(1S)-1-phenyl-ethylamino]-pyrimidin-4-yl}-3-(4-fluorophenyl)-urea;
1-(4-Fluorophenyl)-1-{2-[(1S)-1-phenyl-ethylamino]-pyrimidin-4-yl}-3-(2,6-difluorophenyl)-urea;
1-(2-Fluorophenyl)-1-{2-[(1S)-1-phenyl-ethylamino]-pyrimidin-4-yl}-3-(3-chlorophenyl)-urea;
1-(2-Fluorophenyl)-1-{2-[(1S)-1-phenyl-ethylamino]-pyrimidin-4-yl}-3-(4-chlorophenyl)-urea;
1-(2-Fluorophenyl)-1-{2-[(1S)-1-phenyl-ethylamino]-pyrimidin-4-yl}-3-(2,6-dichlorophenyl)-urea;
1-(3-Fluorophenyl)-1-{2-[(1S)-1-phenyl-ethylamino]-pyrimidin-4-yl}-3-(3-chlorophenyl)-urea;
1-(3-Fluorophenyl)-1-{2-[(1S)-1-phenyl-ethylamino]-pyrimidin-4-yl}-3-(4-chlorophenyl)-urea;
1-(3-Fluorophenyl)-1-{2-[(1S)-1-phenyl-ethylamino]-pyrimidin-4-yl}-3-(2,6-dichlorophenyl)-urea;
1-(4-Fluorophenyl)-1-{2-[(1S)-1-phenyl-ethylamino]-pyrimidin-4-yl}-3-(2-chlorophenyl)-urea;
1-(4-Fluorophenyl)-1-{2-[(1S)-1-phenyl-ethylamino]-pyrimidin-4-yl}-3-(3-chlorophenyl)-urea;
1-(4-Fluorophenyl)-1-{2-[(lS)-1-phenyl-ethylamino]-pyrimidin-4-yl}-3-(4-chlorophenyl)-urea;
1-(4-Fluorophenyl)-1-{2-[(1S)-1-phenyl-ethylamino]-pyrimidin-4-yl}-3-(2,6-dichlorophenyl)-urea;
1-(2-Dimethylaminophenyl)-1-{2-[(1S)-1-phenyl-ethylamino]-pyrimidin-4-yl}-3-phenyl-urea;
1-(3-Dimethylaminophenyl)-1-{2-[(1S)-1-phenyl-ethylamino]-pyrimidin-4-yl}-3-phenyl-urea;
1-(4-Dimethylaminophenyl)-1-{2-[(1S)-1-phenyl-ethylamino]-pyrimidin-4-yl}-3-phenyl-urea;
1-(2-Dimethylaminophenyl)-1-{2-[(1S)-1-phenyl-ethylamino]-pyrimidin-4-yl}-3-(3-fluorophenyl)-urea;
1-(2-Dimethylaminophenyl)-1-{2-[(1S)-1-phenyl-ethylamino]-pyrimidin-4-yl}-3-(4-fluorophenyl)-urea;
1-(2-Dimethylaminophenyl)-1-{2-[(1S)-1-phenyl-ethylamino]-pyrimidin-4-yl}-3-(2,6-difluorophenyl)-urea;
1-(3-Dimethylaminophenyl)-1-{2-[(1S)-1-phenyl-ethylamino]-pyrimidin-4-yl}-3-(3-fluorophenyl)-urea;
1-(3-Dimethylaminophenyl)-1-{2-[(1S)-1-phenyl-ethylamino]-pyrimidin-4-yl}-3-(4-fluorophenyl)-urea;
1-(3-Dimethylaminophenyl)-1-{2-[(1S)-1-phenyl-ethylamino]-pyrimidin-4-yl}-3-(2,6-difluorophenyl)-urea;
1-(4-Dimethylaminophenyl)-1-{2-[(S)-1-phenyl-ethylamino]-pyrimidin-4-yl}-3-(2-fluorophenyl)-urea;
1-(4-Dimethylaminophenyl)-1-{2-[(1S)-1-phenyl-ethylamino]-pyrimidin-4-yl}-3-(3-fluorophenyl)-urea;
1-(4-Dimethylaminophenyl)-1-{2-[(1S)-1-phenyl-ethylamino]-pyrimidin-4-yl}-3-(4-fluorophenyl)-urea;
1-(4-Dimethylaminophenyl)-1-{2-[(1S)-1-phenyl-ethylamino]-pyrimidin-4-yl}-3-(2,6-difluorophenyl)-urea;
1-(2-Dimethylaminophenyl)-1-{2-[(1S)-1-phenyl-ethylamino]-pyrimidin-4-yl}-3-(3-chlorophenyl)-urea;
1-(2-Dimethylaminophenyl)-1-{2-[(1S)-1-phenyl-ethylamino]-pyrimidin-4-yl}-3-(4-chlorophenyl)-urea;
1-(2-Dimethylaminophenyl)-1-{2-[(1S)-1-phenyl-ethylamino]-pyrimidin-4-yl}-3-(2,6-dichlorophenyl)-urea;
1-(3-Dimethylaminophenyl)-1-{2-[(1S)-1-phenyl-ethylamino]-pyrimidin-4-yl}-3-(3-chlorophenyl)-urea;
1-(3-Dimethylaminophenyl)-1-{2-[(1S)-1-phenyl-ethylamino]-pyrimidin-4-yl}-3-(4-chlorophenyl)-urea;
1-(3-Dimethylaminophenyl)-1-{2-[(1S)-1-phenyl-ethylamino]-pyrimidin-4-yl}-3-(2,6-dichlorophenyl)-urea;
1-(4-Dimethylaminophenyl)-1-{2-[(1S)-1-phenyl-ethylamino]-pyrimidin-4-yl}-3-(2-chlorophenyl)-urea;
1-(4-Dimethylaminophenyl)-1-{2-[(1S)-1-phenyl-ethylamino]-pyrimidin-4-yl}-3-(3-chlorophenyl)-urea;

1-(4-Dimethylaminophenyl)-1-{2-[(1S)-1-phenyl-ethy-lamino]-pyrimidin-4-yl}-3-(4-chlorophenyl)-urea;
1-(4-Dimethylaminophenyl)-1-{2-[(1S)-1-phenyl-ethy-lamino]-pyrimidin-4-yl}-3-(2,6-dichlorophenyl)-urea;
1-(2-Dimethylaminophenyl)-1-{2-[(1S)-1-phenyl-ethy-lamino]-pyrimidin-4-yl}-3-o-tolyl-urea;
1-(2-Dimethylaminophenyl)-1-{2-[(1S)-1-phenyl-ethy-lamino]-pyrimidin-4-yl}-3-m-tolyl-urea;
1-(2-Dimethylaminophenyl)-1-{2-[(1S)-1-phenyl-ethy-lamino]-pyrimidin-4-yl}-3-p-tolyl-urea;
1-(3-Dimethylaminophenyl)-1-{2-[(1S)-1-phenyl-ethy-lamino]-pyrimidin-4-yl}-3-o-tolyl-urea;
1-(3-Dimethylaminophenyl)-1-{2-[(1S)-1-phenyl-ethy-lamino]-pyrimidin-4-yl}-3-m-tolyl-urea;
1-(3-Dimethylaminophenyl)-1-{2-[(1S)-1-phenyl-ethy-lamino]-pyrimidin-4-yl}-3-p-tolyl-urea;
1-(4-Dimethylaminophenyl)-1-{2-[(1S)-1-phenyl-ethy-lamino]-pyrimidin-4-yl}-3-m-tolyl-urea; and
1-(4-Dimethylaminophenyl)-1-{2-[(1S)-1-phenyl-ethy-lamino]-pyrimidin-4-yl}-3-p-tolyl-urea.

The fourth iteration of Category I relates to compounds having the formula:

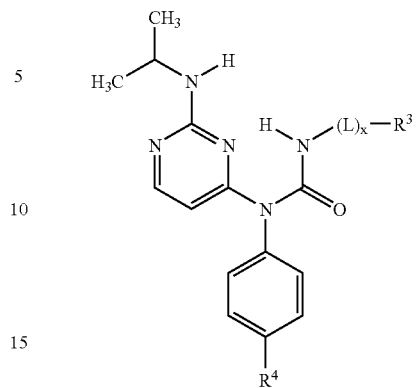

wherein non-limiting examples of L, $R^3$, and $R^4$ are defined herein below in Table IV. In Table III, compounds 601-700 have x equal to 0; for compounds 701-800 x is equal to 1 and the L unit is defined therein.

TABLE IV

| No. | $R^4$ | $R^3$ | No. | $R^4$ | L | $R^3$ |
|---|---|---|---|---|---|---|
| 601 | —H | 2-fluorophenyl | 701 | —H | —CH$_2$— | 2-fluorophenyl |
| 602 | —H | 3-fluorophenyl | 702 | —H | —CH$_2$— | 3-fluorophenyl |
| 603 | —H | 4-fluorophenyl | 703 | —H | —CH$_2$— | 4-fluorophenyl |
| 604 | —H | 2,6-difluorophenyl | 704 | —H | —CH$_2$— | 2,6-difluorophenyl |
| 605 | —H | 2-chlorophenyl | 705 | —H | —CH$_2$— | 2-chlorophenyl |
| 606 | —H | 3-chlorophenyl | 706 | —H | —CH$_2$— | 3-chlorophenyl |
| 607 | —H | 4-chlorophenyl | 707 | —H | —CH$_2$— | 4-chlorophenyl |
| 608 | —H | 3,4-dichlorophenyl | 708 | —H | —CH$_2$— | 3,4-dichlorophenyl |
| 609 | —H | 2,4-dichlorophenyl | 709 | —H | —CH$_2$— | 2,4-dichlorophenyl |
| 610 | —H | 2,6-dichlorophenyl | 710 | —H | —CH$_2$— | 2,6-dichlorophenyl |
| 611 | —H | 2-methylphenyl | 711 | —H | —CH$_2$— | 2-methylphenyl |
| 612 | —H | 3-methylphenyl | 712 | —H | —CH$_2$— | 3-methylphenyl |
| 613 | —H | 4-methylphenyl | 713 | —H | —CH$_2$— | 4-methylphenyl |
| 614 | —H | 2,4-dimethylphenyl | 714 | —H | —CH$_2$— | 2,4-dimethylphenyl |
| 615 | —H | 2,6-dimethylphenyl | 715 | —H | —CH$_2$— | 2,6-dimethylphenyl |
| 616 | —H | 2-methoxyphenyl | 716 | —H | —CH$_2$— | 2-methoxyphenyl |
| 617 | —H | 3-methoxyphenyl | 717 | —H | —CH$_2$— | 3-methoxyphenyl |
| 618 | —H | 4-methoxyphenyl | 718 | —H | —CH$_2$— | 4-methoxyphenyl |
| 619 | —H | 3-(CF$_3$)-phenyl | 719 | —H | —CH$_2$— | 3-(CF$_3$)-phenyl |
| 620 | —H | 4-(CF$_3$)-phenyl | 720 | —H | —CH$_2$— | 4-(CF$_3$)-phenyl |
| 621 | —F | 2-fluorophenyl | 721 | —F | —CH$_2$— | 2-fluorophenyl |
| 622 | —F | 3-fluorophenyl | 722 | —F | —CH$_2$— | 3-fluorophenyl |
| 623 | —F | 4-fluorophenyl | 723 | —F | —CH$_2$— | 4-fluorophenyl |
| 624 | —F | 2,6-difluorophenyl | 724 | —F | —CH$_2$— | 2,6-difluorophenyl |
| 625 | —F | 2-chlorophenyl | 725 | —F | —CH$_2$— | 2-chlorophenyl |
| 626 | —F | 3-chlorophenyl | 726 | —F | —CH$_2$— | 3-chlorophenyl |
| 627 | —F | 4-chlorophenyl | 727 | —F | —CH$_2$— | 4-chlorophenyl |
| 628 | —F | 3,4-dichlorophenyl | 728 | —F | —CH$_2$— | 3,4-dichlorophenyl |
| 629 | —F | 2,4-dichlorophenyl | 729 | —F | —CH$_2$— | 2,4-dichlorophenyl |
| 630 | —F | 2,6-dichlorophenyl | 730 | —F | —CH$_2$— | 2,6-dichlorophenyl |
| 631 | —F | 2-methylphenyl | 731 | —F | —CH$_2$— | 2-methylphenyl |
| 632 | —F | 3-methylphenyl | 732 | —F | —CH$_2$— | 3-methylphenyl |
| 633 | —F | 4-methylphenyl | 733 | —F | —CH$_2$— | 4-methylphenyl |
| 634 | —F | 2,4-dimethylphenyl | 734 | —F | —CH$_2$— | 2,4-dimethylphenyl |
| 635 | —F | 2,6-dimethylphenyl | 735 | —F | —CH$_2$— | 2,6-dimethylphenyl |
| 636 | —F | 2-methoxyphenyl | 736 | —F | —CH$_2$— | 2-methoxyphenyl |
| 637 | —F | 3-methoxyphenyl | 737 | —F | —CH$_2$— | 3-methoxyphenyl |
| 638 | —F | 4-methoxyphenyl | 738 | —F | —CH$_2$— | 4-methoxyphenyl |
| 639 | —F | 3-(CF$_3$)-phenyl | 739 | —F | —CH$_2$— | 3-(CF$_3$)-phenyl |
| 640 | —F | 4-(CF$_3$)-phenyl | 740 | —F | —CH$_2$— | 4-(CF$_3$)-phenyl |
| 641 | —CH$_3$ | 2-fluorophenyl | 741 | —CH$_3$ | —CH$_2$— | 2-fluorophenyl |
| 642 | —CH$_3$ | 3-fluorophenyl | 742 | —CH$_3$ | —CH$_2$— | 3-fluorophenyl |
| 643 | —CH$_3$ | 4-fluorophenyl | 743 | —CH$_3$ | —CH$_2$— | 4-fluorophenyl |
| 644 | —CH$_3$ | 2,6-difluorophenyl | 745 | —CH$_3$ | —CH$_2$— | 2,6-difluorophenyl |
| 645 | —CH$_3$ | 2-chlorophenyl | 747 | —CH$_3$ | —CH$_2$— | 2-chlorophenyl |
| 646 | —CH$_3$ | 3-chlorophenyl | 746 | —CH$_3$ | —CH$_2$— | 3-chlorophenyl |
| 647 | —CH$_3$ | 4-chlorophenyl | 747 | —CH$_3$ | —CH$_2$— | 4-chlorophenyl |
| 648 | —CH$_3$ | 3,4-dichlorophenyl | 748 | —CH$_3$ | —CH$_2$— | 3,4-dichlorophenyl |

TABLE IV-continued

| No. | R⁴ | R³ | No. | R⁴ | L | R³ |
|---|---|---|---|---|---|---|
| 649 | —CH₃ | 2,4-dichlorophenyl | 749 | —CH₃ | —CH₂— | 2,4-dichlorophenyl |
| 650 | —CH₃ | 2,6-dichlorophenyl | 750 | —CH₃ | —CH₂— | 2,6-dichlorophenyl |
| 651 | —CH₃ | 2-methylphenyl | 751 | —CH₃ | —CH₂— | 2-methylphenyl |
| 652 | —CH₃ | 3-methylphenyl | 752 | —CH₃ | —CH₂— | 3-methylphenyl |
| 653 | —CH₃ | 4-methylphenyl | 753 | —CH₃ | —CH₂— | 4-methylphenyl |
| 654 | —CH₃ | 2,4-dimethylphenyl | 754 | —CH₃ | —CH₂— | 2,4-dimethylphenyl |
| 655 | —CH₃ | 2,6-dimethylphenyl | 755 | —CH₃ | —CH₂— | 2,6-dimethylphenyl |
| 656 | —CH₃ | 2-methoxyphenyl | 756 | —CH₃ | —CH₂— | 2-methoxyphenyl |
| 657 | —CH₃ | 3-methoxyphenyl | 757 | —CH₃ | —CH₂— | 3-methoxyphenyl |
| 658 | —CH₃ | 4-methoxyphenyl | 758 | —CH₃ | —CH₂— | 4-methoxyphenyl |
| 659 | —CH₃ | 3-(CF₃)-phenyl | 759 | —CH₃ | —CH₂— | 3-(CF₃)-phenyl |
| 660 | —CH₃ | 4-(CF₃)-phenyl | 760 | —CH₃ | —CH₂— | 4-(CF₃)-phenyl |
| 661 | —OCH₃ | 2-fluorophenyl | 761 | —OCH₃ | —CH₂— | 2-fluorophenyl |
| 662 | —OCH₃ | 3-fluorophenyl | 762 | —OCH₃ | —CH₂— | 3-fluorophenyl |
| 663 | —OCH₃ | 4-fluorophenyl | 763 | —OCH₃ | —CH₂— | 4-fluorophenyl |
| 664 | —OCH₃ | 2,6-difluorophenyl | 764 | —OCH₃ | —CH₂— | 2,6-difluorophenyl |
| 665 | —OCH₃ | 2-chlorophenyl | 765 | —OCH₃ | —CH₂— | 2-chlorophenyl |
| 666 | —OCH₃ | 3-chlorophenyl | 766 | —OCH₃ | —CH₂— | 3-chlorophenyl |
| 667 | —OCH₃ | 4-chlorophenyl | 767 | —OCH₃ | —CH₂— | 4-chlorophenyl |
| 668 | —OCH₃ | 3,4-dichlorophenyl | 768 | —OCH₃ | —CH₂— | 3,4-dichlorophenyl |
| 669 | —OCH₃ | 2,4-dichlorophenyl | 769 | —OCH₃ | —CH₂— | 2,4-dichlorophenyl |
| 670 | —OCH₃ | 2,6-dichlorophenyl | 770 | —OCH₃ | —CH₂— | 2,6-dichlorophenyl |
| 671 | —OCH₃ | 2-methylphenyl | 771 | —OCH₃ | —CH₂— | 2-methylphenyl |
| 672 | —OCH₃ | 3-methylphenyl | 772 | —OCH₃ | —CH₂— | 3-methylphenyl |
| 673 | —OCH₃ | 4-methylphenyl | 773 | —OCH₃ | —CH₂— | 4-methylphenyl |
| 674 | —OCH₃ | 2,4-dimethylphenyl | 774 | —OCH₃ | —CH₂— | 2,4-dimethylphenyl |
| 675 | —OCH₃ | 2,6-dimethylphenyl | 775 | —OCH₃ | —CH₂— | 2,6-dimethylphenyl |
| 676 | —OCH₃ | 2-methoxyphenyl | 776 | —OCH₃ | —CH₂— | 2-methoxyphenyl |
| 677 | —OCH₃ | 3-methoxyphenyl | 777 | —OCH₃ | —CH₂— | 3-methoxyphenyl |
| 678 | —OCH₃ | 4-methoxyphenyl | 778 | —OCH₃ | —CH₂— | 4-methoxyphenyl |
| 679 | —OCH₃ | 3-(CF₃)-phenyl | 779 | —OCH₃ | —CH₂— | 3-(CF₃)-phenyl |
| 680 | —OCH₃ | 4-(CF₃)-phenyl | 780 | —OCH₃ | —CH₂— | 4-(CF₃)-phenyl |
| 681 | —SCH₃ | 2-fluorophenyl | 781 | —SCH₃ | —CH₂— | 2-fluorophenyl |
| 682 | —SCH₃ | 3-fluorophenyl | 782 | —SCH₃ | —CH₂— | 3-fluorophenyl |
| 683 | —SCH₃ | 4-fluorophenyl | 783 | —SCH₃ | —CH₂— | 4-fluorophenyl |
| 684 | —SCH₃ | 2,6-difluorophenyl | 784 | —SCH₃ | —CH₂— | 2,6-difluorophenyl |
| 685 | —SCH₃ | 2-chlorophenyl | 785 | —SCH₃ | —CH₂— | 2-chlorophenyl |
| 686 | —SCH₃ | 3-chlorophenyl | 786 | —SCH₃ | —CH₂— | 3-chlorophenyl |
| 687 | —SCH₃ | 4-chlorophenyl | 787 | —SCH₃ | —CH₂— | 4-chlorophenyl |
| 688 | —SCH₃ | 3,4-dichlorophenyl | 788 | —SCH₃ | —CH₂— | 3,4-dichlorophenyl |
| 689 | —SCH₃ | 2,4-dichlorophenyl | 789 | —SCH₃ | —CH₂— | 2,4-dichlorophenyl |
| 690 | —SCH₃ | 2,6-dichlorophenyl | 790 | —SCH₃ | —CH₂— | 2,6-dichlorophenyl |
| 691 | —SCH₃ | 2-methylphenyl | 791 | —SCH₃ | —CH₂— | 2-methylphenyl |
| 692 | —SCH₃ | 3-methylphenyl | 792 | —SCH₃ | —CH₂— | 3-methylphenyl |
| 693 | —OCH₃ | 4-methylphenyl | 793 | —SCH₃ | —CH₂— | 4-methylphenyl |
| 694 | —SCH₃ | 2,4-dimethylphenyl | 794 | —SCH₃ | —CH₂— | 2,4-dimethylphenyl |
| 695 | —SCH₃ | 2,6-dimethylphenyl | 795 | —SCH₃ | —CH₂— | 2,6-dimethylphenyl |
| 696 | —SCH₃ | 2-methoxyphenyl | 796 | —SCH₃ | —CH₂— | 2-methoxyphenyl |
| 697 | —SCH₃ | 3-methoxyphenyl | 797 | —SCH₃ | —CH₂— | 3-methoxyphenyl |
| 698 | —SCH₃ | 4-methoxyphenyl | 798 | —SCH₃ | —CH₂— | 4-methoxyphenyl |
| 699 | —SCH₃ | 3-(CF₃)-phenyl | 799 | —SCH₃ | —CH₂— | 3-(CF₃)-phenyl |
| 500 | —SCH₃ | 4-(CF₃)-phenyl | 800 | —SCH₃ | —CH₂— | 4-(CF₃)-phenyl |

The following are non-limiting examples of the fourth iteration of Category I of the present invention.

1-(4-Fluorophenyl)-1-(2-isopropylamino-pyrimidin-4-yl)-3-pyridin-2-ylmethyl-urea; $^1$H NMR (300 MHz, CDCl$_3$) δ 11.38 (br s, 1H), 8.62 (d, J=4.9 Hz, 1H), 7.94 (d, J=5.8 Hz, 1H), 7.72 (dt, J=1.8, 7.5 Hz, 1H), 7.39 (d, J=7.9 Hz, 1H), 7.29-7.16 (m, 5H), 5.42 (d, J=5.8 Hz, 1H), 5.22 (br s, 1H), 4.76 (d, J=4.8 Hz, 2H), 4.15 (br s, 1H), 1.25 (m, 6H); MS (ESI) m/z 381 (M+1).

1-(4-Methoxy-phenyl)-1-(2-isopropylamino-pyrimidin-4-yl)-3-(2-chlorobenzyl)-urea; $^1$H NMR (300 MHz, CDCl$_3$) δ 10.64 (br s, 1H), 7.88 (d, J=5.9 Hz, 1H), 7.57-7.53 (m, 1H), 7.45-7.40 (m, 1H), 7.31-7.23 (m, 2H), 7.16 (d, J=8.9 Hz, 2H), 7.01 (d, J=8.9 Hz, 2H), 5.46 (d, J=5.9 Hz, 1H), 4.93 (br d, J=6.2 Hz, 1H), 4.68 (d, J=5.5 Hz, 2H), 3.87 (s, 3H), 3.87-3.70 (m, 1H), 1.15 (d, J=6.0 Hz, 6H); MS (ESI) m/z 426 (M+1).

The compounds which comprise Category II of the present invention are N-[(2-substituted-pyrimidin-4-yl)-(substituted or unsubstituted-phenyl)]-N'-aryl-ureas having the formula:

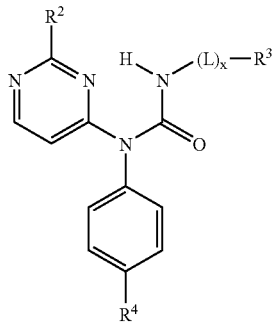

wherein the R$^3$ units comprise saturated or unsaturated C$_3$-C$_{10}$ carbocyclic, C$_1$-C$_{10}$ heteroaryl, or C$_1$-C$_{10}$ heterocyclic units. The first aspect of Category II relates to compounds having the formula:

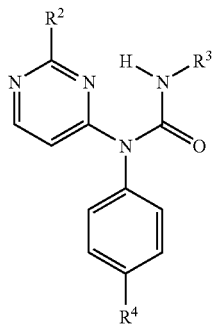

wherein the index x is equal to 0 and R is equal to R$^3$. Non-limiting examples of this aspect of Category II are defined herein below in Table V.

TABLE V

| No. | R$^4$ | R$^3$ | R$^2$ |
|---|---|---|---|
| 801 | —H | cyclopropyl | 2-hydroxy-1,2-dimethyl-propylamino |
| 802 | —H | cyclobutyl | 2-methoxy-1-methyl-ethylamino |
| 803 | —H | cyclopentyl | 1-phenyl-ethylamino |
| 804 | —H | cyclohexyl | 2-hydroxy-1,2-dimethyl-propylamino |

TABLE V-continued

| No. | R$^4$ | R$^3$ | R$^2$ |
|---|---|---|---|
| 805 | —H | pyrimidin-2-yl | 2-methoxy-1-methyl-ethylamino |
| 806 | —H | pyrimidin-4-yl | 1-phenyl-ethylamino |
| 807 | —H | pyrimidin-5-yl | 2-hydroxy-1,2-dimethyl-propylamino |
| 808 | —H | morpholin-4-yl | 2-methoxy-1-methyl-ethylamino |
| 809 | —H | pyridin-2-yl | 1-phenyl-ethylamino |
| 810 | —H | pyridine-3-yl | 2-hydroxy-1,2-dimethyl-propylamino |
| 811 | —H | pyridin-4-yl | 2-methoxy-1-methyl-ethylamino |
| 812 | —H | furan-2-yl | 1-phenyl-ethylamino |
| 813 | —H | furan-3-yl | 2-hydroxy-1,2-dimethyl-propylamino |
| 814 | —H | thien-2-yl | 2-methoxy-1-methyl-ethylamino |
| 815 | —H | thien-3-yl | 1-phenyl-ethylamino |
| 816 | —H | tetrahydro-pyran-4-yl | 2-hydroxy-1,2-dimethyl-propylamino |
| 817 | —F | cyclopropyl | 2-methoxy-1-methyl-ethylamino |
| 818 | —F | cyclobutyl | 1-phenyl-ethylamino |
| 819 | —F | cyclopentyl | 2-hydroxy-1,2-dimethyl-propylamino |
| 820 | —F | cyclohexyl | 2-methoxy-1-methyl-ethylamino |
| 821 | —F | pyrimidin-2-yl | 1-phenyl-ethylamino |
| 822 | —F | pyrimidin-4-yl | 2-hydroxy-1,2-dimethyl-propylamino |
| 823 | —F | pyrimidin-5-yl | 2-methoxy-1-methyl-ethylamino |
| 824 | —F | morpholin-4-yl | 1-phenyl-ethylamino |
| 825 | —F | pyridin-2-yl | 2-hydroxy-1,2-dimethyl-propylamino |
| 826 | —F | pyridine-3-yl | 2-methoxy-1-methyl-ethylamino |
| 827 | —F | pyridin-4-yl | 1-phenyl-ethylamino |
| 828 | —F | furan-2-yl | 2-hydroxy-1,2-dimethyl-propylamino |
| 829 | —F | furan-3-yl | 2-methoxy-1-methyl-ethylamino |
| 830 | —F | thien-2-yl | 1-phenyl-ethylamino |
| 831 | —F | thien-3-yl | 2-hydroxy-1,2-dimethyl-propylamino |
| 832 | —F | tetrahydro-pyran-4-yl | 2-methoxy-1-methyl-ethylamino |
| 833 | —CH$_3$ | cyclopropyl | 1-phenyl-ethylamino |
| 834 | —CH$_3$ | cyclobutyl | 2-hydroxy-1,2-dimethyl-propylamino |
| 835 | —CH$_3$ | cyclopentyl | 2-methoxy-1-methyl-ethylamino |
| 836 | —CH$_3$ | cyclohexyl | 1-phenyl-ethylamino |
| 837 | —CH$_3$ | pyrimidin-2-yl | 2-hydroxy-1,2-dimethyl-propylamino |
| 838 | —CH$_3$ | pyrimidin-4-yl | 2-methoxy-1-methyl-ethylamino |
| 839 | —CH$_3$ | pyrimidin-5-yl | 1-phenyl-ethylamino |
| 840 | —CH$_3$ | morpholin-4-yl | 2-hydroxy-1,2-dimethyl-propylamino |
| 841 | —CH$_3$ | pyridin-2-yl | 2-methoxy-1-methyl-ethylamino |
| 842 | —CH$_3$ | pyridine-3-yl | 1-phenyl-ethylamino |
| 843 | —CH$_3$ | pyridin-4-yl | 2-hydroxy-1,2-dimethyl-propylamino |
| 844 | —CH$_3$ | furan-2-yl | 2-methoxy-1-methyl-ethylamino |
| 845 | —CH$_3$ | furan-3-yl | 1-phenyl-ethylamino |
| 846 | —CH$_3$ | thien-2-yl | 2-hydroxy-1,2-dimethyl-propylamino |
| 847 | —CH$_3$ | thien-3-yl | 2-methoxy-1-methyl-ethylamino |
| 848 | —CH$_3$ | tetrahydro-pyran-4-yl | 1-phenyl-ethylamino |
| 849 | —OCH$_3$ | cyclopropyl | 2-hydroxy-1,2-dimethyl-propylamino |
| 850 | —OCH$_3$ | cyclobutyl | 2-methoxy-1-methyl-ethylamino |
| 851 | —OCH$_3$ | cyclopentyl | 1-phenyl-ethylamino |
| 852 | —OCH$_3$ | cyclohexyl | 2-hydroxy-1,2-dimethyl-propylamino |
| 853 | —OCH$_3$ | pyrimidin-2-yl | 2-methoxy-1-methyl-ethylamino |
| 854 | —OCH$_3$ | pyrimidin-4-yl | 1-phenyl-ethylamino |
| 855 | —OCH$_3$ | pyrimidin-5-yl | 2-hydroxy-1,2-dimethyl-propylamino |
| 856 | —OCH$_3$ | morpholin-4-yl | 2-methoxy-1-methyl-ethylamino |
| 857 | —OCH$_3$ | pyridin-2-yl | 1-phenyl-ethylamino |
| 858 | —OCH$_3$ | pyridine-3-yl | 2-hydroxy-1,2-dimethyl-propylamino |
| 859 | —OCH$_3$ | pyridin-4-yl | 2-methoxy-1-methyl-ethylamino |
| 860 | —OCH$_3$ | furan-2-yl | 1-phenyl-ethylamino |
| 861 | —OCH$_3$ | furan-3-yl | 2-hydroxy-1,2-dimethyl-propylamino |
| 862 | —OCH$_3$ | thien-2-yl | 2-methoxy-1-methyl-ethylamino |
| 863 | —OCH$_3$ | thien-3-yl | 1-phenyl-ethylamino |
| 864 | —OCH$_3$ | tetrahydro-pyran-4-yl | 2-hydroxy-1,2-dimethyl-propylamino |
| 865 | —SCH$_3$ | cyclopropyl | 2-methoxy-1-methyl-ethylamino |
| 866 | —SCH$_3$ | cyclobutyl | 1-phenyl-ethylamino |
| 867 | —SCH$_3$ | cyclopentyl | 2-hydroxy-1,2-dimethyl-propylamino |
| 868 | —SCH$_3$ | cyclohexyl | 2-methoxy-1-methyl-ethylamino |
| 869 | —SCH$_3$ | pyrimidin-2-yl | 1-phenyl-ethylamino |
| 870 | —SCH$_3$ | pyrimidin-4-yl | 2-hydroxy-1,2-dimethyl-propylamino |
| 871 | —SCH$_3$ | pyrimidin-5-yl | 2-methoxy-1-methyl-ethylamino |
| 872 | —SCH$_3$ | morpholin-4-yl | 1-phenyl-ethylamino |
| 873 | —SCH$_3$ | pyridin-2-yl | 2-hydroxy-1,2-dimethyl-propylamino |
| 874 | —SCH$_3$ | pyridine-3-yl | 2-methoxy-1-methyl-ethylamino |
| 875 | —SCH$_3$ | pyridin-4-yl | 1-phenyl-ethylamino |
| 876 | —SCH$_3$ | furan-2-yl | 2-hydroxy-1,2-dimethyl-propylamino |
| 877 | —SCH$_3$ | furan-3-yl | 2-methoxy-1-methyl-ethylamino |

TABLE V-continued

| No. | R⁴ | R³ | R² |
|---|---|---|---|
| 878 | —SCH₃ | thien-2-yl | 1-phenyl-ethylamino |
| 879 | —SCH₃ | thien-3-yl | 2-hydroxy-1,2-dimethyl-propylamino |
| 880 | —SCH₃ | tetrahydro-pyran-4-yl | 2-methoxy-1-methyl-ethylamino |

The following is a non-limiting example of compounds which comprise Category II of the present invention.

1-(4-Methoxyphenyl)-1-{2-[(1S)-2-methoxy-1-methyl-ethylamino]-pyrimidin-4yl}-3cyclohexyl-urea: $^1$H NMR (300 MHz, CDCl₃) δ 9.79 (br d, J=6.4 Hz, 1H), 7.87 (d, J=6.0 Hz, 1H), 7.14 (d, J=8.8 Hz, 2H), 7.00 (d, J=8.8 Hz, 2H), 5.54 (d, J=6.0 Hz, 1H), 5.33 (br s, 1H), 4.22-4.04 (m, 1H), 3.87 (s, 3H), 3.88-3.70 (m, 1H), 3.49 (br d, J=4.8 Hz, 1H), 3.43 (s, 3H), 2.20-1.98 (m, 2H), 1.88-1.54 (m, 4H), 1.53-1.14 (m, 4H), 1.34 (d, J=6.6 Hz, 3H); MS (ESI) m/z 414 (M+1).

The second aspect of Category II relates to compounds having the formula:

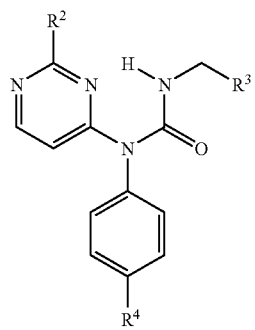

wherein the index x is equal to 1 and R is equal to R³. Non-limiting examples of this aspect of Category II are defined herein below in Table VI.

TABLE VI

| No. | R⁴ | R³ | R² |
|---|---|---|---|
| 881 | —H | cyclopropyl | 2-hydroxy-1,2-dimethyl-propylamino |
| 882 | —H | cyclobutyl | 2-methoxy-1-methyl-ethylamino |
| 883 | —H | cyclopentyl | 1-phenyl-ethylamino |
| 884 | —H | cyclohexyl | 2-hydroxy-1,2-dimethyl-propylamino |
| 885 | —H | pyrimidin-2-yl | 2-methoxy-1-methyl-ethylamino |
| 886 | —H | pyrimidin-4-yl | 1-phenyl-ethylamino |
| 887 | —H | pyrimidin-5-yl | 2-hydroxy-1,2-dimethyl-propylamino |
| 888 | —H | morpholin-4-yl | 2-methoxy-1-methyl-ethylamino |
| 889 | —H | pyridin-2-yl | 1-phenyl-ethylamino |
| 890 | —H | pyridine-3-yl | 2-hydroxy-1,2-dimethyl-propylamino |
| 891 | —H | pyridin-4-yl | 2-methoxy-1-methyl-ethylamino |
| 892 | —H | furan-2-yl | 1-phenyl-ethylamino |
| 893 | —H | furan-3-yl | 2-hydroxy-1,2-dimethyl-propylamino |
| 894 | —H | thien-2-yl | 2-methoxy-1-methyl-ethylamino |
| 895 | —H | thien-3-yl | 1-phenyl-ethylamino |
| 896 | —H | tetrahydro-pyran-4-yl | 2-hydroxy-1,2-dimethyl-propylamino |
| 897 | —F | cyclopropyl | 2-methoxy-1-methyl-ethylamino |
| 898 | —F | cyclobutyl | 1-phenyl-ethylamino |
| 899 | —F | cyclopentyl | 2-hydroxy-1,2-dimethyl-propylamino |
| 900 | —F | cyclohexyl | 2-methoxy-1-methyl-ethylamino |
| 901 | —F | pyrimidin-2-yl | 1-phenyl-ethylamino |
| 902 | —F | pyrimidin-4-yl | 2-hydroxy-1,2-dimethyl-propylamino |
| 903 | —F | pyrimidin-5-yl | 2-methoxy-1-methyl-ethylamino |
| 904 | —F | morpholin-4-yl | 1-phenyl-ethylamino |
| 905 | —F | pyridin-2-yl | 2-hydroxy-1,2-dimethyl-propylamino |
| 906 | —F | pyridine-3-yl | 2-methoxy-1-methyl-ethylamino |
| 907 | —F | pyridin-4-yl | 1-phenyl-ethylamino |
| 908 | —F | furan-2-yl | 2-hydroxy-1,2-dimethyl-propylamino |
| 909 | —F | furan-3-yl | 2-methoxy-1-methyl-ethylamino |
| 910 | —F | thien-2-yl | 1-phenyl-ethylamino |
| 911 | —F | thien-3-yl | 2-hydroxy-1,2-dimethyl-propylamino |
| 912 | —F | tetrahydro-pyran-4-yl | 2-methoxy-1-methyl-ethylamino |
| 913 | —CH₃ | cyclopropyl | 1-phenyl-ethylamino |
| 914 | —CH₃ | cyclobutyl | 2-hydroxy-1,2-dimethyl-propylamino |
| 915 | —CH₃ | cyclopentyl | 2-methoxy-1-methyl-ethylamino |
| 916 | —CH₃ | cyclohexyl | 1-phenyl-ethylamino |
| 917 | —CH₃ | pyrimidin-2-yl | 2-hydroxy-1,2-dimethyl-propylamino |
| 918 | —CH₃ | pyrimidin-4-yl | 2-methoxy-1-methyl-ethylamino |
| 919 | —CH₃ | pyrimidin-5-yl | 1-phenyl-ethylamino |
| 920 | —CH₃ | morpholin-4-yl | 2-hydroxy-1,2-dimethyl-propylamino |
| 921 | —CH₃ | pyridin-2-yl | 2-methoxy-1-methyl-ethylamino |
| 922 | —CH₃ | pyridine-3-yl | 1-phenyl-ethylamino |
| 923 | —CH₃ | pyridin-4-yl | 2-hydroxy-1,2-dimethyl-propylamino |
| 924 | —CH₃ | furan-2-yl | 2-methoxy-1-methyl-ethylamino |
| 925 | —CH₃ | furan-3-yl | 1-phenyl-ethylamino |
| 926 | —CH₃ | thien-2-yl | 2-hydroxy-1,2-dimethyl-propylamino |
| 927 | —CH₃ | thien-3-yl | 2-methoxy-1-methyl-ethylamino |
| 928 | —CH₃ | tetrahydro-pyran-4-yl | 1-phenyl-ethylamino |
| 929 | —OCH₃ | cyclopropyl | 2-hydroxy-1,2-dimethyl-propylamino |
| 930 | —OCH₃ | cyclobutyl | 2-methoxy-1-methyl-ethylamino |
| 931 | —OCH₃ | cyclopentyl | 1-phenyl-ethylamino |
| 932 | —OCH₃ | cyclohexyl | 2-hydroxy-1,2-dimethyl-propylamino |
| 933 | —OCH₃ | pyrimidin-2-yl | 2-methoxy-1-methyl-ethylamino |
| 934 | —OCH₃ | pyrimidin-4-yl | 1-phenyl-ethylamino |
| 935 | —OCH₃ | pyrimidin-5-yl | 2-hydroxy-1,2-dimethyl-propylamino |
| 936 | —OCH₃ | morpholin-4-yl | 2-methoxy-1-methyl-ethylamino |
| 937 | —OCH₃ | pyridin-2-yl | 1-phenyl-ethylamino |
| 938 | —OCH₃ | pyridine-3-yl | 2-hydroxy-1,2-dimethyl-propylamino |
| 939 | —OCH₃ | pyridin-4-yl | 2-methoxy-1-methyl-ethylamino |
| 940 | —OCH₃ | furan-2-yl | 1-phenyl-ethylamino |
| 941 | —OCH₃ | furan-3-yl | 2-hydroxy-1,2-dimethyl-propylamino |
| 942 | —OCH₃ | thien-2-yl | 2-methoxy-1-methyl-ethylamino |
| 943 | —OCH₃ | thien-3-yl | 1-phenyl-ethylamino |
| 944 | —OCH₃ | tetrahydro-pyran-4-yl | 2-hydroxy-1,2-dimethyl-propylamino |
| 945 | —SCH₃ | cyclopropyl | 2-methoxy-1-methyl-ethylamino |
| 946 | —SCH₃ | cyclobutyl | 1-phenyl-ethylamino |
| 947 | —SCH₃ | cyclopentyl | 2-hydroxy-1,2-dimethyl-propylamino |
| 948 | —SCH₃ | cyclohexyl | 2-methoxy-1-methyl-ethylamino |
| 949 | —SCH₃ | pyrimidin-2-yl | 1-phenyl-ethylamino |
| 950 | —SCH₃ | pyrimidin-4-yl | 2-hydroxy-1,2-dimethyl-propylamino |
| 951 | —SCH₃ | pyrimidin-5-yl | 2-methoxy-1-methyl-ethylamino |
| 952 | —SCH₃ | morpholin-4-yl | 1-phenyl-ethylamino |
| 953 | —SCH₃ | pyridin-2-yl | 2-hydroxy-1,2-dimethyl-propylamino |
| 954 | —SCH₃ | pyridine-3-yl | 2-methoxy-1-methyl-ethylamino |
| 955 | —SCH₃ | pyridin-4-yl | 1-phenyl-ethylamino |
| 956 | —SCH₃ | furan-2-yl | 2-hydroxy-1,2-dimethyl-propylamino |
| 957 | —SCH₃ | furan-3-yl | 2-methoxy-1-methyl-ethylamino |
| 958 | —SCH₃ | thien-2-yl | 1-phenyl-ethylamino |
| 959 | —SCH₃ | thien-3-yl | 2-hydroxy-1,2-dimethyl-propylamino |
| 960 | —SCH₃ | tetrahydro-pyran-4-yl | 2-methoxy-1-methyl-ethylamino |

The third aspect of Category II relates to compound wherein x is equal to 0 or 1 and the position of R⁴ on the aryl ring can be on carbons 2 or 3.

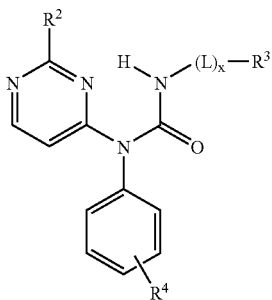

Non-limiting examples of this aspect include:

1-(2-Methoxyphenyl)-1-{2-[(1S)-2-methoxy-1-methyl-ethylamino]-pyrimidin-4-yl}-3-cyclopentyl-urea;

1-(3-Fluorophenyl)-1-{2-[(1S)-2-methoxy-1-methylethylamino]-pyrimidin-4-yl}-3-cyclohexyl-urea;

1-(3,5-Dichlorophenyl)-1-{2-[(1S)-2-methoxy-1-methyl-ethylamino]-pyrimidin-4-yl}-3-(pyridine-2-yl)-urea; and 1-(3-Methylphenyl)-1-{2-[(1S)-2-methoxy-1-methyl-ethylamino]-pyrimidin-4-yl}-3-cyclohexyl-urea.

The compounds which comprise the first aspect of Category III of the present invention are N-[(2-heterocyclyl-substituted-pyrimidin-4-yl)-(substituted or unsubstituted-phenyl)]-N'-aryl-ureas having the formula:

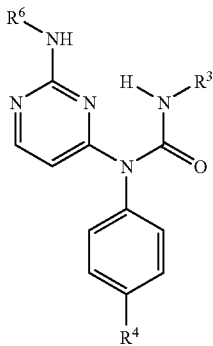

wherein the $R^3$ units are substitute aryl units, non-limiting examples of $R^6$ and $R^4$ are presented in Table VII herein below.

TABLE VII

| No. | $R^4$ | $R^3$ | $R^2$ |
|---|---|---|---|
| 961 | —F | phenyl | tetrahydropyran-4-yl |
| 962 | —F | 2-fluorophenyl | tetrahydropyran-4-yl |
| 963 | —F | 3-fluorophenyl | tetrahydropyran-4-yl |
| 964 | —F | 4-fluorophenyl | tetrahydropyran-4-yl |
| 965 | —F | 2,6-difluorophenyl | tetrahydropyran-4-yl |
| 966 | —F | 2-chlorophenyl | tetrahydropyran-4-yl |
| 967 | —F | 3-chlorophenyl | tetrahydropyran-4-yl |
| 968 | —F | 4-chlorophenyl | tetrahydropyran-4-yl |
| 969 | —F | 2,4-dichlorophenyl | tetrahydropyran-4-yl |
| 970 | —F | 2,6-dichlorophenyl | tetrahydropyran-4-yl |
| 971 | —F | 2-methylphenyl | tetrahydropyran-4-yl |
| 972 | —F | 3-methylphenyl | tetrahydropyran-4-yl |
| 973 | —F | 4-methylphenyl | tetrahydropyran-4-yl |
| 974 | —F | 2,4-dimethylphenyl | tetrahydropyran-4-yl |
| 975 | —F | 2,6-dimethylphenyl | tetrahydropyran-4-yl |
| 976 | —F | 2-methoxyphenyl | tetrahydropyran-4-yl |
| 977 | —F | 3-methoxyphenyl | tetrahydropyran-4-yl |
| 978 | —F | 4-methoxyphenyl | tetrahydropyran-4-yl |
| 979 | —F | 2,4-dimethoxyphenyl | tetrahydropyran-4-yl |
| 980 | —F | 2,6-dimethoxyphenyl | tetrahydropyran-4-yl |
| 981 | —OCH$_3$ | phenyl | tetrahydropyran-4-yl |
| 982 | —OCH$_3$ | 2-fluorophenyl | tetrahydropyran-4-yl |
| 983 | —OCH$_3$ | 3-fluorophenyl | tetrahydropyran-4-yl |
| 984 | —OCH$_3$ | 4-fluorophenyl | tetrahydropyran-4-yl |
| 985 | —OCH$_3$ | 2,6-difluorophenyl | tetrahydropyran-4-yl |
| 986 | —OCH$_3$ | 2-chlorophenyl | tetrahydropyran-4-yl |
| 987 | —OCH$_3$ | 3-chlorophenyl | tetrahydropyran-4-yl |
| 988 | —OCH$_3$ | 4-chlorophenyl | tetrahydropyran-4-yl |
| 989 | —OCH$_3$ | 2,4-dichlorophenyl | tetrahydropyran-4-yl |
| 990 | —OCH$_3$ | 2,6-dichlorophenyl | tetrahydropyran-4-yl |
| 991 | —OCH$_3$ | 2-methylphenyl | tetrahydropyran-4-yl |
| 992 | —OCH$_3$ | 3-methylphenyl | tetrahydropyran-4-yl |
| 993 | —OCH$_3$ | 4-methylphenyl | tetrahydropyran-4-yl |
| 994 | —OCH$_3$ | 2,4-dimethylphenyl | tetrahydropyran-4-yl |
| 995 | —OCH$_3$ | 2,6-dimethylphenyl | tetrahydropyran-4-yl |
| 996 | —OCH$_3$ | 2-methoxyphenyl | tetrahydropyran-4-yl |
| 997 | —OCH$_3$ | 3-methoxyphenyl | tetrahydropyran-4-yl |
| 998 | —OCH$_3$ | 4-methoxyphenyl | tetrahydropyran-4-yl |
| 999 | —OCH$_3$ | 2,4-dimethoxyphenyl | tetrahydropyran-4-yl |
| 1000 | —OCH$_3$ | 2,6-dimethoxyphenyl | tetrahydropyran-4-yl |

The following are non-limiting examples of Category III compounds wherein $R^2$ comprises a substituted or unsubstituted $C_1$-$C_{10}$ heterocyclic unit.

4-{4-[3-(2-Chlorophenyl)-1-(4-fluorophenyl)-ureido]-pyrimidin-2-ylamino}-piperidine-1-carboxylic acid ethyl ester: $^1$H NMR (300 MHz, CDCl$_3$) δ 13.01 (s, 1H), 8.37 (d, J=7.9 Hz, 1H), 8.02 (d, J=5.8 Hz, 1H), 7.44 (d, J=8.0 Hz, 1H), 7.31-7.20 (m, 6H), 7.06 (t, J=7.8 Hz, 1H), 5.54 (br d, J=5.7 Hz, 1H), 5.21 (d, J=7.9 Hz, 1H), 4.21-4.07 (m, 2H), 4.18 (q, J=7.1 Hz, 2H), 3.06 (br t, J=11.2 Hz, 2H), 2.13-2.07 (m, 2H), 1.48-140 (m, 2H), 1.30 (t, J=7.1 Hz, 3H); MS (ESI) m/z 428 (M+1).

1-(4-Fluorophenyl)-1-[2-(tetrahydro-pyran-4-ylamino)-pyrimidin-4-yl]-3-(2-chlorophenyl)-urea: $^1$H NMR (300 MHz, CDCl$_3$) δ 13.00 (s, 1H), 8.37 (d, J=7.5 Hz, 1H), 8.03 (d, J=5.8 Hz, 1H), 7.45 (d, J=8.0 Hz, 1H), 7.31-7.20 (m, 5H), 7.06 (dd, J=7.5, 7.9 Hz, 1H), 5.54 (br d, J=5.3 Hz, 1H), 5.25 (d, J=7.9 Hz, 1H), 4.14-4.08 (m, 1H), 4.02 (br d, J=11.7 Hz, 2H), 3.60-3.49 (m, 2H), 2.09 (br d, J=11.3 Hz, 2H), 1.66-1.38 (m, 2H); MS (ESI) m/z 441 (M+1).

1-(4-Fluorophenyl)-1-{2-[1-(propane-1-sulfanyl)-piperidin-4-ylamino]-pyrimidin-4-yl}-3-(2-chlorophenyl)-urea: $^1$H NMR (300 MHz, CDCl$_3$) δ 12.92 (s, 1H), 8.36 (d, J=7.7 Hz, 1H), 8.03 (d, J=5.8 Hz, 1H), 7.45 (d, J=8.0 Hz, 1H), 7.31-7.20 (m, 5H), 7.07 (t, J=7.7 Hz, 1H), 5.56 (br d, J=5.5 Hz, 1H), 5.23 (d, J=8.0 Hz, 1H), 4.11-4.01 (m, 1H), 3.78 (br d, J=12.4 Hz, 2H), 3.03 (br dd, J=10.6, 11.3, 2H), 2.93 (dd, J=7.7, 8.0 Hz, 2H), 2.21-2.17 (m, 2H), 1.95-1.82 (m, 2H), 1.71-1.59 (m, 2H) 1.10 (t, J=7.7 Hz, 3H); MS (ESI) m/z 547 (M+1).

1-(4-Fluorophenyl)-1-[2-(tetrahydro-pyran-4-ylamino)-pyrimidin-4-yl]-3-(2-chlorobenzyl)-urea: $^1$H NMR (300 MHz, CDCl$_3$) δ 10.14 (d, J=5.7 Hz, 1H), 7.74 (d, J=7.1 Hz, 2H), 7.49-7.46 (m, 1H), 7.34-7.22 (m, 6H), 7.09 (q, J=3.8 Hz, 2H), 6.70 (br d, 1H), 4.60 (d, J=5.9 Hz, 2H), 3.93-3.86 (m, 2H), 3.50-3.48 (m, 1H), 3.24-3.16 (m, 2H), 1.71-1.64 (m, 4H); MS (ESI) m/z 456 (M+1).

1-[2-(4-Fluorophenyl)-ethyl]-1-[2-(tetrahydro-pyran-4-ylamino)-pyrimidin-4-yl]-3-(2-chlorophenyl)-urea: $^1$H NMR (300 MHz, CDCl$_3$) δ 13.01 (s, 1H), 8.35 (br s, 1H), 8.25 (d, J=6.0 Hz, 1H), 7.44 (dd, J=1.5, 7.8 Hz, 1H), 7.36-7.27 (m, 3H), 7.10-7.01 (m, 3H), 6.32 (d, J=6.3 Hz, 1H), 5.23 (d, J=7.8

Hz, 1H), 4.15-4.07 (m, 2H), 4.03-3.98 (m, 2H), 3.59-3.52 (m, 2H), 3.02-2.97 (m, 2H), 2.09-2.06 (m, 2H), 1.64-1.51 (m, 4H); MS (ESI) m/z 470 (M+1).

The present invention includes compounds which are not encompassed by the Categories described herein above. The units described herein above for R, $R^1$, $R^2$, $R^3$, $R^4$, $R^5$, $R^6$, $R^7$, $R^8$, L, $L^1$ and $L^2$ can be suitably combined to provide compounds according to the present invention. The following are non-limiting examples of other analogs according to the present invention.

Compounds wherein $L^2$ is —NR—, $R^6$ and $R^7$ are hydrogen or $C_1$-$C_{10}$ substituted or unsubstituted alkyl, for example:

1-(4-Fluorophenyl)-1-(2-dimethylamino-pyrimidin-4-yl)-3-(2-chlorobenzyl)-urea: $^1$H NMR (300 MHz, $CDCl_3$) δ 10.60 (s, 1H), 7.96 (d, J=5.8 Hz, 1H), 7.59-7.52 (m, 1H), 7.46-7.36 (m, 1H), 7.31-7.15 (m, 6H), 5.37 (br d, J=5.9 Hz, 1H), 4.68 (d, J=5.3 Hz, 2H), 3.01 (s, 6H); MS (ESI) m/z 400 (M+1).

1-(4-Methoxyphenyl)-1-(2-methylamino-pyrimidin-4-yl)-3-(2-chlorobenzyl)-urea: $^1$H NMR (300 MHz, $CDCl_3$) δ 10.84 (s, 1H), 8.03 (d, J=5.8 Hz, 1H), 7.42-7.32 (m, 2H), 7.28-7.17 (m, 4H), 6.87 (d, J=8.8Hz, 2H), 6.18 (d, J=5.8 Hz, 1H), 4.59 (d, J=5.9 Hz, 2H), 3.80 (s, 3H), 3.52 (s, 3H); MS (ESI) m/z 398 (M+1).

Compounds wherein $L^2$ is —$NR^7$—, $R^6$ and $R^7$ are hydrogen or $C_6$-$C_{10}$ substituted or unsubstituted aryl, for example:

1-(4-Fluoro-phenyl)-1-[2-(2,6-difluorophenylamino)-pyrimidin-4-yl]-3-(2-chlorobenzyl)-urea: $^1$H NMR (300 MHz, DMSO-d6) δ 10.90 (t, J=5.7 Hz, 1H), 9.88 (s, 1H), 8.16 (d, J=5.9 Hz, 1H), 7.61-7.54 (m, 1H), 7.49-7.46 (m, 1H), 7.37-7.24 (m, 5H), 7.09 (q, J=3.8 Hz, 2H), 6.85 (t, J=8.8, 1H), 6.46 (d, J=5.9 Hz, 1H), 4.55 (d, J=5.7 Hz, 2H); $^{13}$C NMR (75 MHz, DMSO-d6) δ 161.4, 160.6, 159.8, 159.0, 158.1, 156.7, 154.9, 154.5, 137.1, 136.1, 132.8, 130.3, 130.0, 129.5, 129.4, 128.0, 121.6, 115.8, 115.5, 112.8, 112.5, 102.8, 42.4; MS (ESI) m/z 484 (M+1).

1-(4-Fluorophenyl)-1-(2-benzylamino-pyrimidin-4-yl)-3-(2-chlorophenyl)-urea: $^1$H NMR (300 MHz, $CDCl_3$) δ 8.32 (br s, 1H), 8.05 (d, J=6.0 Hz, 1H), 7.42-7.21 (m, 12H), 7.04 (dt, J=1.5, 7.8 Hz, 1H), 5.66 (m, 1H), 5.57 (d, J=6.0 Hz, 1H), 4.73 (d, J=6.0 Hz, 2H); MS (ESI) m/z 448 (M+1).

Compounds wherein $L^2$ is —$NR^7$—, $R^6$ and $R^7$ are hydrogen or $C_6$-$C_{10}$ substituted or unsubstituted aryl, for example:

1-(4-Fluorophenyl)-1-[2-(3-methyl-2,5-dioxo-2,5-dihydro-pyrrol-1-ylamino)-pyrimidin-4-yl]-3-(2-chlorophenyl)-urea: $^1$H NMR (300MHz, $d_6$-DMSO) δ 10.10 (s, 1H), 8.31 (d, J=5.7 Hz, 1H), 8.17 (d, J=7.8 Hz, 1H), 7.58 (d, J=7.5 Hz, 1H), 7.40-7.35 (m, 3H), 7.19-7.09 (m, 3H), 7.05 (d, J=1.5 Hz, 1H), 6.57 (d, J=6.0 Hz, 1H), 2.11 (s, 3H); MS (ESI) m/z 467 (M+1).

Compounds wherein $L^1$ is —$CH_2$—, and $R^5$ is a $C_1$-$C_{10}$ substituted or unsubstituted heterocycle unit for example:

1-(1-Benzyl-piperidin-4-yl)-1-{2-[(1S)1-phenyl-ethylamino]-pyrimidin-4-yl}-3-(2-chlorophenyl)-urea: $^1$H NMR (300 MHz, $CDCl_3$) δ 13.64 (s, 1H), 8.42 (d, J=8.1 Hz, 1H), 8.00 (d, J=5.7 Hz, 1H), 7.39-7.21 (m, 10H), 7.15 (t, J=6.9 Hz, 1H), 6.97 (t, J=7.5 Hz, 1H), 6.54 (q, J=6.9 Hz, 1H), 5.94 (br d, J=5.7 Hz, 1H), 4.64 (m, 1H), 3.54 (s, 2H), 3.59-3.50 (m, 1H), 2.81 (m, 2H), 2.37-1.94 (m, 2H), 1.97 (d, J=6.9 Hz, 3H), 1.63-1.25 (m, 4H); MS (ESI) m/z 541 (M+1).

Compounds wherein $L^2$ is absent, z=0, $R^6$ is substituted or unsubstituted $C_1$-$C_{10}$ heterocyclic or substituted or unsubstituted $C_1$-$C_{10}$ heteroaryl; for example:

1-(4-Fluorophenyl)-1-[2-(4-methyl-piperazin-1-yl)-pyrimidin-4-yl]-3-(2-chlorophenyl)-urea: $^1$H NMR (300 MHz, $CDCl_3$) δ 11.50 (s, 1H), 8.09 (d, J=8.1 Hz, 1H), 8.06 (d, J=5.7 Hz, 1H), 7.41 (d, J=8.0 Hz, 1H), 7.33-7.18 (m, 4H), 7.08 (t, J=7.2 Hz, 1H), 5.65 (d, J=5.7 Hz, 1H), 3.84 (t, J=5.1 Hz, 4H), 2.49 (t, J=5.1 Hz, 4H), 2.36 (s, 3H); MS (ESI) m/z 441 (M+1).

1-(4-Fluorophenyl)-1-(2-morpholin-4-yl-pyrimidin-4-yl)-3-(2-chlorophenyl)-urea: $^1$H NMR (300 MHz, $CDCl_3$) δ 11.37 (s, 1H), 8.11 (d, J=6.4 Hz, 1H), 8.09 (d, J=5.7 Hz, 1H), 7.42 (d, J=8.0 Hz, 1H), 7.34-7.20 (m, 5H), 7.10 (t, J=8.0 Hz, 1H), 5.74 (d, J=5.7 Hz, 1H), 3.79 (s, 8H); MS (ESI) m/z 428 (M+1).

The tri-substituted ureas of the present invention can be prepared by the procedure described in Examples 1 and 2 as outlined herein below in Schemes I and II.

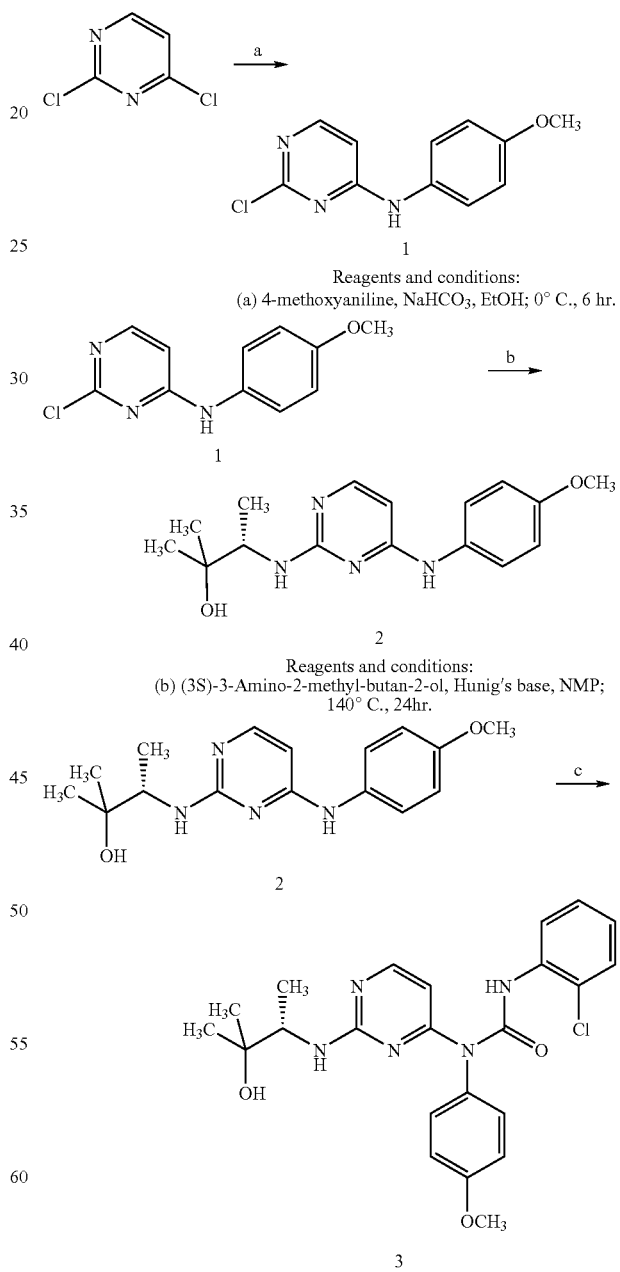

EXAMPLE 1

3-(2-Chlorophenyl)-1-{2-[(1S)-(2-hydroxy-1,2-dimethyl-propylamino]-pyrimidin-4-yl}-1-(4-methoxyphenyl)-urea (3)

Preparation of (2-chloropyrimidin-4-yl)-(4-methoxyphenyl)-amine (1): Sodium bicarbonate (1.26 g, 11.9 mmol) is added to a slurry of 2,4-dichloropyrimidine (1.01 g, 6.78 mmol) in ethanol (30 mL) at 0° C. 4-Methoxyaniline (840 mg, 6.82 mmol) is added and the slurry stirred at 0° C. for 6 hours. The reaction mixture is warmed to room temperature for 1 hour, then diluted with water (50 mL) and extracted three times with CHCl$_3$ (50 mL). The combined organic layers are washed with water (50 mL) and brine (50 mL), dried over sodium sulfate, filtered and concentrated in vacuo to give crude product which is purified over silica (10% Et$_2$O/CH$_2$Cl$_2$) to afford 1.20 g (75% yield) of the desired product as a white solid. $^1$H NMR (300 MHz, CDCl$_3$) δ 8.05 (d, J=5.8 Hz, 1H), 7.20 (d, J=9.0 Hz, 2H), 7.05 (br s, 1H), 6.94 (d, J=9.0 Hz, 2H), 6.41 (d, J=5.8 Hz, 1H), 3.83 (s, 3H); MS (ESI) m/z 236 (M+1).

Preparation of (3S)-3-[4-(4-methoxyphenylamino)pyrimidin-2-ylamino]-2-methyl-butan-2-ol (2): (3S)-3-Amino-2-methyl-butan-2-ol HCl (1.00 mg, 7.16 mmol; prepared using the method of Konno et. al., *Chem. Pharm. Bull*. 1997, 45, 185) is dissolved in N-methyl-pyrrolidinone (10 mL). Hunig's base (1.62 mL, 9.30 mmol) is added followed by (2-chloropyrimidin-4-yl)-(4-methoxyphenyl)-amine, 1, (789 mg, 3.35 mmol) and the solution warmed to 140° C. After 24 hours, the reaction mixture is cooled to room temperature and diluted with water (100 mL) and the mixture extracted three times with CH$_2$Cl$_2$ (100 mL). The combined organic layers are washed with saturated aqueous sodium bicarbonate solution (100 mL) and brine (100 mL), dried over magnesium sulfate, filtered and concentrated in vacuo. The crude product is purified over silica (100% CH$_2$Cl$_2$ to 5% to 10% MeOH/CH$_2$Cl$_2$) to afford 564 mg (46% yield) of the desired product as a tan solid. $^1$H NMR (300 MHz, CDCl$_3$) δ 7.78 (d, J=5.8 Hz, 1H), 7.20 (d, J=9.0 Hz, 2H), 6.87 (d, J=9.0 Hz, 2H), 5.87 (d, J=5.8 Hz, 1H), 4.00-3.90 (m, 1H), 3.80 (s, 3H), 2.83 (s, 3H), 1.25 (s, 3H), 1.18 (d, J=7.3 Hz, 3H), 1.17 (s, 3H); MS (ESI) m/z 303 (M+1).

Preparation of 3-(2-chlorophenyl)-1-{2-[(1S)-2-hydroxy-1,2-dimethyl-propylamino]-pyrimidin-4-yl}-1-(4-methoxy-phenyl)-urea (3): To a solution of (3S)-3-[4-(4-methoxy-phenylamino)pyrimidin-2-ylamino]-2-methyl-butan-2-ol, 2, (129 mg, 0.427 mmol) in dichloroethane (3 mL) is added 2-chlorophenyl isocyanate (57 μL, 0.469 mmol) dropwise via syringe. The reaction is stirred at room temperature for 2 hours. Additional 2-chloroisocyanate (57 μL, 0.469 mmol) is added and the reaction mixture stirred at room temperature for 16 hours after which the reaction mixture is diluted with CH$_2$Cl$_2$ (30 mL), and washed with saturated aqueous sodium bicarbonate solution (20 mL). The aqueous layer is extracted with CH$_2$Cl$_2$ (20 mL) and the combined organic layers washed with water and brine and dried over sodium sulfate, filtered and concentrated in vacuo to afford a crude residue which is purified over silica (5% to 20% Et$_2$O/CH$_2$Cl$_2$ to 10% MeOH/CH$_2$Cl$_2$) to afford the desired product as a white solid. $^1$H NMR (300 MHz, CDCl$_3$) δ 13.04 (br s, 1H), 8.41 (d, J=8.0 Hz, 1H), 7.92 (d, J=6.0 Hz, 1H), 7.37-7.16 (m, 4H), 7.17 (d, J=8.9 Hz, 2H), 7.02 (d, J=8.9 Hz, 2H), 5.56 (m, 2H), 4.05 (m, 1H), 3.85 (s, 3H), 1.30 (s, 3H), 1.25 (d, J=6.9 Hz, 3H), 1.23 (s, 3H); MS (ESI) m/z 456 (M+1).

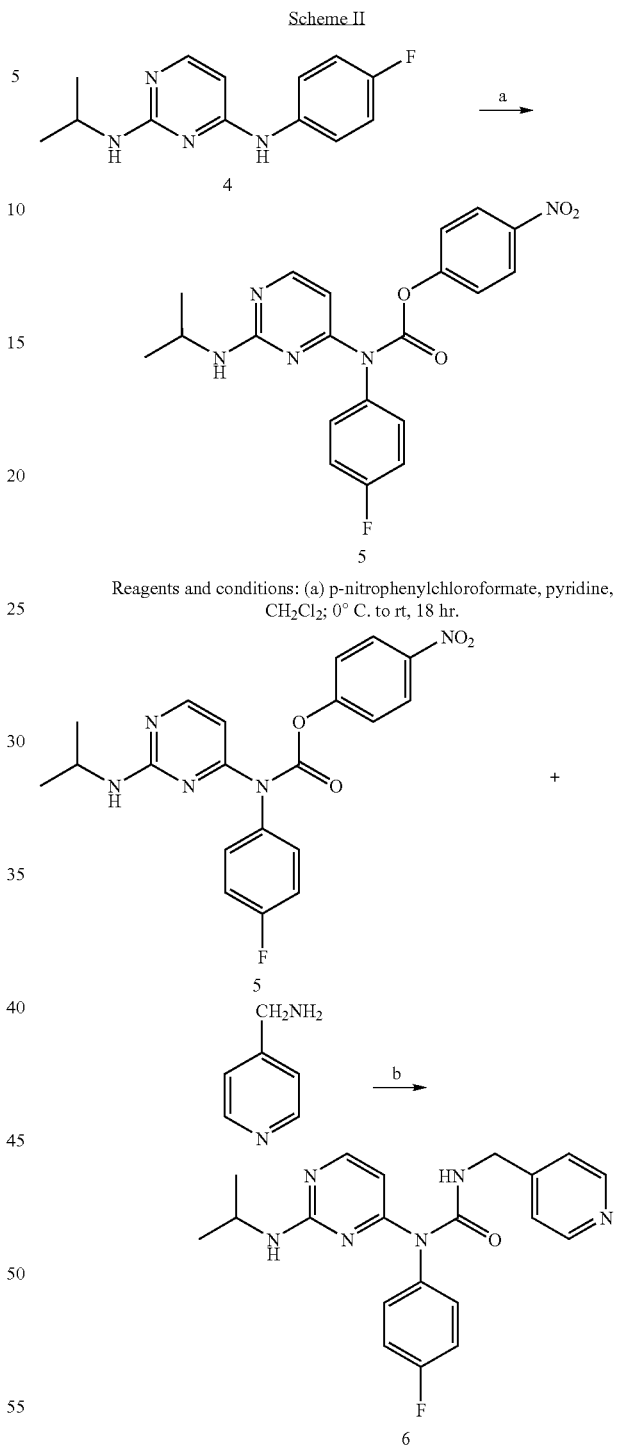

Scheme II

Reagents and conditions: (a) p-nitrophenylchloroformate, pyridine, CH$_2$Cl$_2$; 0° C. to rt, 18 hr.

Reagents and conditions: (b) CH$_2$Cl$_2$; rt, 18 hr.

EXAMPLE 2

1-(4-Fluorophenyl)-1-(2-isopropylamino-pyrimidin-4-yl)-3-pyridin-4-ylmethyl-urea (6)

Preparation of (4-fluorophenyl)-(2-isopropylamino-pyrimidin-4-yl)-carbamic acid 4-nitro-phenyl ester (5): A solution of N⁴-(4-fluorophenyl)-N²-isopropyl-pyrimidine-2,4-diamine, 4, (200 mg, 0.812 mmol) and p-nitrophenylchloroformate (251 mg, 1.24 mmol) in dichloroethane (8 mL) is stirred at 0° C. Pyridine (145 µL, 1.79 mmol) is added dropwise via syringe. The reaction mixture is allowed to stir at 0° C. and warm to ambient temperature overnight. The reaction solution is diluted with methylene chloride (50 mL) and washed with a 0.5 N aqueous solution of sodium hydroxide (2×50 mL) and water (50 mL), dried over sodium sulfate, filtered and concentrated to a yellow residue. This material was used without further purification: MS (ESI) m/z 412 (M+1).

Preparation of 1-(4-Fluorophenyl)-1-(2-isopropylamino-pyrimidin-4-yl)-3-pyridin-4-ylmethyl-urea (6): 4-(Aminomethyl)pyridine (100 µL, 0.974 mmol) is added dropwise to a solution of (4-fluorophenyl)-(2-isopropylamino-pyrimidin-4-yl)-carbamic acid 4-nitro-phenyl ester, 5, (334 mg, 0.812 mmol) in methylene chloride (8 mL) at room temperature. The orange solution is stirred at ambient temperature overnight. The reaction mixture is diluted with methylene chloride (50 mL) and washed with a 0.5 N aqueous solution of sodium hydroxide (2×50 mL) and water (50 mL), dried over sodium sulfate, filtered and concentrated to a yellow oil which is purified over silica (20% Et$_2$O/CH$_2$Cl$_2$ to 100% EtOAc) to afford the desired product as a white solid: $^1$H NMR (300 MHz, CDCl$_3$) δ 10.76 (br s, 1H), 8.61 (d, J=6.0 Hz, 2H), 7.93 (d, J=5.7 Hz, 1H), 7.34 (d, J=6.0 Hz, 2H), 7.29-7.16 (m, 4H), 5.43 (d, J=5.9 Hz, 1H), 5.02 (br s, 1H), 4.60 (d, J=5.5 Hz, 2H), 4.15 (br s, 1H), 1.15 (d, J=6.4 Hz, 6H); MS (ESI) m/z 381 (M+1).

Compounds listed and described herein above have been found in many instances to exhibit activities (IC$_{50}$ in the cell based assay described herein below or ones which are referenced herein) at a concentration below 1 micromolar (µM).

The compounds of the present invention are capable of effectively blocking the production of inflammatory cytokine production from cells, which thereby allows for the mitigation, alleviation, control, abatement, retardation, or prevention of one or more disease states or syndromes which are related to the extracellular release of one or more cytokines. Inflammatory disease states include those which are related to the following non-limiting examples:

i) Interleukin-1 (IL-1): implicated as the molecule responsible for a large number of disease states, inter alia, rheumatoid arthritis, osteoarthritis, as well as other disease states which relate to connective tissue degradation.

ii) Cycloxygenase-2 (COX-2): inhibitors of cytokine release are proposed as inhibitors of inducible COX-2 expression, which has been shown to be increased by cytokines. M. K. O'Banion et al., *Proc. Natl. Acad. Sci. U.S.A.*, 89, 4888 (1998).

iii) Tumor Necrosis Factor-α (TNF-α): This pro-inflammatory cytokine is suggested as an important mediator in many disease states or syndromes, inter alia, rheumatoid arthritis, osteoarthritis, inflammatory bowel disease (IBD), septic shock, cardiopulmonary dysfunction, acute respiratory disease, and cachexia.

iv) The compounds of the present invention have been found to be surprisingly effective in providing analgesia, or otherwise relieving pain in humans and higher mammals.

Each of the disease states or conditions which the formulator desires to treat may require differing levels or amounts of the compounds described herein to obtain a therapeutic level. The formulator can determine this amount by any of the known testing procedures known to the artisan.

The present invention further relates to forms of the present compounds, which under normal human or higher mammalian physiological conditions, release the compounds described herein. One iteration of this aspect includes the pharmaceutically acceptable salts of the analogs described herein. The formulator, for the purposes of compatibility with delivery mode, excipients, and the like, can select one salt form of the present analogs over another since the compounds themselves are the active species which mitigate the disease processes described herein.

Related to this aspect are the various precursor of "pro-drug" forms of the analogs of the present invention. It may be desirable to formulate the compounds of the present invention as a chemical species which itself is not active against the cytokine activity described herein, but instead are forms of the present analogs which when delivered to the body of a human or higher mammal will undergo a chemical reaction catalyzed by the normal function of the body, inter alia, enzymes present in the stomach, blood serum, said chemical reaction releasing the parent analog. The term "pro-drug" relates to these species which are converted in vivo to the active pharmaceutical.

FORMULATIONS

The present invention also relates to compositions or formulations which comprise the inflammatory cytokine release-inhibiting compounds according to the present invention. In general, the compositions of the present invention comprise:

a) an effective amount of one or more 1,1,3-tri-substituted ureas and salts thereof according to the present invention which are effective for inhibiting release of inflammatory cytokines; and b) one or more pharmaceutically acceptable excipients.

For the purposes of the present invention the term "excipient" and "carrier" are used interchangeably throughout the description of the present invention and said terms are defined herein as, "ingredients which are used in the practice of formulating a safe and effective pharmaceutical composition."

The formulator will understand that excipients are used primarily to serve in delivering a safe, stable, and functional pharmaceutical, serving not only as part of the overall vehicle for delivery but also as a means for achieving effective absorption by the recipient of the active ingredient. An excipient may fill a role as simple and direct as being an inert filler, or an excipient as used herein may be part of a pH stabilizing system or coating to insure delivery of the ingredients safely to the stomach. The formulator can also take advantage of the fact the compounds of the present invention have improved cellular potency, pharmacokinetic properties, as well as improved oral bioavailability.

Non-limiting examples of compositions according to the present invention include:

a) from about 0.001 mg to about 1000 mg of one or more 1,1,3-tri-substituted ureas according to the present invention; and b) one or more excipient.

Another embodiment according to the present invention relates to the following compositions:

a) from about 0.01 mg to about 100 mg of one or more 1,1,3-tri-substituted ureas according to the present invention; and b) one or more excipient.

A further embodiment according to the present invention relates to the following compositions:

a) from about 0.1 mg to about 10 mg of one or more 1,1,3-tri-substituted ureas according to the present invention; and b) one or more excipient.

The term "effective amount" as used herein means "an amount of one or more 1,1,3-tri-substituted ureas, effective at dosages and for periods of time necessary to achieve the desired result." An effective amount may vary according to factors known in the art, such as the disease state, age, sex, and weight of the human or animal being treated. Although particular dosage regimes may be described in examples herein, a person skilled in the art would appreciated that the dosage regime may be altered to provide optimum therapeutic response. For example, several divided doses may be administered daily or the dose may be proportionally reduced as indicated by the exigencies of the therapeutic situation. In addition, the compositions of the present invention can be administered as frequently as necessary to achieve a therapeutic amount.

Another aspect of the present invention relates to pharmaceutical compositions which provide analgesia, the compositions of the present invention comprise:

a) an amount of one or more 1,1,3-tri-substituted ureas and salts thereof according to the present invention in an amount effective for providing analgesia;

b) one or more excipients.

As second embodiment of this analgesia-providing aspect of the present invention includes compositions comprising:

a) an amount of one or more 1,1,3-tri-substituted ureas and salts thereof according to the present invention in an amount effective for providing analgesia;

b) an effective amount of one or more compounds having pain relief properties; and c) one or more excipients.

The following are non-limiting examples of compounds having pain relief properties or compounds which are effective in providing relief from pain and which can be suitably combined with the compounds of the present invention:

Acetaminophen, aspirin, difunisal, dipyrone, ibuprofen, naproxen, fenoprofen, fenbufen, ketoprofen, flurbiprofen, indomethacin, ketorolac, diclofenac, floctafenine, piroxicam, celecoxib, and rofecoxib.

The following are non-limiting of adjunct ingredients which may be combined with the compounds of the present invention: Caffeine, compatible amphetamines, compatible antihistamines, compatible antidepressants.

In addition, opioid narcotic analgesics may be combined to form pharmaceutical compositions, for example, oxycodone (Percadan, Percacet, Oxycontin, Tylox), pethidine/meperidine (Demerol), methadone (Physeptone, Dolophine), levorphanol (Dromoran, Levodromoran), hydromorphone (Dilaudid), and buprenorphine (Temgesic).

For the purposes of the present invention the term "excipient" and "carrier" are used interchangeably throughout the description of the present invention and said terms are defined herein as, "ingredients which are used in the practice of formulating a safe and effective pharmaceutical composition."

The formulator will understand that excipients are used primarily to serve in delivering a safe, stable, and functional pharmaceutical, serving not only as part of the overall vehicle for delivery but also as a means for achieving effective absorption by the recipient of the active ingredient. An excipient may fill a role as simple and direct as being an inert filler, or an excipient as used herein may be part of a pH stabilizing system or coating to insure delivery of the ingredients safely to the stomach. The formulator can also take advantage of the fact the compounds of the present invention have improved cellular potency, pharmacokinetic properties, as well as improved oral bioavailability.

METHOD OF USE

The present invention also relates to a method for controlling the level of one or more inflammation inducing cytokines, inter alia, interleukin-1 (IL-1), Tumor Necrosis Factor-$\alpha$ (TNF-$\alpha$), interleukin-6 (IL-6), and interleukin-8 (IL-8) and thereby controlling, mediating, or abating disease states affected by the levels of extracellular inflammatory cytokines. The present method comprises the step of administering to a human or higher mammal an effective amount of a composition comprising one or more of the inflammatory cytokine inhibitors according to the present invention.

The present invention also relates to the use of the 1,1,3-tri-substituted ureas according to the present invention in the manufacture of a medicament for the treatment of inflammatory cytokine related disorders. These disorders are described herein above under Inflammatory Disease States.

Because the inflammatory cytokine inhibitors of the present invention can be delivered in a manner wherein more than one site of control can be achieved, more than one disease state can be modulated at the same time. Non-limiting examples of diseases which are affected by control or inhibition of inflammatory cytokine inhibitors, thereby modulating excessive cytokine activity, include osteoarthritis, rheumatoid arthritis, diabetes, human Immunodeficiency virus (HIV) infection.

The present invention further relates to a method for providing analgesia and/or pain relief to humans or higher mammals which comprises the step of administering to said human or higher mammal an effective amount of a 1,1,3-tri-substituted urea described herein above. This method of treatment would also be effective for the treatment of fibromyalgia. This method of treatment may comprise administering to the human or higher mammal a direct amount of one or more analogs. Alternatively, the method comprises the step of administering to said human or higher mammal a pharmaceutical composition which comprises:

a) an effective amount of one or more 1,1,3-trisubstituted ureas and salts thereof according to the present invention which are effective for inhibiting release of inflammatory cytokines;

b) an effective amount of one or more compounds having pain relief properties; and c) one or more excipients.

The yet further aspect of the present invention relates to methods for reducing inflammatory bowel disease (IBD) in humans and higher mammals, said method comprising the step of administering to a human or high mammal an effective amount of a 1,1,3-tri-substituted urea according to the present invention.

Elevated levels of pro-inflammatory cytokines are implicated in many disease states and inhibition of pro-inflammatory cytokine production offers the opportunity to treat or prevent a wide range of diseases and conditions involving elevated levels of pro-inflammatory cytokines. Cytokines have been linked to acute and chronic inflammatory diseases, such as the inflammatory reaction induced by endotoxin or inflammatory bowel disease (IBD), Crohn's disease and ulcerative colitis, for example, see:

i) Rankin, E. C. C., et al. 1997, *British J Rheum*. 35:334;

ii) Stack, W. A., et al. 1997, *The Lancet* 349:521;

both of which are incorporated herein by reference.

An additional aspect of the present invention relates to methods for reducing psoriasis in humans and higher mammals, said method comprising the step of administering to a human or high mammal an effective amount of a 1,1,3-tri-substituted urea according to the present invention. It is well established that the control of cytokine activity is directly related to the formation of psoriasis and inhibition of this activity can be used as a therapy to control this condition. For example, see:

Lamotalos J., et al., "Novel Biological Immunotherapies for Psoriasis." *Expert Opinion Invstigative Drugs*; (2003); 12, 1111-1121.

The present invention, therefore, comprises a method for treating psoriasis in humans which comprises the step of administering to said human a pharmaceutical composition which comprises:

a) an effective amount of one or more 1,1,3-tri-substituted urea and salts thereof according to the present invention which are effective for inhibiting and/or controlling the release of inflammatory cytokines; and b) one or more excipients.

The above-described composition is also effective as a therapy against the following disease states, and therefore, provides a method for controlling said disease states:

Congestive Heart Failure[1,2,3,4,5]; hypertension[7]; chronic obstructive pulmonary disease and septic shock syndrome[8]; adult respiratory distress and asthma[8]; atherosclerosis[9]; muscle degeneration and periodontal disease[10]; cachexia, Reiter's syndrome, gout, acute synovitis, eating disorders, inter alia, anorexia and bulimia nervosa[11]; fever, malaise, myalgia and headaches[12]. The following are included herein by reference.

[1]. Han et al., *Trends in Cardiovascular Medicine*, 10:19, (2000);

[2]. Hunter et al., *New England Journal of Medicine*, 341:1276, (1999);

[3]. Behr et al. *Circulation*, 102:11-289, (2000);

[4]. Shimamoto et al, *Circulation*: 102:11-289, (2000);

[5]. Aukrust et al., *American Journal of Cardiology*,. 83:376 (1999);

[6]. Singh, et al., *Journal of Hypertension*, 9:867 (1996);

[7]. Dinarello, C. A., *Nutrition* 11:492 (1995);

[8]. Renzetti, et al. *Inflammation Res*. 46:S143;

[9]. Elhage, et al., *Circulation* 97:242 (1998);

[10]. Howells, *Oral Dis*. 1:266 (1995);

[11]. Holden, et al., *Medical Hypothesis* 47:423 (1996);

[12]. Beisel, *American Journal of Clinical Nutrition*, 62:813 (1995).

PROCEDURES

The compounds of the present invention can be evaluated for efficacy, for example, measurements of cytokine inhibition constants, $K_i$, and $IC_{50}$ values can be obtained by any method chosen by the formulator.

Non-limiting examples of suitable assays include:

i) UV-visible substrate enzyme assay as described by L. Al Reiter, *Int. J. Peptide Protein Res*., 43, 87-96 (1994).

ii) Fluorescent substrate enzyme assay as described by Thomberry et al., *Nature*, 356, 768-774 (1992).

iii) PBMC Cell assay as described in U.S. Pat. No. 6,204, 261 B1 Batchelor et al., issued Mar. 20, 2001.

Each of the above citations is included herein by reference.

In addition, Tumor Necrosis Factor, TNF-α, inhibition can be measured by utilizing lipopolysaccharide (LPS) stimulated human monocytic cells (THP-1) as described in:

i) K. M. Mohler et al., "Protection Against a Lethal Dose of Endotoxin by an Inhibitor of Tumour Necrosis Factor Processing", *Nature*, 370, pp 218-220 (1994).

ii) U.S. Pat. No. 6,297,381 B1 Cirillo et al., issued Oct. 2, 2001, incorporated by reference and reproduced herein below in relevant portion thereof.

The inhibition of cytokine production can be observed by measuring inhibition of TNF-α in lipopolysaccharide stimulated THP cells. All cells and reagents are diluted in RPMI 1640 with phenol red and L-glutamine, supplemented with additional L-glutamine (total: 4 mM), penicillin and streptomycin (50 units/mL each) and fetal bovine serum (FBS 3%) (GIBCO, all conc. Final). Assay is performed under sterile conditions, only test compound preparation is non-sterile. Initial stock solutions are made in DMSO followed by dilution into RPMI 1640 2-fold higher than the desired final assay concentration. Confluent THP.1 cells ($2\times10^7$ cells/mL, final conc.; American Type Culture Company, Rockville, Md.) are added to 96 well polypropylene round bottomed culture plates (Costar 3790; sterile) containing 125 μL test compound (2-fold concentrated) or DMSO vehicle (controls, blanks). DMSO concentration should not exceed 0.2% final. Cell mixture is allowed to preincubate for 15 minutes at 37° C., 5% $CO_2$ prior to stimulation with lipopolysaccharide (LPS, 1 μg/mL final; Sigma L-2630, from *E. coli* serotype 0111.B4; stored as 1 mg/mL stock in endotoxin screened diluted $H_2O$ vehicle at –80° C.). Blanks (unstimulated) receive $H_2O$ vehicle; final incubation volume is 250 μL. Incubation (4 hours) proceeds as described above. Assay is to be terminated by centrifuging plates 5 minutes at room temperature, 1600 rpm (4033 g); supernatants are then transferred to clean 96 well plates and stored at –80° C. until analyzed for human TNF-α by a commercially available ELISA kit (Biosource #KHC3015, Camarillo, Calif.). The calculated $IC_{50}$ value is the concentration of the test compound that caused a 50% decrease in the maximal TNF-α production.

Results for representative compounds according to the present invention are listed in Table VIII below.

TABLE VIII

| Compound Name | TNF-α $IC_{50}$ (nM) |
|---|---|
| 1-(4-Methoxyphenyl)-1-{2-[(1S)-2-hydroxy-1,2-dimethyl-propylamino]-pyrimidin-4-yl}-3-(2-chlorobenzyl)-urea | 9 |
| 1-(4-Methoxyphenyl)-1-{2-[(1S)-2-hydroxy-1,2-dimethyl-propylamino]-pyrimidin-4-yl}-3-(2-fluorobenzyl)-urea | 13 |
| 1-(4-Methoxyphenyl)-1-{2-[(1S)-2-hydroxy-1,2-dimethyl-propylamino]-pyrimidin-4-yl}-3-(2-methoxybenzyl)-urea | 15 |
| 1-(4-Fluorophenyl)-1-{2-[(1S)-2-hydroxy-1,2-dimethyl-propylamino]-pyrimidin-4-yl}-3-(2-chlorobenzyl)-urea | 14 |
| 1-(4-Fluorophenyl)-1-[2-(tetrahydropyran-4-ylamino)-pyrimidin-4-yl]-3-(2-chlorobenzyl)-urea | 16 |
| 1-(4-Ethoxyphenyl)-1-{2-[(1S)-2-methoxy-1-methyl-ethylamino]-pyrimidin-4-yl}-3-(2-chlorobenzyl)-urea | 56 |
| 1-(4-Methoxyphenyl)-1-{2-[(1S)-2-hydroxy-1,2-dimethyl-propylamino]-pyrimidin-4-yl}-3-(2-methylbenzyl)-urea | 37 |

Iodoacetate Induced Arthritis Test.

The following procedure is used for in vivo testing for arthritis efficacy. Sprague-Dawley male rats weighting 200-225 grams from Harlan (Oregon, Wis.) housed singly in wire cages in sanitary, ventilated animal rooms with controlled temperature, humidity and regular light cycles were used. Rodent chow (Ralston-Purina, Richmond, Ind.) and water were allowed ad libitum. Animals were acclimated for one week before use.

Arthritis was induced by a single intraarticular injection of iodoacetate into the knee joint of rats anesthetized using (3:1) $CO_2/O_2$. A 10 mg/ml concentration of monosodium iodoacetate (IA) (Aldrich Chemical, Milwaukee, Wis.) was prepared using injectable saline as the vehicle. After appropriate anesthesia each rat was positioned on its back and the left leg was flexed 90 degrees at the knee. The patellar ligament was palpated below the patella and the injection was made into this region. Each rat received 0.020 ml intra-articular injection of sodium IA, into the left knee using a glass gas tight syringe with a 27 gauge ¼ inch needle, on day 1 of the study. Care was taken not to advance the needle in too far into the cruciate ligaments.

Groups consisted of animals being dosed orally with 1-(4-Methoxyphenyl)-1-{2-[(1S)-2-hydroxy-1,2-dimethyl-propylamino]-pyrimidin-4-yl}-3-(2-chlorobenzyl)-urea @ 25 mg/kg BID (~every 12 hours for 5 days) and Vehicle dosed orally @ 2.5 ml/kg BID (~every 12 hours for 5 days). Following dosing, animals remained on study until humanely sacrificed on day 22 by way of CO2 overdose.

Animals were weighed weekly during this study for health monitoring. Animals were sacrificed on day 22 and the left joint was immediately disarticulated and fixed in 10% buffered formalin for 24 to 48 hours prior to capturing the image.

After fixation, an image of the tibial cartilage surface was captured using an Optimas (Optimas, Media Cybernetics LP, Silver Springs, Mass.) image analysis system. The image was used for grading the severity of damaged cartilage. Three independent observers assessed the damage in a blinded manner using a scale of 0-4 of increasing severity (0=normal; 4=maximum severity).

As described herein above, the compounds of the present invention have been found to be effective as analgesics. One convenient means for evaluating pain and for measuring the effective amount of compound(s) necessary to achieve analgesia and, therefore, provide a means for determining the amount of compound(s) which comprises a pharmaceutical composition of the present invention and the amount of compound(s) necessary for use in the methods described herein, is the Rat Thermal Hyperalgesia Model as described herein below.

The Rat Thermal Hyperalgesia Model, i.e., "Hargreaves Method" [Hargreaves, K., et al., Pain, (1988), 32:77-88], is used to determine the level at which the systemic administration of test compounds attenuate the hyperalgesia response subsequent to an intraplantar injection of carrageenan.

Analgesia Test Method:

Sprague-Dawley male rats weighing 100-150 g and housed two per shoebox cage in sanitary, ventilated animal rooms with controlled temperature, humidity and regular light cycles are used. Rodent chow and water were allowed ad libitum. Animals are acclimated for one week before use. All animal use is in accordance with the United States Department of Agriculture guidelines for humane care.

On the first day of study, each animal is acclimated to test equipment and the baseline paw withdrawal latency (PWL) to a radiant heat source is recorded. The following day, animals are orally dosed with vehicle or test compound. Thirty minutes later, each animal receives a 0.1 mL intra plantar injection of carrageenan (1.2% solution, w/v) into the left hind paw. Four hours post-carrageenan injection, animals are returned to the test equipment to determine PWL of the inflamed paw. The animals are then humanely euthanized with an overdose of carbon dioxide. Statistical analysis of data: Change from pre to post PWL for each animal is calculated. Statistical comparison between treatment groups on these two end points are made via an ANCOVA model with treatment terms, as well as pre-treatment measure as baseline covariate.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A compound, or an enantiomeric or a diastereomeric form, or salts thereof, said compound having the formula:

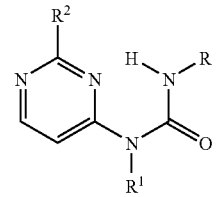

wherein R has the formula:

-(L)$_x$-R$^3$

R$^3$ is chosen from:
i) substituted or unsubstituted $C_6$-$C_{10}$ aryl;
ii) substituted or unsubstituted $C_1$-$C_{10}$ heteroaryl;
iii) substituted or unsubstituted $C_3$-$C_{10}$ carbocyclic; or
iv) substituted or unsubstituted $C_1$-$C_{10}$ heterocyclic;
the index x is 0 or 1;
R$^1$ has the formula:

-(L$^1$)$_y$-R$^5$

R$^5$ is a unit chosen from:
i) substituted or unsubstituted $C_3$-$C_{10}$ carbocyclic;
ii) substituted or unsubstituted $C_6$-$C_{10}$ aryl;
iii) substituted or unsubstituted $C_1$-$C_{10}$ heterocyclic; and
iv) substituted or unsubstituted $C_1$-$C_{10}$ heteroaryl;
the index y is 0 or 1;
R$^2$ has the formula:

-(L$^2$)$_z$-R$^6$

R$^6$ is a unit chosen from:
i) hydrogen;
ii) substituted or unsubstituted $C_1$-$C_{10}$ linear or branched hydrocarbyl;
iii) substituted or unsubstituted $C_3$-$C_{10}$ carbocyclic;
iv) substituted or unsubstituted $C_6$-$C_{10}$ aryl;
v) substituted or unsubstituted $C_1$-$C_{10}$ heterocyclic; and
vi) substituted or unsubstituted $C_1$-$C_{10}$ heteroaryl;
the index z is 0 or 1;
L, L$^1$ and L$^2$ are linking groups each of which are independently chosen from:
i) —C(R$^7$)$_2$—;
ii) —NR$^7$—; and
iii) —O—;
R$^7$ is hydrogen, $C_1$-$C_4$ alkyl, and mixtures thereof; or two R$^7$ units can be taken together to form a carbonyl unit.

2. A compound according to claim 1 wherein the index is equal to 0; R has the formula:

—R$^3$ wherein R$^3$ is a substituted or unsubstituted $C_6$ aryl unit; said substitution is chosen from: halogen, $C_1$-$C_4$ linear or branched alkyl, —OR$^8$, —CN, —N(R$^8$)$_2$, —CO$_2$R$^8$, —C(O)N(R$^8$)$_2$, —NR$^8$C(O)R$^8$, —NO$_2$, and —SR$^8$; each R$^8$ is independently hydrogen, substituted or unsubstituted $C_1$-$C_4$ linear, branched, or cyclic alkyl; or two R$^8$ units can be taken together to form a ring comprising from 3-7 atoms.

3. A compound according to claim 2 wherein R$^3$ is chosen from phenyl, 2-fluorophenyl, 3-fluorophenyl, 4-fluorophenyl, 2,3-difluorophenyl, 2,4-difluorophenyl, 2,5-difluorophenyl, 2,6-difluorophenyl, 3,5-difluorophenyl, 2,3,4-trifluorophenyl, 2,3,5-trifluorophenyl, 2,3,6-trifluorophenyl, 2,4,5-trifluorophenyl, 2,4,6-trifluorophenyl, 2-chlorophenyl, 3-chlorophenyl, 4-chlorophenyl, 2,3-dichlorophenyl, 2,4-dichlorophenyl, 2,5-dichlorophenyl, 2,6-dichlorophenyl, 3,5-dichlorophenyl, 2,3,4-trichlorophenyl, 2,3,5-trichlorophenyl, 2,3,6-trichlorophenyl, 2,4,5-trichlorophenyl, and 2,4,6-trichlorophenyl.

4. A compound according to claim 2 wherein $R^3$ is chosen from 2-methylphenyl, 3-methylphenyl, 4-methylphenyl, 2,3-dimethylphenyl, 2,4-dimethyl-phenyl, 2,5-dimethyl-phenyl, 2,6-dimethylphenyl, 3,5-dimethylphenyl, 2,3,4-trimethylphenyl, 2,3,5-trimethyl-phenyl, 2,3,6-trimethylphenyl, 2,4,5-trimethylphenyl, 2,4,6-trimethylphenyl, 2-ethylphenyl, 3-ethyl-phenyl, 4-ethylphenyl, 2,3-diethylphenyl, 2,4-diethylphenyl, 2,5-diethylphenyl, 2,6-diethylphenyl, 3,5-diethylphenyl, 2,3,4-triethylphenyl, 2,3,5-triethylphenyl, 2,3,6-triethylphenyl, 2,4,5-triethylphenyl, and 2,4,6-triethylphenyl.

5. A compound according to claim 2 wherein $R^3$ is chosen from 2-methoxyphenyl, 3-methoxyphenyl, 4-methoxyphenyl, 2,3-dimethoxyphenyl, 2,4-dimethoxyphenyl, 2,5-dimethoxyphenyl, 3,5-dimethoxyphenyl, 2,6-dimethoxyphenyl, 2,3,4-trimethoxyphenyl, 2,3,5-trimethoxyphenyl, 2,3,6-trimethoxyphenyl, 2,4,5-trimethoxyphenyl, 2,4,6-trimethoxyphenyl, 2-hydroxy-phenyl, 3-hydroxyphenyl, 4-hydroxyphenyl, 2,3-dihydroxyphenyl, 2,4-dihydroxyphenyl, 2,5-dihydroxyphenyl, 2,6-dihydroxyphenyl, 3,5-dihydroxyphenyl, 2,3,4-trihydroxyphenyl, 2,3,5-trihydroxy-phenyl, 2,3,6-trihydroxyphenyl, 2,4,5-trihydroxyphenyl, and 2,4,6-trihydroxyphenyl.

6. A compound according to claim 2 wherein $R^3$ is chosen from 3-dimethylaminophenyl, 4-dimethylaminophenyl, 3-diethylaminophenyl, 4-diethylaminophenyl, 3-methylsulfanylphenyl, 4-methylsulfanylphenyl, 3-ethylsulfanylphenyl, 4-ethylsulfanylphenyl, 3-propylsulfanylphenyl, and 4-propylsulfanylphenyl.

7. A compound according to claim 2 wherein $R^3$ is chosen from 2-cyanophenyl, 3-cyanophenyl, 4-cyanophenyl, 2,3-dicyanophenyl, 2,4-dicyanophenyl, 2,5-dicyanophenyl, 2,6-dicyanophenyl, 3,5-dicyanophenyl, 2,3,4-tricyanophenyl, 2,3,5-tricyanophenyl, 2,3,6-tricyanophenyl, 2,4,5-tricyanophenyl, and 2,4,6-tricyanophenyl.

8. A compound according to claim 2 wherein $R^3$ is chosen from 2-nitrophenyl, 3-nitrophenyl, 4-nitrophenyl, 2,3-dinitrophenyl, 2,4-dinitrophenyl, 2,5-dinitrophenyl, 2,6-dinitrophenyl, 3,5-dinitrophenyl, 2,3,4-trinitrophenyl, 2,3,5-trinitrophenyl, 2,3,6-trinitrophenyl, 2,4,5-trinitrophenyl, and 2,4,6-trinitrophenyl.

9. A compound according to claim 2 wherein $R^3$ is chosen from 2,6-dimethyl-4-fluorophenyl, 2,6-dimethyl-3-fluorophenyl, 2,6-dimethyl-4-chlorophenyl, 2,6-di-tert-butyl-4-hydroxyphenyl, 2,6-difluoro-4-chlorophenyl, 2,6-difluoro-3-chlorophenyl, 2-hydroxy-4-methylphenyl, 2-hydroxy-5-methylphenyl, 2,6-dihydroxy-4-tert-butylphenyl, and 2,6-difluoro-4-cyanophenyl.

10. A compound according to claim 2 wherein $R^3$ is chosen from
i) —$CO_2R^8$;
ii) —$N(R^8)_2$;
iii) —$CON(R^8)_2$;
iv) —$NR^8COR^8$;
v) halogen;
vi) methyl;
vii) ethyl;
viii) —OH;
ix) —$OCH_3$;
x) —$OC_2H_5$; and
xi) —CN.

11. A compound according to claim 10 wherein $R^3$ is chosen from 2-carboxyphenyl, 3-carboxyphenyl, 4-carboxyphenyl, 2,4-dicarboxyphenyl, 2-carboxy-3-hydroxyphenyl, 2-carboxy-4-hydroxyphenyl, 3-carboxy-4-hydroxyphenyl, 2-hydroxy-4-carboxyphenyl, 2-carboxy-3-methoxyphenyl, 2-carboxy-4-methoxyphenyl, 3-carboxy-4-methoxyphenyl, and 2-methoxy-4-carboxyphenyl.

12. A compound according to claim 10 wherein $R^3$ is chosen from 2-methylaminophenyl, 3-methylaminophenyl, 4-methylaminophenyl, 2,4-dimethylaminophenyl, 2-methylamino-3-hydroxyphenyl, 2-methylamino-4-hydroxyphenyl, 3-methylamino-4-hydroxyphenyl, 2-hydroxy-4-methylaminophenyl, 2-methylamino-3-methoxyphenyl, 2-methylamino-4-methoxyphenyl, 3-methylamino-4-methoxyphenyl, and 2-methoxy-4-methylaminophenyl.

13. A compound according to claim 10 wherein $R^3$ is chosen from 2-N,N-dimethylaminophenyl, 3-N,N-dimethylaminophenyl, 2-N,N-diethylaminophenyl, 4-N,N-dimethylaminophenyl, 2-N,N-methylethylaminophenyl, 4-N,N-diethylaminophenyl, 2-hydroxy-4-N,N-dimethylaminophenyl, 2-methoxy-4-N,N-dimethylaminophenyl, and 2-methyl-4-N,N-dimethylaminophenyl.

14. A compound according to claim 1 wherein the index is equal to 0; R has the formula:

—$R^3$ $R^3$ is a substituted or unsubstituted $C_1$-$C_{10}$ heteroaryl unit.

15. A compound according to claim 14 wherein $R^3$ is a $C_4$ or $C_5$ heteroaryl unit comprising one heteroatom.

16. A compound according to claim 15 wherein $R^3$ is chosen from 2-furanyl, 2-thienyl, 2-pyridinyl, 3-pyridinyl, and 4-pyridinyl.

17. A compound according to claim 14 wherein $R^3$ is a $C_3$ or $C_4$ heteroaryl unit comprising more than one heteroatom.

18. A compound according to claim 17 wherein $R^3$ is chosen from triazinyl, pyrimidin-2-yl, pyrimidin-4-yl, pyrimidin-5-yl, and morpholin-4-yl.

19. A compound according to claim 1 wherein the index is equal to 0; R has the formula:

—$R^3$ $R^3$ is a substituted or unsubstituted $C_3$-$C_7$ cycloalkyl unit.

20. A compound according to claim 19 wherein $R^3$ is chosen from cyclopropyl, methylcyclopropyl, cyclobutyl, cyclopentyl, 2-methylcyclopentyl, cyclohexyl, and cycloheptyl.

21. A compound according to claim 1 wherein the index is equal to 1; R has the formula:

—$CH_2$—$R^3$ wherein $R^3$ is a substituted or unsubstituted $C_6$ aryl unit; said substitution is chosen from: halogen, $C_1$-$C_4$ linear or branched alkyl, —$OR^8$, —CN, —$N(R^8)_2$, —$CO_2R^8$, —C(O)N($R^8$)$_2$, —$NR^8C(O)R^8$, —$NO_2$, and —$SR^8$; each $R^8$ is independently hydrogen, substituted or unsubstituted $C_1$-$C_4$ linear, branched, or cyclic alkyl; or two $R^8$ units can be taken together to form a ring comprising from 3-7 atoms.

22. A compound according to claim 21 wherein $R^3$ is chosen from phenyl, 2-fluorophenyl, 3-fluorophenyl, 4-fluorophenyl, 2,3-difluorophenyl, 2,4-difluorophenyl, 2,5-difluorophenyl, 2,6-difluorophenyl, 3,5-difluorophenyl, 2,3,4-trifluorophenyl, 2,3,5-trifluorophenyl, 2,3,6-trifluorophenyl, 2,4,5-trifluorophenyl, 2,4,6-trifluorophenyl, 2-chlorophenyl, 3-chlorophenyl, 4-chlorophenyl, 2,3-dichlorophenyl, 2,4- dichlorophenyl, 2,5-dichlorophenyl, 2,6-dichlorophenyl, 3,5-dichlorophenyl, 2,3,4-trichlorophenyl, 2,3,5-trichlorophenyl, 2,3,6-trichlorophenyl, 2,4,5-trichlorophenyl, and 2,4,6-trichlorophenyl.

23. A compound according to claim 21 wherein $R^3$ is chosen from 2-methylphenyl, 3-methylphenyl, 4-methylphenyl, 2,3-dimethylphenyl, 2,4-dimethyl-phenyl, 2,5-dimethylphenyl, 2,6-dimethylphenyl, 3,5-dimethylphenyl, 2,3,4-trimethylphenyl, 2,3,5-trimethyl-phenyl, 2,3,6-trimethylphenyl, 2,4,5-trimethylphenyl, 2,4,6-trimethylphenyl, 2-ethylphenyl, 3-ethyl-phenyl, 4-ethylphenyl, 2,3-diethylphenyl, 2,4-diethylphenyl, 2,5-diethylphenyl, 2,6-diethylphenyl, 3,5-diethylphenyl, 2,3,4-triethylphenyl, 2,3,5-triethylphenyl, 2,3,6-triethylphenyl, 2,4,5-triethylphenyl, and 2,4,6-triethylphenyl.

24. A compound according to claim 21 wherein $R^3$ is chosen from 2-methoxyphenyl, 3-methoxyphenyl, 4-methoxyphenyl, 2,3-dimethoxyphenyl, 2,4-dimethoxyphenyl, 2,5-dimethoxyphenyl, 3,5-dimethoxyphenyl, 2,6-dimethoxyphenyl, 2,3,4-trimethoxyphenyl, 2,3,5-trimethoxyphenyl, 2,3,6-trimethoxyphenyl, 2,4,5-trimethoxyphenyl, 2,4,6-tri-methoxyphenyl, 2-hydroxyphenyl, 3-hydroxyphenyl, 4-hydroxyphenyl, 2,3-dihydroxyphenyl, 2,4-dihydroxyphenyl, 2,5-dihydroxyphenyl, 2,6-dihydroxyphenyl, 3,5-dihydroxyphenyl, 2,3,4-trihydroxyphenyl, 2,3,5-trihydroxyphenyl, 2,3,6-trihydroxyphenyl, 2,4,5-trihydroxyphenyl, and 2,4,6-trihydroxyphenyl.

25. A compound according to claim 21 wherein $R^3$ is chosen from 3-dimethylaminophenyl, 4-dimethylaminophenyl, 3-diethylaminophenyl, 4-diethylaminophenyl, 3-methyl-sulfanylphenyl, 4-methylsulfanylphenyl, 3-ethylsulfanylphenyl, 4-ethylsulfanylphenyl, 3-propylsulfanylphenyl, and 4-propylsulfanylphenyl.

26. A compound according to claim 21 wherein $R^3$ is chosen from 2-cyanophenyl, 3-cyanophenyl, 4-cyanophenyl, 2,3-dicyanophenyl, 2,4-dicyanophenyl, 2,5-dicyanophenyl, 2,6-dicyanophenyl, 3,5-dicyanophenyl, 2,3,4-tricyanophenyl, 2,3,5-tricyanophenyl, 2,3,6-tricyanophenyl, 2,4,5-tricyanophenyl, and 2,4,6-tricyanophenyl.

27. A compound according to claim 21 wherein $R^3$ is chosen from 2-nitrophenyl, 3-nitrophenyl, 4-nitrophenyl, 2,3-dinitrophenyl, 2,4-dinitrophenyl, 2,5-dinitrophenyl, 2,6-dinitrophenyl, 3,5-dinitrophenyl, 2,3,4-trinitrophenyl, 2,3,5-trinitrophenyl, 2,3,6-trinitrophenyl, 2,4,5-trinitrophenyl, and 2,4,6-trinitrophenyl.

28. A compound according to claim 21 wherein $R^3$ is chosen from 2,6-dimethyl-4-fluorophenyl, 2,6-dimethyl-3-fluorophenyl, 2,6-dimethyl-4-chlorophenyl, 2,6-di-tert-butyl-4-hydroxyphenyl, 2,6-difluoro-4-chlorophenyl, 2,6-difluoro-3-chlorophenyl, 2-hydroxy-4-methylphenyl, 2-hydroxy-5-methylphenyl, 2,6-dihydroxy-4-tert-butylphenyl, and 2,6-difluoro-4-cyanophenyl.

29. A compound according to claim 21 wherein $R^3$ is chosen from 2-carboxyphenyl, 3-carboxyphenyl, 4-carboxyphenyl, 2,4-dicarboxyphenyl, 2-carboxy-3-hydroxyphenyl, 2-carboxy-4-hydroxyphenyl, 3-carboxy-4-hydroxyphenyl, 2-hydroxy-4-carboxyphenyl, 2-carboxy-3-methoxyphenyl, 2-carboxy-4-methoxyphenyl, 3-carboxy-4-methoxyphenyl, and 2-methoxy-4-carboxyphenyl.

30. A compound according to claim 21 wherein $R^3$ is chosen from 2-methylaminophenyl, 3-methylaminophenyl, 4-methylaminophenyl, 2,4-dimethylaminophenyl, 2-methylamino-3-hydroxyphenyl, 2-methylamino-4-hydroxyphenyl, 3-methylamino-4-hydroxyphenyl, 2-hydroxy-4-methylaminophenyl, 2-methylamino-3-methoxyphenyl, 2-methylamino-4-methoxyphenyl, 3-methylamino-4-methoxyphenyl, and 2-methoxy-4-methylaminophenyl.

31. A compound according to claim 21 wherein $R^3$ is chosen from 2-N,N-dimethylaminophenyl, 3-N,N-dimethylaminophenyl, 2-N,N-diethylaminophenyl, 4-N,N-dimethylaminophenyl, 2-N,N-methylethylaminophenyl, 4-N,N-diethylaminophenyl, 2-hydroxy-4-N,N-dimethylaminophenyl, 2-methoxy-4-N,N-dimethylaminophenyl, and 2-methyl-4-N,N-dimethylaminophenyl.

32. A compound according to claim 1 wherein the index x is equal to 1; R has the formula:

—CH$_2$—R$^3$ $R^3$ is a substituted or unsubstituted $C_1$-$C_{10}$ heteroaryl unit.

33. A compound according to claim 32 wherein $R^3$ is a $C_4$ or $C_5$ heteroaryl unit comprising one heteroatom.

34. A compound according to claim 33 wherein $R^3$ is chosen from 2-furanyl, 2-thienyl, 2-pyridinyl, 3-pyridinyl, and 4-pyridinyl.

35. A compound according to claim 32 wherein $R^3$ is a $C_3$ or $C_4$ heteroaryl unit comprising more than one heteroatom.

36. A compound according to claim 35 wherein $R^3$ is chosen from triazinyl, pyrimidin-2-yl, pyrimidin-4-yl, pyrimidin-5-yl, and morpholin-4-yl.

37. A compound according to claim 1 wherein the index x is equal to 1; R has the formula:

—CH$_2$—R$^3$ $R^3$ is a substituted or unsubstituted $C_3$-$C_7$ cycloalkyl unit.

38. A compound according to claim 37 wherein $R^3$ is chosen from cyclopropyl, methylcyclopropyl, cyclobutyl, cyclopentyl, 2-methylcyclopentyl, cyclohexyl, and cycloheptyl.

39. A compound according to claim 1 wherein $R^1$ has the formula:

—R$^5$ $R^5$ is a substituted or unsubstituted $C_6$ aryl unit.

40. A compound according to claim 39 wherein $R^5$ chosen from phenyl, 2-fluorophenyl, 3-fluorophenyl, 4-fluorophenyl, 4-hydroxyphenyl, 4-methoxyphenyl, 4-ethoxyphenyl, 4-methylphenyl, 4-chlorophenyl, 4-methylsulfanyl-phenyl, and 4-dimethylaminophenyl.

41. A compound according to claim 1 wherein $R^1$ has the formula:

—R$^5$ $R^5$ is a substituted or unsubstituted $C_3$, $C_4$ or $C_5$ heterocyclic unit.

42. A compound according to claim 41 wherein $R^5$ is chosen from tetrahydrofuran-2-yl, tetrahydrofuran-3-yl, pyrrolidin-2-yl, pyrrolidin-3-yl, imidazolidine-2-yl, imidazolidine-4-yl, imidazolidine-5-yl, piperazine-1-yl, piperazine-2-yl, piperidine-1-yl, piperidine-2-yl, piperidine-3-yl, piperidine-4-yl, morpholin-4-yl, and tetrahydropyran-4-yl.

43. A compound according to claim 1 wherein $R^2$ has the formula:

—NH—R$^6$ $R^6$ is a substituted or unsubstituted linear or branched $C_1$-$C_{10}$ hydrocarbyl.

44. A compound according to claim 43 wherein $R^6$ is a unit chosen from 1(S)-2-hydroxy-1,2-dimethylpropyl, 1(S)-2-methoxy-1-methylethyl, 1(S)-sec-butyl, or isopropyl.

45. A compound according to claim 1 wherein $R^2$ has the formula:

—NH—$R^6$ $R^6$ is benzyl, 1-(S)-1-methylbenzyl, or tetrahydropyranyl.

46. A compound according to claim 1 wherein the index z is equal to 1 and linking unit $L^2$ is —$NR^7$—.

47. A compound according to claim 46 wherein linking unit $L^2$ is —NH—.

48. A compound, or an enantiomeric or a diastereomeric form, or salts thereof, said compound having the formula:

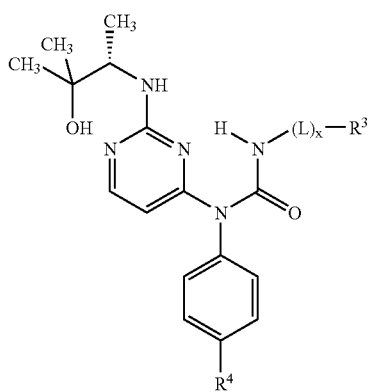

wherein $R^3$ is chosen from phenyl, 2-fluorophenyl, 3-fluorophenyl, 4-fluorophenyl, 2,6-difluorophenyl, 2-chlorophenyl, 3-chlorophenyl, 4-chlorophenyl, 2,4-dichlorophenyl, 3,4-dichlorophenyl, 2,6-dichlorophenyl, 2-methylphenyl, 3-methylphenyl, 4-methylphenyl, 2,4-dimethylphenyl, 2,6-dimethylphenyl, 2-methoxyphenyl, 3-methoxyphenyl, 4-methoxyphenyl, 3-trifluoromethylphenyl, or 4-trifluoromethylphenyl;

$R^4$ is —H, —F, —$CH_3$, —$OCH_3$, —$N(CH_3)_2$, or —$SCH_3$;

the index x is equal to 0 or 1; and when the index x is equal to 1, L is —$CH_2$—.

49. A compound, or an enantiomeric or a diasteriomeric form, or salts thereof, said compound having the formula:

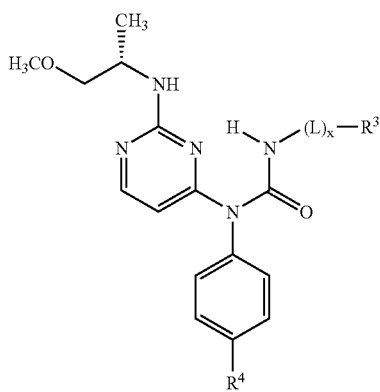

wherein $R^3$ is chosen from phenyl, 2-fluorophenyl, 3-fluorophenyl, 4-fluorophenyl, 2,6-difluorophenyl, 2-chlorophenyl, 3-chlorophenyl, 4-chlorophenyl, 2,4-dichlorophenyl, 3,4-dichlorophenyl, 2,6-dichlorophenyl, 2-methylphenyl, 3-methylphenyl, 4-methylphenyl, 2,4-dimethylphenyl, 2,6-dimethylphenyl, 2-methoxyphenyl, 3-methoxyphenyl, 4-methoxyphenyl, 3-trifluoromethylphenyl, or 4-trifluoromethylphenyl;

$R^4$ is —H, —F, —$CH_3$, —$OCH_3$, —$N(CH_3)_2$, or —$SCH_3$;

x is equal to 0 or 1; and when the index x is equal to 1, L is —$CH_2$—.

50. A compound, or an enantiomeric or a diasteriomeric form, or salts thereof, said compound having the formula:

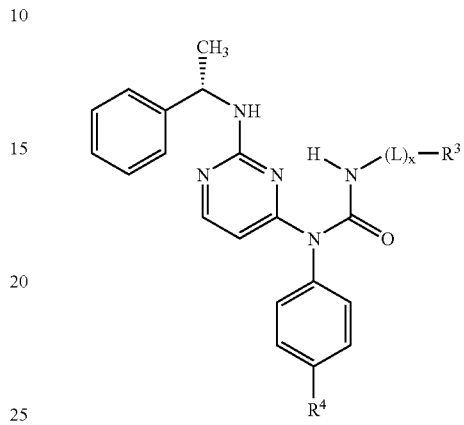

wherein $R^3$ is chosen from phenyl, 2-fluorophenyl, 3-fluorophenyl, 4-fluorophenyl, 2,6-difluorophenyl, 2-chlorophenyl, 3-chlorophenyl, 4-chlorophenyl, 2,4-dichlorophenyl, 3,4-dichlorophenyl, 2,6-dichlorophenyl, 2-methylphenyl, 3-methylphenyl, 4-methylphenyl, 2,4-dimethylphenyl, 2,6-dimethylphenyl, 2-methoxyphenyl, 3-methoxyphenyl, 4-methoxyphenyl, 3-trifluoromethylphenyl, or 4-trifluoromethylphenyl;

$R^4$ is —H, —F, —$CH_3$, —$OCH_3$, —$N(CH_3)_2$, or —$SCH_3$;

x is equal to 0 or 1; and when the index x is equal to 1, L is —$CH_2$—.

51. A compound chosen from:

1-(4-Fluorophenyl)-1-{2-[(1S)-2-hydroxy-1,2-dimethyl-propylamino]-pyrimidin-4-yl}-3-o-tolyl-urea;

1-(4-Fluorophenyl)-1-{2-[(1S)-2-hydroxy-1,2-dimethyl-propylamino]-pyrimidin-4-yl}-3-(2,6-dichlorophenyl)-urea;

1-(4-Methoxyphenyl)-1-{2-[(1S)-2-hydroxy-1,2-dimethylpropylamino]-pyrimidin-4-yl}-3-o-tolyl-urea;

1-(4-Methoxyphenyl)-1-{2-[(1S)-2-hydroxy-1,2-dimethyl-propylamino]-pyrimidin-4-yl}-3-(2-chlorophenyl)-urea;

1-Phenyl-1-{2-[(1S)-2-hydroxy-1,2-dimethylpropylamino]-pyrimidin-4-yl}-3-(2-chlorophenyl)-urea;

1-(4-Fluorophenyl)-1-{2-[(1S)-2-hydroxy-1,2-dimethylpropylamino]-pyrimidin-4-yl}-3-(2-chlorophenyl)-urea;

1-(4-Methoxyphenyl)-1-{2-[(1S)-2-hydroxy-1,2-dimethylpropylamino]-pyrimidin-4-yl}-3-(2-methoxybenzyl)-urea;

1-(4-Methoxy-phenyl)-1-{2-[(1S)-2-hydroxy-1,2-dimethyl-propylamino]-pyrimidin-4-yl}-3-(2-chlorobenzyl)-urea;

1-(4-Methoxyphenyl)-1-{2-[(1S)-2-hydroxy-1,2-dimethylpropylamino]-pyrimidin-4-yl}-3-(2-fluorobenzyl)-urea; and 1-(4-Fluorophenyl)-1-{2-[(1S)-2-hydroxy-1,2-dimethylpropyl-amino]-pyrimidin-4-yl}-3-(2-chlorobenzyl)-urea.

52. A compound chosen from:

1-Phenyl-1-{2-[(1S)-2-hydroxy-1,2-dimethyl-propylamino]-pyrimidin-4-yl}-3-o-tolyl-urea;
1-Phenyl-1-{2-[(1S)-2-hydroxy-1,2-dimethyl-propylamino]-pyrimidin-4-yl}-3-m-tolyl-urea;
1-Phenyl-1-{2-[(1S)-2-hydroxy-1,2-dimethyl-propylamino]-pyrimidin-4-yl}-3-p-tolyl-urea;
1-Phenyl-1-{2-[(1S)-2-hydroxy-1,2-dimethyl-propylamino]-pyrimidin-4-yl}-3-(2-fluorophenyl)-urea;
1-Phenyl-1-{2-[(1S)-2-hydroxy-1,2-dimethyl-propylamino]-pyrimidin-4-yl}-3-(3-fluorophenyl)-urea;
1-Phenyl-1-{2-[(1S)-2-hydroxy-1,2-dimethyl-propylamino]-pyrimidin-4-yl}-3-(4-phenyl)-urea;
1-Phenyl-1-{2-[(1S)-2-hydroxy-1,2-dimethyl-propylamino]-pyrimidin-4-yl}-3-(2,3-difluorophenyl)-urea;
1-Phenyl-1-{2-[(1S)-2-hydroxy-1,2-dimethyl-propylamino]-pyrimidin-4-yl}-3-(2,4-difluorophenyl)-urea;
1-Phenyl-1-{2-[(1S)-2-hydroxy-1,2-dimethyl-propylamino]-pyrimidin-4-yl}-3-(2,5-difluorophenyl)-urea;
1-Phenyl-1-{2-[(1S)-2-hydroxy-1,2-dimethyl-propylamino]-pyrimidin-4-yl}-3-(2,6-difluorophenyl)-urea;
1-Phenyl-1-{2-[(1S)-2-hydroxy-1,2-dimethyl-propylamino]-pyrimidin-4-yl}-3-(2,3,4-trifluorophenyl)-urea;
1-Phenyl-1-{2-[(1S)-2-hydroxy-1,2-dimethyl-propylamino]-pyrimidin-4-yl}-3-(2,3,5-trifluorophenyl)-urea;
1-Phenyl-1-{2-[(1S)-2-hydroxy-1,2-dimethyl-propylamino]-pyrimidin-4-yl}-3-(2,3,6-trifluorophenyl)-urea;
1-Phenyl-1-{2-[(1S)-2-hydroxy-1,2-dimethyl-propylamino]-pyrimidin-4-yl}-3-(2,4,5-trifluorophenyl)-urea;
1-Phenyl-1-{2-[(1S)-2-hydroxy-1,2-dimethyl-propylamino]-pyrimidin-4-yl}-3-(2,4,6-trifluorophenyl)-urea;
1-Phenyl-1-{2-[(1S)-2-hydroxy-1,2-dimethyl-propylamino]-pyrimidin-4-yl}-3-(3-chlorophenyl)-urea;
1-Phenyl-1-{2-[(1S)-2-hydroxy-1,2-dimethyl-propylamino]-pyrimidin-4-yl}-3-(4-chlorophenyl)-urea;
1-Phenyl-1-{2-[(1S)-2-hydroxy-1,2-dimethyl-propylamino]-pyrimidin-4-yl}-3-(2,3-dichlorophenyl)-urea;
1-Phenyl-1-{2-[(1S)-2-hydroxy-1,2-dimethyl-propylamino]-pyrimidin-4-yl}-3-(2,4-dichlorophenyl)-urea;
1-Phenyl-1-{2-[(1S)-2-hydroxy-1,2-dimethyl-propylamino]-pyrimidin-4-yl}-3-(2,5-dichlorophenyl)-urea;
1-Phenyl-1-{2-[(1S)-2-hydroxy-1,2-dimethyl-propylamino]-pyrimidin-4-yl}-3-(2,6-dichlorophenyl)-urea;
1-Phenyl-1-{2-[(1S)-2-hydroxy-1,2-dimethyl-propylamino]-pyrimidin-4-yl}-3-(2,3,4-trichlorophenyl)-urea;
1-Phenyl-1-{2-[(1S)-2-hydroxy-1,2-dimethyl-propylamino]-pyrimidin-4-yl}-3-(2,3,5-trichlorophenyl)-urea;
1-Phenyl-1-{2-[(1S)-2-hydroxy-1,2-dimethyl-propylamino]-pyrimidin-4-yl}-3-(2,3,6-trichlorophenyl)-urea;
1-Phenyl-1-{2-[(1S)-2-hydroxy-1,2-dimethyl-propylamino]-pyrimidin-4-yl}-3-(2,4,5-trichlorophenyl)-urea;
1-Phenyl-1-{2-[(1S)-2-hydroxy-1,2-dimethyl-propylamino]-pyrimidin-4-yl}-3-(2,4,6-trichlorophenyl)-urea;
1-(4-Fluorophenyl)-1-{2-[(1S)-2-hydroxy-1,2-dimethyl-propylamino]-pyrimidin-4-yl}-3-o-tolyl-urea;
1-(4-Fluorophenyl)-1-{2-[(1S)-2-hydroxy-1,2-dimethyl-propylamino]-pyrimidin-4-yl}-3-m-tolyl-urea;
1-(4-Fluorophenyl)-1-{2-[(1S)-2-hydroxy-1,2-dimethyl-propylamino]-pyrimidin-4-yl}-3-p-tolyl-urea;
1-(4-Fluorophenyl)-1-{2-[(1S)-2-hydroxy-1,2-dimethyl-propylamino]-pyrimidin-4-yl}-3-(2-fluorophenyl)-urea;
1-(4-Fluorophenyl)-1-{2-[(1S)-2-hydroxy-1,2-dimethyl-propylamino]-pyrimidin-4-yl}-3-(3-fluorophenyl)-urea;
1-(4-Fluorophenyl)-1-{2-[(1S)-2-hydroxy-1,2-dimethyl-propylamino]-pyrimidin-4-yl}-3-(4-fluorophenyl)-urea;
1-(4-Fluorophenyl)-1-{2-[(1S)-2-hydroxy-1,2-dimethyl-propylamino]-pyrimidin-4-yl}-3-(2,3-difluorophenyl)-urea;
1-(4-Fluorophenyl)-1-{2-[(1S)-2-hydroxy-1,2-dimethyl-propylamino]-pyrimidin-4-yl}-3-(2,4-difluorophenyl)-urea;
1-(4-Fluorophenyl)-1-{2-[(1S)-2-hydroxy-1,2-dimethyl-propylamino]-pyrimidin-4-yl}-3-(2,5-difluorophenyl)-urea;
1-(4-Fluorophenyl)-1-{2-[(1S)-2-hydroxy-1,2-dimethyl-propylamino]-pyrimidin-4-yl}-3-(2,6-difluorophenyl)-urea;
1-(4-Fluorophenyl)-1-{2-[(1S)-2-hydroxy-1,2-dimethyl-propylamino]-pyrimidin-4-yl}-3-(2,3,4-trifluorophenyl)-urea;
1-(4-Fluorophenyl)-1-{2-[(1S)-2-hydroxy-1,2-dimethyl-propylamino]-pyrimidin-4-yl}-3-(2,3,5-trifluorophenyl)-urea;
1-(4-Fluorophenyl)-1-{2-[(1S)-2-hydroxy-1,2-dimethyl-propylamino]-pyrimidin-4-yl}-3-(2,3,6-trifluorophenyl)-urea;
1-(4-Fluorophenyl)-1-{2-[(1S)-2-hydroxy-1,2-dimethyl-propylamino]-pyrimidin-4-yl}-3-(2,4,5-trifluorophenyl)-urea;
1-(4-Fluorophenyl)-1-{2-[(1S)-2-hydroxy-1,2-dimethyl-propylamino]-pyrimidin-4-yl}-3-(2,4,6-trifluorophenyl)-urea;
1-(4-Fluorophenyl)-1-{2-[(1S)-2-hydroxy-1,2-dimethyl-propylamino]-pyrimidin-4-yl}-3-(3-chlorophenyl)-urea;
1-(4-Fluorophenyl)-1-{2-[(1S)-2-hydroxy-1,2-dimethyl-propylamino]-pyrimidin-4-yl}-3-(4-chlorophenyl)-urea;
1-(4-Fluorophenyl)-1-{2-[(1S)-2-hydroxy-1,2-dimethyl-propylamino]-pyrimidin-4-yl}-3-(2,3-dichlorophenyl)-urea;
1-(4-Fluorophenyl)-1-{2-[(1S)-2-hydroxy-1,2-dimethyl-propylamino]-pyrimidin-4-yl}-3-(2,4-dichlorophenyl)-urea;
1-(4-Fluorophenyl)-1-{2-[(1S)-2-hydroxy-1,2-dimethyl-propylamino]-pyrimidin-4-yl}-3-(2,5-dichlorophenyl)-urea;
1-(4-Fluorophenyl)-1-{2-[(1S)-2-hydroxy-1,2-dimethyl-propylamino]-pyrimidin-4-yl}-3-(2,3,4-trichlorophenyl)-urea;
1-(4-Fluorophenyl)-1-{2-[(1S)-2-hydroxy-1,2-dimethyl-propylamino]-pyrimidin-4-yl}-3-(2,3,5-trichlorophenyl)-urea;
1-(4-Fluorophenyl)-1-{2-[(1S)-2-hydroxy-1,2-dimethyl-propylamino]-pyrimidin-4-yl}-3-(2,3,6-trichlorophenyl)-urea;
1-(4-Fluorophenyl)-1-{2-[(1S)-2-hydroxy-1,2-dimethyl-propylamino]-pyrimidin-4-yl}-3-(2,4,5-trichlorophenyl)-urea;

1-(4-Fluorophenyl)-1-{2-[(1S)-2-hydroxy-1,2-dimethyl-propylamino]-pyrimidin-4-yl}-3-(2,4,6-trichlorophenyl)-urea;
1-(4-Methoxyphenyl)-1-{2-[(1S)-2-hydroxy-1,2-dimethyl-propylamino]-pyrimidin-4-yl}-3-m-tolyl-urea;
1-(4-Methoxyphenyl)-1-{2-[(1S)-2-hydroxy-1,2-dimethyl-propylamino]-pyrimidin-4-yl}-3-p-tolyl-urea;
1-(4-Methoxyphenyl)-1-{2-[(1S)-2-hydroxy-1,2-dimethyl-propylamino]-pyrimidin-4-yl}-3-(2-fluorophenyl)-urea;
1-(4-Methoxyphenyl)-1-{2-[(1S)-2-hydroxy-1,2-dimethyl-propylamino]-pyrimidin-4-yl}-3-(3-fluorophenyl)-urea;
1-(4-Methoxyphenyl)-1-{2-[(1S)-2-hydroxy-1,2-dimethyl-propylamino]-pyrimidin-4-yl}-3-(4-fluorophenyl)-urea;
1-(4-Methoxyphenyl)-1-{2-[(1S)-2-hydroxy-1,2-dimethyl-propylamino]-pyrimidin-4-yl}-3-(2,3-difluorophenyl)-urea;
1-(4-Methoxyphenyl)-1-{2-[(1S)-2-hydroxy-1,2-dimethyl-propylamino]-pyrimidin-4-yl}-3-(2,4-difluorophenyl)-urea;
1-(4-Methoxyphenyl)-1-{2-[(1S)-2-hydroxy-1,2-dimethyl-propylamino]-pyrimidin-4-yl}-3-(2,5-difluorophenyl)-urea;
1-(4-Methoxyphenyl)-1-{2-[(1S)-2-hydroxy-1,2-dimethyl-propylamino]-pyrimidin-4-yl}-3-(2,6-difluorophenyl)-urea;
1-(4-Methoxyphenyl)-1-{2-[(1S)-2-hydroxy-1,2-dimethyl-propylamino]-pyrimidin-4-yl}-3-(2,3,4-trifluorophenyl)-urea;
1-(4-Methoxyphenyl)-1-{2-[(1S)-2-hydroxy-1,2-dimethyl-propylamino]-pyrimidin-4-yl}-3-(2,3,5-trifluorophenyl)-urea;
1-(4-Methoxyphenyl)-1-{2-[(1S)-2-hydroxy-1,2-dimethyl-propylamino]-pyrimidin-4-yl}-3-(2,3,6-trifluorophenyl)-urea;
1-(4-Methoxyphenyl)-1-{2-[(1S)-2-hydroxy-1,2-dimethyl-propylamino]-pyrimidin-4-yl}-3-(2,4,5-trifluorophenyl)-urea;
1-(4-Methoxyphenyl)-1-{2-[(1S)-2-hydroxy-1,2-dimethyl-propylamino]-pyrimidin-4-yl}-3-(2,4,6-trifluorophenyl)-urea;
1-(4-Methoxyphenyl)-1-{2-[(1S)-2-hydroxy-1,2-dimethyl-propylamino]-pyrimidin-4-yl}-3-(3-chlorophenyl)-urea;
1-(4-Methoxyphenyl)-1-{2-[(1S)-2-hydroxy-1,2-dimethyl-propylamino]-pyrimidin-4-yl}-3-(4-chlorophenyl)-urea;
1-(4-Methoxyphenyl)-1-{2-[(1S)-2-hydroxy-1,2-dimethyl-propylamino]-pyrimidin-4-yl}-3-(2,3-dichlorophenyl)-urea;
1-(4-Methoxyphenyl)-1-{2-[(1S)-2-hydroxy-1,2-dimethyl-propylamino]-pyrimidin-4-yl}-3-(2,4-dichlorophenyl)-urea;
1-(4-Methoxyphenyl)-1-{2-[(1S)-2-hydroxy-1,2-dimethyl-propylamino]-pyrimidin-4-yl}-3-(2,5-dichlorophenyl)-urea;
1-(4-Methoxyphenyl)-1-{2-[(1S)-2-hydroxy-1,2-dimethyl-propylamino]-pyrimidin-4-yl}-3-(2,6-dichlorophenyl)-urea;
1-(4-Methoxyphenyl)-1-{2-[(1S)-2-hydroxy-1,2-dimethyl-propylamino]-pyrimidin-4-yl}-3-(2,3,4-trichlorophenyl)-urea;
1-(4-Methoxyphenyl)-1-{2-[(1S)-2-hydroxy-1,2-dimethyl-propylamino]-pyrimidin-4-yl}-3-(2,3,5-trichlorophenyl)-urea;
1-(4-Methoxyphenyl)-1-{2-[(1S)-2-hydroxy-1,2-dimethyl-propylamino]-pyrimidin-4-yl}-3-(2,3,6-trichlorophenyl)-urea;
1-(4-Methoxyphenyl)-1-{2-[(1S)-2-hydroxy-1,2-dimethyl-propylamino]-pyrimidin-4-yl}-3-(2,4,5-trichlorophenyl)-urea; and
1-(4-Methoxyphenyl)-1-{2-[(1S)-2-hydroxy-1,2-dimethyl-propylamino]-pyrimidin-4-yl}-3-(2,4,6-trichlorophenyl)-urea.

53. A compound chosen from:
1-(4-Fluorophenyl)-1-{2-[(1S)-2-hydroxy-1,2-dimethyl-propylamino]-pyrimidin-4-yl}-3-o-methylbenzyl-urea;
1-(4-Fluorophenyl)-1-{2-[(1S)-2-hydroxy-1,2-dimethyl-propylamino]-pyrimidin-4-yl}-3-m-methylbenzyl-urea;
1-(4-Fluorophenyl)-1-{2-[(1S)-2-hydroxy-1,2-dimethyl-propylamino]-pyrimidin-4-yl}-3-p-methylbenzyl-urea;
1-(4-Fluorophenyl)-1-{2-[(1S)-2-hydroxy-1,2-dimethyl-propylamino]-pyrimidin-4-yl}-3-(2-fluorobenzyl)-urea;
1-(4-Fluorophenyl)-1-{2-[(1S)-2-hydroxy-1,2-dimethyl-propylamino]-pyrimidin-4-yl}-3-(3-fluorobenzyl)-urea;
1-(4-Fluorophenyl)-1-{2-[(1S)-2-hydroxy-1,2-dimethyl-propylamino]-pyrimidin-4-yl}-3-(4-fluorobenzyl)-urea;
1-(4-Fluorophenyl)-1-{2-[(1S)-2-hydroxy-1,2-dimethyl-propylamino]-pyrimidin-4-yl}-3-(2,3-difluorobenzyl)-urea;
1-(4-Fluorophenyl)-1-{2-[(1S)-2-hydroxy-1,2-dimethyl-propylamino]-pyrimidin-4-yl}-3-(2,4-difluorobenzyl)-urea;
1-(4-Fluorophenyl)-1-{2-[(1S)-2-hydroxy-1,2-dimethyl-propylamino]-pyrimidin-4-yl}-3-(2,5-difluorobenzyl)-urea;
1-(4-Fluorophenyl)-1-{2-[(1S)-2-hydroxy-1,2-dimethyl-propylamino]-pyrimidin-4-yl}-3-(2,6-difluorobenzyl)-urea;
1-(4-Fluorophenyl)-1-{2-[(1S)-2-hydroxy-1,2-dimethyl-propylamino]-pyrimidin-4-yl}-3-(2,3,4-trifluorobenzyl)-urea;
1-(4-Fluorophenyl)-1-{2-[(1S)-2-hydroxy-1,2-dimethyl-propylamino]-pyrimidin-4-yl}-3-(2,3,5-trifluorobenzyl)-urea;
1-(4-Fluorophenyl)-1-{2-[(1S)-2-hydroxy-1,2-dimethyl-propylamino]-pyrimidin-4-yl}-3-(2,3,6-trifluorobenzyl)-urea;
1-(4-Fluorophenyl)-1-{2-[(1S)-2-hydroxy-1,2-dimethyl-propylamino]-pyrimidin-4-yl}-3-(2,4,5-trifluorobenzyl)-urea;
1-(4-Fluorophenyl)-1-{2-[(1S)-2-hydroxy-1,2-dimethyl-propylamino]-pyrimidin-4-yl}-3-(2,4,6-trifluorobenzyl)-urea;
1-(4-Fluorophenyl)-1-{2-[(1S)-2-hydroxy-1,2-dimethyl-propylamino]-pyrimidin-4-yl}-3-(3-chlorobenzyl)-urea;
1-(4-Fluorophenyl)-1-{2-[(1S)-2-hydroxy-1,2-dimethyl-propylamino]-pyrimidin-4-yl}-3-(4-chlorobenzyl)-urea;
1-(4-Fluorophenyl)-1-{2-[(1S)-2-hydroxy-1,2-dimethyl-propylamino]-pyrimidin-4-yl}-3-(2,3-dichlorobenzyl)-urea;
1-(4-Fluorophenyl)-1-{2-[(1S)-2-hydroxy-1,2-dimethyl-propylamino]-pyrimidin-4-yl }-3-(2,4-dichlorobenzyl)-urea;

1-(4-Fluorobenzyl)-1-{2-[(1S)-2-hydroxy-1,2-dimethyl-propylamino]-pyrimidin-4-yl}-3-(2,5-dichlororobenyl)-urea;
1-(4-Fluorophenyl)-1-{2-[(1S)-2-hydroxy-1,2-dimethyl-propylamino]-pyrimidin-4-yl}-3-(2,6-dichlorobenzyl)-urea;
1-(4-Fluorophenyl)-1-{2-[(1S)-2-hydroxy-1,2-dimethyl-propylamino]-pyrimidin-4-yl}-3-(2,3,4-trichlorobenzyl)-urea;
1-(4-Fluorophenyl)-1-{2-[(1S)-2-hydroxy-1,2-dimethyl-propylamino]-pyrimidin-4-yl}-3-(2,3,5-trichlorobenzyl)-urea;
1-(4-Fluorophenyl)-1-{2-[(1S)-2-hydroxy-1,2-dimethyl-propylamino]-pyrimidin-4-yl}-3-(2,3,6-trichlorobenzyl)-urea;
1-(4-Fluorophenyl)-1-{2-[(1S)-2-hydroxy-1,2-dimethyl-propylamino]-pyrimidin-4-yl}-3-(2,4,5-trichlorobenzyl)-urea;
1-(4-Fluorophenyl)-1-{2-[(1S)-2-hydroxy-1,2-dimethyl-propylamino]-pyrimidin-4-yl}-3-(2,4,6-trichlorobenzyl)-urea;
1-(4-Methoxyphenyl)-1-{2-[(1S)-2-hydroxy-1,2-dimethyl-propylamino]-pyrimidin-4-yl}-3-(3-chlorobenzyl)-urea;
1-(4-Methoxyphenyl)-1-{2-[(1S)-2-hydroxy-1,2-dimethyl-propylamino]-pyrimidin-4-yl}-3-(4-chlorobenzyl)-urea;
1-(4-Methoxyphenyl)-1-{2-[(1S)-2-hydroxy-1,2-dimethyl-propylamino]-pyrimidin-4-yl}-3-(2,3-dichlorobenzyl)-urea;
1-(4-Methoxyphenyl)-1-{2-[(1S)-2-hydroxy-1,2-dimethyl-propylamino]-pyrimidin-4-yl}-3-(2,4-dichlorobenzyl)-urea;
1-(4-Methoxybenzyl)-1-{2-[(1S)-2-hydroxy-1,2-dimethyl-propylamino]-pyrimidin-4-yl}-3-(2,5-difluorobenzyl)-urea;
1-(4-Methoxyphenyl)-1-{2-[(1S)-2-hydroxy-1,2-dimethyl-propylamino]-pyrimidin-4-yl}-3-(2,6-dichlorobenzyl)-urea;
1-(4-Methoxyphenyl)-1-{2-[(1S)-2-hydroxy-1,2-dimethyl-propylamino]-pyrimidin-4-yl}-3-(2,3,4-trichlorobenzyl)-urea;
1-(4-Methoxyphenyl)-1-{2-[(1S)-2-hydroxy-1,2-dimethyl-propylamino]-pyrimidin-4-yl}-3-(2,3,5-trichlorobenzyl)-urea;
1-(4-Methoxyphenyl)-1-{2-[(1S)-2-hydroxy-1,2-dimethyl-propylamino]-pyrimidin-4-yl}-3-(2,3,6-trichlorobenzyl)-urea;
1-(4-Methoxyphenyl)-1-{2-[(1S)-2-hydroxy-1,2-dimethyl-propylamino]-pyrimidin-4-yl}-3-(2,4,5-trichlorobenzyl)-urea; and
1-(4-Methoxyphenyl)-1-{2-[(1S)-2-hydroxy-1,2-dimethyl-propylamino]-pyrimidin-4-yl}-3-(2,4,6-trichlorobenzyl)-urea.

54. A compound chosen from:
1-(4-Methoxyphenyl)-1-{2-[(1S)-2-methoxy-1-methyl-ethylamino]-pyrimidin-4-yl}-3-(2-chlorobenzyl)-urea;
1-(4-Methoxyphenyl)-1-{2-[(1S)-2-methoxy-1-methyl-ethylamino]-pyrimidin-4-yl}-3-(2-methylbenzyl)-urea;
1-(4-Methoxyphenyl)-1-{2-[(1S)-2-methoxy-1-methyl-ethylamino]-pyrimidin-4-yl}-3-(2,4-dichlorobenzyl)-urea;
1-(4-Methoxyphenyl)-1-{2-[(1S)-2-methoxy-1-methyl-ethylamino]-pyrimidin-4-yl}-3-(3,4-dichlorobenzyl)-urea;
1-(4-Ethoxyphenyl)-1-{2-[(1S)-2-methoxy-1-methyl-ethylamino]-pyrimidin-4-yl}-3-(2-chlorobenzyl)-urea;
1-(4-Fluorophenyl)-1-{2-[(1S)-2-methoxy-1-methyl-ethylamino]-pyrimidin-4-yl}-3-(2-fluorophenyl)-urea;
1-(4-Fluorophenyl)-1-{2-[(1S)-2-methoxy-1-methyl-ethylamino]-pyrimidin-4-yl}-3-(2-chlorophenyl)-urea;
1-(4-Fluorophenyl)-1-{2-[(1S)-2-methoxy-1-methylethylamino]-pyrimidin-4-yl}-3-(3-chlorobenzyl)-urea;
1-(4-Fluorophenyl)-1-{2-[(1S)-2-methoxy-1-methyl-ethylamino]-pyrimidin-4-yl}-3-(4-trifluoromethylphenyl)-urea;
1-(4-Fluorophenyl)-1-{2-[(1S)-2-methoxy-1-methyl-ethylamino]-pyrimidin-4-yl}-3-o-tolyl-urea;
1-(4-Dimethylaminophenyl)-1-{2-[(1S)-2-methoxy-1-methyl-ethylamino]-pyrimidin-4-yl}-3-(2-chlorophenyl)-urea;
1-(4-Dimethylaminophenyl)-1-{2-[(1S)-2-methoxy-1-methyl-ethylamino]-pyrimidin-4-yl}-3-(3-chlorophenyl)-urea;
1-(4-Methylsulfanylphenyl)-1-{2-[(1S)-2-methoxy-1-methylethylamino]-pyrimidin-4-yl}-3-(2-methylbenzyl)-urea; and
1-(4-Fluorophenyl)-1-{2-[(1S)-2-methoxy-1-methylethylamino]-pyrimidin-4-yl}-3-(2-methylbenzyl)-urea.

55. A compound chosen from:
1-Phenyl-1-{2-[(1S)-2-methoxy-1-methyl-ethylamino]-pyrimidin-4-yl}-3-m-tolyl-urea;
1-Phenyl-1-{2-[(1S)-2-methoxy-1-methyl-ethylamino]-pyrimidin-4-yl}-3-p-tolyl-urea;
1-Phenyl-1-{2-[(1S)-2-methoxy-1-methyl-ethylamino]-pyrimidin-4-yl}-3-(2-fluorophenyl)-urea;
1-Phenyl-1-{2-[(1S)-2-methoxy-1-methyl-ethylamino]-pyrimidin-4-yl}-3-(3-fluorophenyl)-urea;
1-Phenyl-1-{2-[(1S)-2-methoxy-1-methyl-ethylamino]-pyrimidin-4-yl}-3-(4-phenyl)-urea;
1-Phenyl-1-{2-[(1S)-2-methoxy-1-methyl-ethylamino]-pyrimidin-4-yl}-3-(2,3-difluorophenyl)-urea;
1-Phenyl-1-{2-[(1S)-2-methoxy-1-methyl-ethylamino]-pyrimidin-4-yl}-3-(2,4-difluorophenyl)-urea;
1-Phenyl-1-{2-[(1S)-2-methoxy-1-methyl-ethylamino]-pyrimidin-4-yl}-3-(2,5-difluorophenyl)-urea;
1-Phenyl-1-{2-[(1S)-2-methoxy-1-methyl-ethylamino]-pyrimidin-4-yl}-3-(2,6-difluorophenyl)-urea;
1-Phenyl-1-{2-[(1S)-2-methoxy-1-methyl-ethylamino]-pyrimidin-4-yl}-3-(2,3,4-trifluorophenyl)-urea;
1-Phenyl-1-{2-[(1S)-2-methoxy-1-methyl-ethylamino]-pyrimidin-4-yl}-3-(2,3,5-trifluorophenyl)-urea;
1-Phenyl-1-{2-[(1S)-2-methoxy-1-methyl-ethylamino]-pyrimidin-4-yl}-3-(2,3,6-trifluorophenyl)-urea;
1-Phenyl-1-{2-[(1S)-2-methoxy-1-methyl-ethylamino]-pyrimidin-4-yl}-3-(2,4,5-trifluorophenyl)-urea;
1-Phenyl-1-{2-[(1S)-2-methoxy-1-methyl-ethylamino]-pyrimidin-4-yl}-3-(2,4,6-trifluorophenyl)-urea;
1-Phenyl-1-{2-[(1S)-2-methoxy-1-methyl-ethylamino]-pyrimidin-4-yl}-3-(3-chlorophenyl)-urea;
1-Phenyl-1-{2-[(1S)-2-methoxy-1-methyl-ethylamino]-pyrimidin-4-yl}-3-(4-chlorophenyl)-urea;
1-Phenyl-1-{2-[(1S)-2-methoxy-1-methyl-ethylamino]-pyrimidin-4-yl}-3-(2,3-dichlorophenyl)-urea;
1-Phenyl-1-{2-[(1S)-2-methoxy-1-methyl-ethylamino]-pyrimidin-4-yl}-3-(2,4-dichlorophenyl)-urea;
1-Phenyl-1-{2-[(1S)-2-methoxy-1-methyl-ethylamino]-pyrimidin-4-yl}-3-(2,5-dichlorophenyl)-urea;
1-Phenyl-1-{2-[(1S)-2-methoxy-1-methyl-ethylamino]-pyrimidin-4-yl}-3-(2,6-dichlorophenyl)-urea;
1-Phenyl-1-{2-[(1S)-2-methoxy-1-methyl-ethylamino]-pyrimidin-4-yl}-3-(2,3,4-trichlorophenyl)-urea;
1-Phenyl-1-{2-[(1S)-2-methoxy-1-methyl-ethylamino]-pyrimidin-4-yl}-3-(2,3,5-trichlorophenyl)-urea;

1-Phenyl-1-{2-[(1S)-2-methoxy-1-methyl-ethylamino]-pyrimidin-4-yl}-3-(2,3,6-trichlorophenyl)-urea;
1-Phenyl-1-{2-[(1S)-2-methoxy-1-methyl-ethylamino]-pyrimidin-4-yl}-3-(2,4,5-trichlorophenyl)-urea;
1-Phenyl-1-{2-[(1S)-2-methoxy-1-methyl-ethylamino]-pyrimidin-4-yl}-3-(2,4,6-trichlorophenyl)-urea;
1-(4-Fluorophenyl)-1-{2-[(1S)-2-methoxy-1-methyl-ethylamino]-pyrimidin-4-yl}-3-m-tolyl-urea;
1-(4-Fluorophenyl)-1-{2-[(1S)-2-methoxy-1-methyl-ethylamino]-pyrimidin-4-yl}-3-p-tolyl-urea;
1-(4-Fluorophenyl)-1-{2-[(1S)-2-methoxy-1-methyl-ethylamino]-pyrimidin-4-yl}-3-(3-fluorophenyl)-urea;
1-(4-Fluorophenyl)-1-{2-[(1S)-2-methoxy-1-methyl-ethylamino]-pyrimidin-4-yl}-3-(4-fluorophenyl)-urea;
1-(4-Fluorophenyl)-1-{2-[(1S)-2-methoxy-1-methyl-ethylamino]-pyrimidin-4-yl}-3-(2,3-difluorophenyl)-urea;
1-(4-Fluorophenyl)-1-{2-[(1S)-2-methoxy-1-methyl-ethylamino]-pyrimidin-4-yl}-3-(2,4-difluorophenyl)-urea;
1-(4-Fluorophenyl)-1-{2-[(1S)-2-methoxy-1-methyl-ethylamino]-pyrimidin-4-yl}-3-(2,5-difluorophenyl)-urea;
1-(4-Fluorophenyl)-1-{2-[(1S)-2-methoxy-1-methyl-ethylamino]-pyrimidin-4-yl}-3-(2,6-difluorophenyl)-urea;
1-(4-Fluorophenyl)-1-{2-[(1S)-2-methoxy-1-methyl-ethylamino]-pyrimidin-4-yl}-3-(2,3,4-trifluorophenyl)-urea;
1-(4-Fluorophenyl)-1-{2-[(1S)-2-methoxy-1-methyl-ethylamino]-pyrimidin-4-yl}-3-(2,3,5-trifluorophenyl)-urea;
1-(4-Fluorophenyl)-1-{2-[(1S)-2-methoxy-1-methyl-ethylamino]-pyrimidin-4-yl}-3-(2,3,6-trifluorophenyl)-urea;
1-(4-Fluorophenyl)-1-{2-[(1S)-2-methoxy-1-methyl-ethylamino]-pyrimidin-4-yl}-3-(2,4,5-trifluorophenyl)-urea;
1-(4-Fluorophenyl)-1-{2-[(1S)-2-methoxy-1-methyl-ethylamino]-pyrimidin-4-yl}-3-(2,4,6-trifluorophenyl)-urea;
1-(4-Fluorophenyl)-1-{2-[(1S)-2-methoxy-1-methyl-ethylamino]-pyrimidin-4-yl}-3-(3-chlorophenyl)-urea;
1-(4-Fluorophenyl)-1-{2-[(1S)-2-methoxy-1-methyl-ethylamino]-pyrimidin-4-yl}-3-(4-chlorophenyl)-urea;
1-(4-Fluorophenyl)-1-{2-[(1S)-2-methoxy-1-methyl-ethylamino]-pyrimidin-4-yl}-3-(2,3-dichlorophenyl)-urea;
1-(4-Fluorophenyl)-1-{2-[(1S)-2-methoxy-1-methyl-ethylamino]-pyrimidin-4-yl}-3-(2,4-dichlorophenyl)-urea;
1-(4-Fluorophenyl)-1-{2-[(1S)-2-methoxy-1-methyl-ethylamino]-pyrimidin-4-yl}-3-(2,5-dichlorophenyl)-urea;
1-(4-Fluorophenyl)-1-{2-[(1S)-2-methoxy-1-methyl-ethylamino]-pyrimidin-4-yl}-3-(2,3,4-trichlorophenyl)-urea;
1-(4-Fluorophenyl)-1-{2-[(1S)-2-methoxy-1-methyl-ethylamino]-pyrimidin-4-yl}-3-(2,3,5-trichlorophenyl)-urea;
1-(4-Fluorophenyl)-1-{2-[(1S)-2-methoxy-1-methyl-ethylamino]-pyrimidin-4-yl}-3-(2,3,6-trichlorophenyl)-urea;
1-(4-Fluorophenyl)-1-{2-[(1S)-2-methoxy-1-methyl-ethylamino]-pyrimidin-4-yl}-3-(2,4,5-trichlorophenyl)-urea;
1-(4-Fluorophenyl)-1-{2-[(1S)-2-methoxy-1-methyl-ethylamino]-pyrimidin-4-yl}-3-(2,4,6-trichlorophenyl)-urea;
1-(4-Methoxyphenyl)-1-{2-[(1S)-2-methoxy-1-methyl-ethylamino]-pyrimidin-4-yl}-3-m-tolyl-urea;
1-(4-Methoxyphenyl)-1-{2-[(1S)-2-methoxy-1-methyl-ethylamino]-pyrimidin-4-yl}-3-p-tolyl-urea;
1-(4-Methoxyphenyl)-1-{2-[(1S)-2-methoxy-1-methyl-ethylamino]-pyrimidin-4-yl}-3-(2-fluorophenyl)-urea;
1-(4-Methoxyphenyl)-1-{2-[(1S)-2-methoxy-1-methyl-ethylamino]-pyrimidin-4-yl}-3-(3-fluorophenyl)-urea;
1-(4-Methoxyphenyl)-1-{2-[(1S)-2-methoxy-1-methyl-ethylamino]-pyrimidin-4-yl}-3-(4-fluorophenyl)-urea;
1-(4-Methoxyphenyl)-1-{2-[(1S)-2-methoxy-1-methyl-ethylamino]-pyrimidin-4-yl}-3-(2,3-difluorophenyl)-urea;
1-(4-Methoxyphenyl)-1-{2-[(1S)-2-methoxy-1-methyl-ethylamino]-pyrimidin-4-yl}-3-(2,4-difluorophenyl)-urea;
1-(4-Methoxyphenyl)-1-{2-[(1S)-2-methoxy-1-methyl-ethylamino]-pyrimidin-4-yl}-3-(2,5-difluorophenyl)-urea;
1-(4-Methoxyphenyl)-1-{2-[(1S)-2-methoxy-1-methyl-ethylamino]-pyrimidin-4-yl}-3-(2,6-difluorophenyl)-urea;
1-(4-Methoxyphenyl)-1-{2-[(1S)-2-methoxy-1-methyl-ethylamino]-pyrimidin-4-yl}-3-(2,3,4-trifluorophenyl)-urea;
1-(4-Methoxyphenyl)-1-{2-[(1S)-2-methoxy-1-methyl-ethylamino]-pyrimidin-4-yl}-3-(2,3,5-trifluorophenyl)-urea;
1-(4-Methoxyphenyl)-1-{2-[(1S)-2-methoxy-1-methyl-ethylamino]-pyrimidin-4-yl}-3-(2,3,6-trifluorophenyl)-urea;
1-(4-Methoxyphenyl)-1-{2-[(1S)-2-methoxy-1-methyl-ethylamino]-pyrimidin-4-yl}-3-(2,4,5-trifluorophenyl)-urea;
1-(4-Methoxyphenyl)-1-{2-[(1S)-2-methoxy-1-methyl-ethylamino]-pyrimidin-4-yl}-3-(2,4,6-trifluorophenyl)-urea;
1-(4-Methoxyphenyl)-1-{2-[(1S)-2-methoxy-1-methyl-ethylamino]-pyrimidin-4-yl}-3-(3-chlorophenyl)-urea;
1-(4-Methoxyphenyl)-1-{2-[(1S)-2-methoxy-1-methyl-ethylamino]-pyrimidin-4-yl}-3-(4-chlorophenyl)-urea;
1-(4-Methoxyphenyl)-1-{2-[(1S)-2-methoxy-1-methyl-ethylamino]-pyrimidin-4-yl}-3-(2,3-dichlorophenyl)-urea;
1-(4-Methoxyphenyl)-1-{2-[(1S)-2-methoxy-1-methyl-ethylamino]-pyrimidin-4-yl}-3-(2,4-dichlorophenyl)-urea;
1-(4-Methoxyphenyl)-1-{2-[(1S)-2-methoxy-1-methyl-ethylamino]-pyrimidin-4-yl}-3-(2,5-dichlorophenyl)-urea;
1-(4-Methoxyphenyl)-1-{2-[(1S)-2-methoxy-1-methyl-ethylamino]-pyrimidin-4-yl}-3-(2,6-dichlorophenyl)-urea;
1-(4-Methoxyphenyl)-1-{2-[(1S)-2-methoxy-1-methyl-ethylamino]-pyrimidin-4-yl}-3-(2,3,4-trichlorophenyl)-urea;
1-(4-Methoxyphenyl)-1-{2-[(1S)-2-methoxy-1-methyl-ethylamino]-pyrimidin-4-yl}-3-(2,3,5-trichlorophenyl)-urea;
1-(4-Methoxyphenyl)-1-{2-[(1S)-2-methoxy-1-methyl-ethylamino]-pyrimidin-4-yl}-3-(2,3,6-trichlorophenyl)-urea;

1-(4-Methoxyphenyl)-1-{2-[(1S)-2-methoxy-1-methyl-ethylamino]-pyrimidin-4-yl}-3-(2,4,5-trichlorophenyl)-urea; and 1-(4-Methoxyphenyl)-1-{2-[(1S)-2-methoxy-1-methyl-ethylamino]-pyrimidin-4-yl}-3-(2,4,6-trichlorophenyl)-urea.

56. A compound chosen from:

1-(4-Fluorophenyl)-1-{2-[(1S)-2-methoxy-1-methyl-ethylamino]-pyrimidin-4-yl}-3-m-methylbenzyl-urea;

1-(4-Fluorophenyl)-1-{2-[(1S)-2-methoxy-1-methyl-ethylamino]-pyrimidin-4-yl}-3-p-methylbenzyl-urea;

1-(4-Fluorophenyl)-1-{2-[(1S)-2-methoxy-1-methyl-ethylamino]-pyrimidin-4-yl}-3-(2-fluorobenzyl)-urea;

1-(4-Fluorophenyl)-1-{2-[(1S)-2-methoxy-1-methyl-ethylamino]-pyrimidin-4-yl}-3-(3-fluorobenzyl)-urea;

1-(4-Fluorophenyl)-1-{2-[(1S)-2-methoxy-1-methyl-ethylamino]-pyrimidin-4-yl}-3-(4-fluorobenzyl)-urea;

1-(4-Fluorophenyl)-1-{2-[(1S)-2-methoxy-1-methyl-ethylamino]-pyrimidin-4-yl}-3-(2,3-difluorobenzyl)-urea;

1-(4-Fluorophenyl)-1-{2-[(1S)-2-methoxy-1-methyl-ethylamino]-pyrimidin-4-yl}-3-(2,4-difluorobenzyl)-urea;

1-(4-Fluorophenyl)-1-{2-[(1S)-2-methoxy-1-methyl-ethylamino]-pyrimidin-4-yl}-3-(2,5-difluorobenzyl)-urea;

1-(4-Fluorophenyl)-1-{2-[(1S)-2-methoxy-1-methyl-ethylamino]-pyrimidin-4-yl}-3-(2,6-difluorobenzyl)-urea;

1-(4-Fluorophenyl)-1-{2-[(1S)-2-methoxy-1-methyl-ethylamino]-pyrimidin-4-yl}-3-(2,3,4-trifluorobenzyl)-urea;

1-(4-Fluorophenyl)-1-{2-[(1S)-2-methoxy-1-methyl-ethylamino]-pyrimidin-4-yl}-3-(2,3,5-trifluorobenzyl)-urea;

1-(4-Fluorophenyl)-1-{2-[(1S)-2-methoxy-1-methyl-ethylamino]-pyrimidin-4-yl}-3-(2,3,6-trifluorobenzyl)-urea;

1-(4-Fluorophenyl)-1-{2-[(1S)-2-methoxy-1-methyl-ethylamino]-pyrimidin-4-yl}-3-(2,4,5-trifluorobenzyl)-urea;

1-(4-Fluorophenyl)-1-{2-[(1S)-2-methoxy-1-methyl-ethylamino]-pyrimidin-4-yl}-3-(2,4,6-trifluorobenzyl)-urea;

1-(4-Fluorophenyl)-1-{2-[(1S)-2-methoxy-1-methyl-ethylamino]-pyrimidin-4-yl}-3-(3-chlorobenzyl)-urea;

1-(4-Fluorophenyl)-1-{2-[(1S)-2-methoxy-1-methyl-ethylamino]-pyrimidin-4-yl}-3-(4-chlorobenzyl)-urea;

1-(4-Fluorophenyl)-1-{2-[(1S)-2-methoxy-1-methyl-ethylamino]-pyrimidin-4-yl}-3-(2,3-dichlorobenzyl)-urea;

1-(4-Fluorophenyl)-1-{2-[(1S)-2-methoxy-1-methyl-ethylamino]-pyrimidin-4-yl}-3-(2,4-dichlorobenzyl)-urea;

1-(4-Fluorobenzyl)-1-{2-[(1S)-2-methoxy-1-methyl-ethylamino]-pyrimidin-4-yl}-3-(2,5-difluorophenyl)-urea;

1-(4-Fluorophenyl)-1-{2-[(1S)-2-methoxy-1-methyl-ethylamino]-pyrimidin-4-yl}-3-(2,6-dichlorobenzyl)-urea;

1-(4-Fluorophenyl)-1-{2-[(1S)-2-methoxy-1-methyl-ethylamino]-pyrimidin-4-yl}-3-(2,3,4-trichlorobenzyl)-urea;

1-(4-Fluorophenyl)-1-{2-[(1S)-2-methoxy-1-methyl-ethylamino]-pyrimidin-4-yl}-3-(2,3,5-trichlorobenzyl)-urea;

1-(4-Fluorophenyl)-1-{2-[(1S)-2-methoxy-1-methyl-ethylamino]-pyrimidin-4-yl}-3-(2,3,6-trichlorobenzyl)-urea;

1-(4-Fluorophenyl)-1-{2-[(1S)-2-methoxy-1-methyl-ethylamino]-pyrimidin-4-yl}-3-(2,4,5-trichlorobenzyl)-urea;

1-(4-Fluorophenyl)-1-{2-[(1S)-2-methoxy-1-methyl-ethylamino]-pyrimidin-4-yl}-3-(2,4,6-trichlorobenzyl)-urea;

1-(4-Methoxyphenyl)-1-{2-[(1S)-2-methoxy-1-methyl-ethylamino]-pyrimidin-4-yl}-3-(3-chlorobenzyl)-urea;

1-(4-Methoxyphenyl)-1-{2-[(1S)-2-methoxy-1-methyl-ethylamino]-pyrimidin-4-yl}-3-(4-chlorobenzyl)-urea;

1-(4-Methoxyphenyl)-1-{2-[(1S)-2-methoxy-1-methyl-ethylamino]-pyrimidin-4-yl}-3-(2,3-dichlorobenzyl)-urea;

1-(4-Methoxyphenyl)-1-{2-[(1S)-2-methoxy-1-methyl-ethylamino]-pyrimidin-4-yl}-3-(2,4-dichlorobenzyl)-urea;

1-(4-Methoxybenzyl)-1-{2-[(1S)-2-methoxy-1-methyl-ethylamino]-pyrimidin-4-yl}-3-(2,5-difluorophenyl)-urea;

1-(4-Methoxyphenyl)-1-{2-[(1S)-2-methoxy-1-methyl-ethylamino]-pyrimidin-4-yl}-3-(2,6-dichlorobenzyl)-urea;

1-(4-Methoxyphenyl)-1-{2-[(1S)-2-methoxy-1-methyl-ethylamino]-pyrimidin-4-yl}-3-(2,3,4-trichlorobenzyl)-urea;

1-(4-Methoxyphenyl)-1-{2-[(1S)-2-methoxy-1-methyl-ethylamino]-pyrimidin-4-yl}-3-(2,3,5-trichlorobenzyl)-urea;

1-(4-Methoxyphenyl)-1-{2-[(1S)-2-methoxy-1-methyl-ethylamino]-pyrimidin-4-yl}-3-(2,3,6-trichlorobenzyl)-urea;

1-(4-Methoxyphenyl)-1-{2-[(1S)-2-methoxy-1-methyl-ethylamino]-pyrimidin-4-yl}-3-(2,4,5-trichlorobenzyl)-urea; and 1-(4-Methoxyphenyl)-1-{2-[(1S)-2-methoxy-1-methyl-ethylamino]-pyrimidin-4-yl}-3-(2,4,6-trichlorobenzyl)-urea.

57. A compound chosen from:

1-(2-Fluorophenyl)-1-{2-[(1S)-1-phenyl-ethylamino]-pyrimidin-4-yl}-3-(2-chlorophenyl)-urea;

1-(3-Fluorophenyl)-1-{2-[(1S)-1-phenyl-ethylamino]-pyrimidin-4-yl}-3-(2-chlorophenyl)-urea;

1-(4-Fluorophenyl)-1-{2-[(1S)-1-phenyl-ethylamino]-pyrimidin-4-yl}-3-(2-chlorophenyl)-urea;

1-(4-Dimethylaminophenyl)-1-{2-[(1S)-1-phenyl-ethylamino]-pyrimidin-4-yl}-3-(2-chlorophenyl)-urea; and 1-(4-Dimethylaminophenyl)-1-{2-[(1S)-1-phenyl-ethylamino]-pyrimidin-4-yl}-3-o-tolyl-urea.

58. A compound chosen from:

1-(2-Fluorophenyl)-1-{2-[(1S)-1-phenyl-ethylamino]-pyrimidin-4-yl}-3-phenyl-urea;

1-(3-Fluorophenyl)-1-{2-[(1S)-1-phenyl-ethylamino]-pyrimidin-4-yl}-3-phenyl-urea;

1-(4-Fluorophenyl)-1-{2-[(1S)-1-phenyl-ethylamino]-pyrimidin-4-yl}-3-phenyl-urea;

1-(2-Fluorophenyl)-1-{2-[(1S)-1-phenyl-ethylamino]-pyrimidin-4-yl}-3-(3-fluorophenyl)-urea;

1-(2-Fluorophenyl)-1-{2-[(1S)-1-phenyl-ethylamino]-pyrimidin-4-yl}-3-(4-fluorophenyl)-urea;

1-(2-Fluorophenyl)-1-{2-[(1S)-1-phenyl-ethylamino]-pyrimidin-4-yl}-3-(2,6-difluorophenyl)-urea;

1-(3-Fluorophenyl)-1-{2-[(1S)-1-phenyl-ethylamino]-pyrimidin-4-yl}-3-(3-fluorophenyl)-urea;

1-(3-Fluorophenyl)-1-{2-[(1S)-1-phenyl-ethylamino]-pyrimidin-4-yl}-3-(4-fluorophenyl)-urea;
1-(3-Fluorophenyl)-1-{2-[(1S)-1-phenyl-ethylamino]-pyrimidin-4-yl}-3-(2,6-difluorophenyl)-urea;
1-(4-Fluorophenyl)-1-{2-[(1S)-1-phenyl-ethylamino]-pyrimidin-4-yl}-3-(2-fluorophenyl)-urea;
1-(4-Fluorophenyl)-1-{2-[(1S)-1-phenyl-ethylamino]-pyrimidin-4-yl}-3-(3-fluorophenyl)-urea;
1-(4-Fluorophenyl)-1-{2-[(1S)-1-phenyl-ethylamino]-pyrimidin-4-yl}-3-(4-fluorophenyl)-urea;
1-(4-Fluorophenyl)-1-{2-[(1S)-1-phenyl-ethylamino]-pyrimidin-4-yl}-3-(2,6-difluorophenyl)-urea;
1-(2-Fluorophenyl)-1-{2-[(1S)-1-phenyl-ethylamino]-pyrimidin-4-yl}-3-(3-chlorophenyl)-urea;
1-(2-Fluorophenyl)-1-{2-[(1S)-1-phenyl-ethylamino]-pyrimidin-4-yl}-3-(4-chlorophenyl)-urea;
1-(2-Fluorophenyl)-1-{2-[(1S)-1-phenyl-ethylamino]-pyrimidin-4-yl}-3-(2,6-dichlorophenyl)-urea;
1-(3-Fluorophenyl)-1-{2-[(1S)-1-phenyl-ethylamino]-pyrimidin-4-yl}-3-(3-chlorophenyl)-urea;
1-(3-Fluorophenyl)-1-{2-[(1S)-1-phenyl-ethylamino]-pyrimidin-4-yl}-3-(4-chlorophenyl)-urea;
1-(3-Fluorophenyl)-1-{2-[(1S)-1-phenyl-ethylamino]-pyrimidin-4-yl}-3-(2,6-dichlorophenyl)-urea;
1-(4-Fluorophenyl)-1-{2-[(1S)-1-phenyl-ethylamino]-pyrimidin-4-yl}-3-(2-chlorophenyl)-urea;
1-(4-Fluorophenyl)-1-{2-[(1S)-1-phenyl-ethylamino]-pyrimidin-4-yl}-3-(3-chlorophenyl)-urea;
1-(4-Fluorophenyl)-1-{2-[(1S)-1-phenyl-ethylamino]-pyrimidin-4-yl}-3-(4-chlorophenyl)-urea;
1-(4-Fluorophenyl)-1-{2-[(1S)-1-phenyl-ethylamino]-pyrimidin-4-yl}-3-(2,6-dichlorophenyl)-urea;
1-(2-Dimethylaminophenyl)-1-{2-[(1S)-1-phenyl-ethylamino]-pyrimidin-4-yl}-3-phenyl-urea;
1-(3-Dimethylaminophenyl)-1-{2-[(1S)-1-phenyl-ethylamino]-pyrimidin-4-yl}-3-phenyl-urea;
1-(4-Dimethylaminophenyl)-1-{2-[(1S)-1-phenyl-ethylamino]-pyrimidin-4-yl}-3-phenyl-urea;
1-(2-Dimethylaminophenyl)-1-{2-[(1S)-1-phenyl-ethylamino]-pyrimidin-4-yl}-3-(3-fluorophenyl)-urea;
1-(2-Dimethylaminophenyl)-1-{2-[(1S)-1-phenyl-ethylamino]-pyrimidin-4-yl}-3-(4-fluorophenyl)-urea;
1-(2-Dimethylaminophenyl)-1-{2-[(1S)-1-phenyl-ethylamino]-pyrimidin-4-yl}-3-(2,6-difluorophenyl)-urea;
1-(3-Dimethylaminophenyl)-1-{2-[(1S)-1-phenyl-ethylamino]-pyrimidin-4-yl}-3-(3-fluorophenyl)-urea;
1-(3-Dimethylaminophenyl)-1-{2-[(1S)-1-phenyl-ethylamino]-pyrimidin-4-yl}-3-(4-fluorophenyl)-urea;
1-(3-Dimethylaminophenyl)-1-{2-[(1S)-1-phenyl-ethylamino]-pyrimidin-4-yl}-3-(2,6-difluorophenyl)-urea;
1-(4-Dimethylaminophenyl)-1-{2-[(1S)-1-phenyl-ethylamino]-pyrimidin-4-yl }-3-(2-fluorophenyl)-urea;
1-(4-Dimethylaminophenyl)-1-{2-[(1S)-1-phenyl-ethylamino]-pyrimidin-4-yl}-3-(3-fluorophenyl)-urea;
1-(4-Dimethylaminophenyl)-1-{2-[(1S)-1-phenyl-ethylamino]-pyrimidin-4-yl}-3-(4-fluorophenyl)-urea;
1-(4-Dimethylaminophenyl)-1-{2-[(1S)-1-phenyl-ethylamino]-pyrimidin-4-yl}-3-(2,6-difluorophenyl)-urea;
1-(2-Dimethylaminophenyl)-1-{2-[(1S)-1-phenyl-ethylamino]-pyrimidin-4-yl}-3-(3-chlorophenyl)-urea;
1-(2-Dimethylaminophenyl)-1-{2-[(1S)-1-phenyl-ethylamino]-pyrimidin-4-yl}-3-(4-chlorophenyl)-urea;
1-(2-Dimethylaminophenyl)-1-{2-[(1S)-1-phenyl-ethylamino]-pyrimidin-4-yl}-3-(2,6-dichlorophenyl)-urea;
1-(3-Dimethylaminophenyl)-1-{2-[(1S)-1-phenyl-ethylamino]-pyrimidin-4-yl}-3-(3-chlorophenyl)-urea;
1-(3-Dimethylaminophenyl)-1-{2-[(1S)-1-phenyl-ethylamino]-pyrimidin-4-yl}-3-(4-chlorophenyl)-urea;
1-(3-Dimethylaminophenyl)-1-{2-[(1S)-1-phenyl-ethylamino]-pyrimidin-4-yl}-3-(2,6-dichlorophenyl)-urea;
1-(4-Dimethylaminophenyl)-1-{2-[(1S)-1-phenyl-ethylamino]-pyrimidin-4-yl}-3-(2-chlorophenyl)-urea;
1-(4-Dimethylaminophenyl)-1-{2-[(1S)-1-phenyl-ethylamino]-pyrimidin-4-yl}-3-(3-chlorophenyl)-urea;
1-(4-Dimethylaminophenyl)-1-{2-[(1S)-1-phenyl-ethylamino]-pyrimidin-4-yl}-3-(4-chlorophenyl)-urea;
1-(4-Dimethylaminophenyl)-1-{2-[(1S)-1-phenyl-ethylamino]-pyrimidin-4-yl}-3-(2,6-dichlorophenyl)-urea;
1-(2-Dimethylaminophenyl)-1-{2-[(1S)-1-phenyl-ethylamino]-pyrimidin-4-yl}-3-o-tolyl-urea;
1-(2-Dimethylaminophenyl)-1-{2-[(1S)-1-phenyl-ethylamino]-pyrimidin-4-yl}-3-m-tolyl-urea;
1-(2-Dimethylaminophenyl)-1-{2-[(1S)-1-phenyl-ethylamino]-pyrimidin-4-yl}-3-p-tolyl-urea;
1-(3-Dimethylaminophenyl)-1-{2-[(1S)-1-phenyl-ethylamino]-pyrimidin-4-yl}-3-o-tolyl-urea;
1-(3-Dimethylaminophenyl)-1-{2-[(1S)-1-phenyl-ethylamino]-pyrimidin-4-yl}-3-m-tolyl-urea;
1-(3-Dimethylaminophenyl)-1-{2-[(1S)-1-phenyl-ethylamino]-pyrimidin-4-yl}-3-p-tolyl-urea;
1-(4-Dimethylaminophenyl)-1-{2-[(1S)-1-phenyl-ethylamino]-pyrimidin-4-yl}-3-m-tolyl-urea; and
1-(4-Dimethylaminophenyl)-1-{2-[(1S)-1-phenyl-ethylamino]-pyrimidin-4-yl}-3-p-tolyl-urea.

59. A compound chosen from:
1-(4-Fluorophenyl)-1-(2-dimethylamino-pyrimidin-4-yl)-3-(2-chlorobenzyl)-urea;
1-(4-Methoxyphenyl)-1-(2-methylamino-pyrimidin-4-yl)-3-(2-chlorobenzyl)-urea;
1-(4-Methoxy-phenyl)-1-(2-isopropylamino-pyrimidin-4-yl)-3-(2-chlorobenzyl)-urea;
1-(4-Fluoro-phenyl)-1-[2-(2,6-difluorophenylamino)-pyrimidin-4-yl]-3-(2-chlorobenzyl)-urea;
1-(1-Benzyl-piperidin-4-yl)-1-{2-[(1S)1-phenyl-ethylamino]-pyrimidin-4-yl}-3-(2-chlorophenyl)-urea;
1-(4-Fluorophenyl)-1-(2-benzylamino-pyrimidin-4-yl)-3-(2-chlorophenyl)-urea;
1-(4-methoxyphenyl)-1-{2-[(1S)-2-methoxy-1-methyl-ethylamino]-pyrimidin-4-yl}-3-cyclohexyl-urea;
1-(4-Fluorophenyl)-1-[2-(3-methyl-2,5-dioxo-2,5-dihydro-pyrrol-1-ylamino)-pyrimidin-4-yl]-3-(2-chlorophenyl)-urea;
1-(4-Fluorophenyl)-1-(2-isopropylamino-pyrimidin-4-yl)-3-pyridin-2-ylmethyl-urea;
1-(2-Methoxyphenyl)-1-{2-[(1S)-2-methoxy-1-methyl-ethylamino]-pyrimidin-4-yl}-3-cyclopentyl-urea;
1-(3-Fluorophenyl)-1-{2-[(1S)-2-methoxy-1-methylethylamino]-pyrimidin-4-yl}-3-cyclohexyl-urea;
1-(3,5-Dichlorophenyl)-1-{2-[(1S)-2-methoxy-1-methyl-ethylamino]-pyrimidin-4-yl}-3-(pyridine-2-yl)-urea;
1-(3-Methylphenyl)-1-{2-[(1S)-2-methoxy-1-methyl-ethylamino]-pyrimidin-4-yl}-3-cyclohexyl-urea; and
1-(4-Methoxyphenyl)-1-{2-[(1S)-2-methoxy-1-methyl-ethylamino]-pyrimidin-4-yl}-3-(pyridin-4-ylmethyl)-urea.

60. A compound chosen from:
1-(4-Fluorophenyl)-1-[2-(4-methyl-piperazin-1-yl)-pyrimidin-4-yl]-3-(2-chlorophenyl)-urea;
1-(4-Fluorophenyl)-1-(2-morpholin-4-yl-pyrimidin-4-yl)-3-(2-chlorophenyl)-urea;
4-{4-[3-(2-Chlorophenyl)-1-(4-fluorophenyl)-ureido]-pyrimidin-2-ylamino}-piperidine-1-carboxylic acid ethyl ester;

1-(4-Fluorophenyl)-1-[2-(tetrahydro-pyran-4-ylamino)-pyrimidin-4-yl]-3-(2-chlorophenyl)-urea;

1-(4-Fluorophenyl)-1-{2-[1-(propane-1-sulfanyl)-piperidin-4-ylamino]-pyrimidin-4-yl}-3-(2-chlorophenyl)-urea; and 1-(4-Fluorophenyl)-1-[2-(tetrahydro-pyran-4-ylamino)-pyrimidin-4-yl]-3-(2-chlorobenzyl)-urea.

61. A composition comprising:

a) an effective amount of a compound, or an enantiomeric or a diasteriomeric form, or salts thereof, said compound having the formula:

wherein R has the formula:

-(L)$_x$-R$^3$

R$^3$ is chosen from:
i) substituted or unsubstituted C$_6$-C$_{10}$ aryl;
ii) substituted or unsubstituted C$_1$-C$_{10}$ heteroaryl;
iii) substituted or unsubstituted C$_3$-C$_{10}$ carbocyclic; or
iv) substituted or unsubstituted C$_1$-C$_{10}$ heterocyclic;
the index x is 0 or 1;
R$^1$ has the formula:

-(L$^1$)$_y$-R$^5$

R$^5$ is a unit selected from the group consisting of:
i) substituted or unsubstituted C$_3$-C$_{10}$ carbocyclic;
ii) substituted or unsubstituted C$_6$-C$_{10}$ aryl;
iii) substituted or unsubstituted C$_1$-C$_{10}$ heterocyclic; and
iv) substituted or unsubstituted C$_1$-C$_{10}$ heteroaryl;
the index y is 0 or 1;
R$^2$ has the formula:

-(L$^2$)$_z$-R$^6$

R$^6$ is a unit selected from the group consisting of:
i) hydrogen;
ii) substituted or unsubstituted C$_1$-C$_{10}$ linear or branched hydrocarbyl;
iii) substituted or unsubstituted C$_3$-C$_{10}$ carbocyclic;
iv) substituted or unsubstituted C$_6$-C$_{10}$ aryl;
v) substituted or unsubstituted C$_1$-C$_{10}$ heterocyclic; and
vi) substituted or unsubstituted C$_1$-C$_{10}$ heteroaryl;
the index z is 0 or 1;
L, L$^1$ and L$^2$ are linking groups each of which are independently selected from the group consisting of:
i) —C(R$^7$)$_2$—;
ii) —NR$^7$—; and
iii) —O—;
R$^7$ is hydrogen, C$_1$-C$_4$ alkyl, and mixtures thereof; or two R$^7$ units can be taken together to form a carbonyl unit; and b) one or more excipients.

62. A composition comprising:

a) an effective amount of one or more compounds according to claim 1; and b) one or more excipients.

63. A method for treating rheumatoid arthritis or osteoarthritis in humans, said method comprising administering to humans an effective amount of a compound according to claim 1.

* * * * *